(12) United States Patent
Vriezen

(10) Patent No.: US 9,832,943 B2
(45) Date of Patent: Dec. 5, 2017

(54) SOLANUM LYCOPERSICUM PLANTS HAVING NON-TRANSGENIC ALTERATIONS IN THE ACS2 GENE

(71) Applicant: NUNHEMS B.V., AC Nunhem (NL)

(72) Inventor: Hendrik Willem Vriezen, BM Haelen (NL)

(73) Assignee: NUNHEMS B.V., Nunhem (NL)

( * ) Notice: Subject to any disclaimer, the term of this patent is extended or adjusted under 35 U.S.C. 154(b) by 0 days.

(21) Appl. No.: 14/646,190

(22) PCT Filed: Nov. 20, 2013

(86) PCT No.: PCT/EP2013/074309
§ 371 (c)(1),
(2) Date: May 20, 2015

(87) PCT Pub. No.: WO2014/079896
PCT Pub. Date: May 30, 2014

(65) Prior Publication Data
US 2015/0282446 A1    Oct. 8, 2015

(30) Foreign Application Priority Data

Nov. 21, 2012 (EP) .................................... 12193592

(51) Int. Cl.
| A01H 5/08 | (2006.01) |
| A01H 1/00 | (2006.01) |
| C12N 9/88 | (2006.01) |
| C12N 15/82 | (2006.01) |
| A23L 19/00 | (2016.01) |
| C12N 15/00 | (2006.01) |

(52) U.S. Cl.
CPC ................ *A01H 5/08* (2013.01); *A23L 19/00* (2016.08); *C12N 9/88* (2013.01); *C12N 15/8249* (2013.01); *A23V 2002/00* (2013.01); *C12Y 404/01014* (2013.01)

(58) Field of Classification Search
None
See application file for complete search history.

(56) References Cited

U.S. PATENT DOCUMENTS 5,723,766 A    3/1998  Theologis et al.

FOREIGN PATENT DOCUMENTS

| EP | 12186606.5 | 9/2012 |
| WO | 9204456 | 3/1992 |
| WO | 2005016504 | 2/2005 |
| WO | 2005048692 | 6/2005 |

OTHER PUBLICATIONS

Klee et al., Annual Review of Genetics, vol. 45:41-59, Dec. 2011.*
Alexander, L. et al, "Ethylene Biosynthesis and Action in Tomato: a Model for Climacteric Fruit Ripening," Journal of Experimental Botany (2002), vol. 53, No. 377, pp. 2039-2055.
Barry, C. et al., "The Regulation of 1-Aminocyclopropane-1-Carboxylic Acid Synthase Gene Expression During the Transition from System-1 to System-2 Ethylene Synthesis in Tomato," Plant Physiology (2000), vol. 123, No. 3, pp. 979-986, XP055055635.
Bui, H. et al., "Postharvest Ripening Characterization of Greenhouse Tomatoes," International Journal of Food Properties (2010), vol. 13, Issue 4, pp. 830-846.
Capitani, G. et al., "Structure of 1-Aminocyclopropane-1-Carboxylate Synthase, a Key Enzyme in the Biosynthesis of the Plant Hormone Ethylene," Journal of Molecular Biology (1999), vol. 294, pp. 745-756.
Chae, H. et al., "The eto1, eto2, and eto3 Mutations and Cytokinin Treatment Increase Ethylene Biosynthesis in Arabidopsis by Increasing the Stability of ACS Protein," The Plant Cell Online (2003), vol. 15, No. 2, pp. 545-559, XP055055661.
Clement, A. et al., "Nondestructive Measurement of Fresh Tomato Lycopene Content and Other Physicochemical Characteristics Using Visible-NIR Spectroscopy," Journal of Agricultural and Food Chemistry (2008), vol. 56, pp. 9813-9818.
Comai, L. et al., "Efficient Discovery of DNA Polymorphisms in Natural Populations by Ecotilling", The Plant Journal (2004), vol. 37, pp. 778-786.
Cristescu, S. et al., "Laser-Based Systems for Trace Gas Detection in Life Sciences," Applied Physics B (2008), vol. 92, pp. 343-349.
Fish, W. et al., "A Quantitative Assay for Lycopene That Utilizes Reduced Volumes of Organic Solvents," Journal of Food Composition and Analysis (2002), vol. 15, pp. 309-317.
Gady, A. et al., "Induced Point Mutations in the Phytoene Synthase 1 Gene Cause Differences in Carotenoid Content During Tomato Fruit Ripening," Molecular Breeding (2012), vol. 29, pp. 801-812.
Henikoff, S. et al., "Amino Acid Substitution Matrices From Protein Blocks," Proceedings of the National Academy of Sciences of the United States of America (1992), vol. 89, pp. 10915-10919.
Henikoff, S. et al., "Tilling. Traditional Mutagenesis Meets Functional Genomics," Plant Physiology (2004), vol. 135, pp. 630-636.
Kamiyoshihara, M. et al., "Turnover of LeACS2, a Wound-Inducible 1-Aminocyclo-Propane-1-Carboxylic Acid Synthase in Tomato, Is Regulated by Phosphorylation/Dephosphorylation," The Plant Journal (2010), vol. 64, No. 1, pp. 140-150.
Martinez-Madrid, M. et al., "Polyamine Levels and Ethylene Production in Tomato Fruit Development and Ripening," Acta Horticulturae (1995), vol. 412, pp. 463-469.
Vijee Mohan et al., "Eco-Tilling in tomato to unravel the hidden gifts of nature," SOL2010, p. 67, http://sol1010.org/sol2010/files/file/SOL2010_Abstracts.pdf (Abstract Only).

(Continued)

*Primary Examiner* — Phoenix Bui
(74) *Attorney, Agent, or Firm* — Arent Fox LLP

(57) ABSTRACT

The present invention relates to cultivated plant of the species *Solanum lycopersicum* comprising a acs2 allele having one or more mutations, said mutations resulting in production of a mutant acs2 protein having loss-of-function acs2 protein or reduced function compared to wild type Acs2 protein.

22 Claims, 7 Drawing Sheets

(56) References Cited

OTHER PUBLICATIONS

Mutschler, M. et al., "Tomato Fruit Quality and Shelf Life in Hybrids Heterozygous for the alc Ripening Mutant," Hortscience (1992), vol. 27, No. 4, pp. 352-355. Hortscience.

Oeller, P. et al., "Reversible Inhibition of Tomato Fruit Senescence by Antisense RNA," Science (1991), vol. 254, pp. 437-439.

Okabe, Y. et al., "Tomato Tilling Technology: Development of a Reverse Genetics Tool for the Efficient Isolation of Mutants from Micro-Tom Mutant Libraries," Plant and Cell Physiology (1994), vol. 52, No. 11, pp. 1994-2005, XP055055641.

Picton, S. et al., "Altered Fruit Ripening and Leaf Senescence in Tomatoes Expressing an Antisense Ethylene-Forming Enzyme Transgene," The Plant Journal (1993), vol. 3, No. 3, pp. 469-481. Enzyme.

Rigola, D. et al., "High-Throughput Detection of Induced Mutations and Natural Variation Using KeyPoint™ Technology," PloS One (2009), vol. 4, Issue 3, e4761 (9 pages).

Sirisomboon, P. et al., "Evaluation of Tomato Textural Mechanical Properties," Journal of Food Engineering (2012), vol. 111, pp. 618-624.

Stearns, J. et al., "Transgenic Plants with Altered Ethylene Biosynthesis or Perception," Biotechnology Advances (2003), vol. 21, pp. 193-210.

Tatsuki, M. et al., "Phosphorylation of Tomato 1-Aminocyclopropane-1-Carboxylic Acid Synthase, LE-ACS2, at the C-Terminal Region," The Journal of Biological Chemistry (2001), vol. 276, No. 30, pp. 28051-28057, XP055055657.

Till, B. et al., "Discovery of Induced Point Mutations in Maize Genes by Tilling," BMC Plant Biology (2004), vol. 4, No. 12 (8 pages).

Till, B. et al., "Discovery of Chemically Induced Mutations in Rice by Tilling," BMC Plant Biology (2007), vol. 7, No. 19 (12 pages).

Till, B. et al., "High-Throughput Tilling for Arabidopsis," Methods in Molecular Biology (2006), vol. 323, pp. 127-135.

Till, B. et al., "A Protocol for Tilling and Ecotilling in Plants and Animals," Nature Protocols (2006), vol. 1, No. 5, pp. 2465-2477.

University of California Davis, "Tomato Tilling," (Apr. 14, 2015), http://tilling.ucdavis.edu/index.php/Tomato_Tilling, last modified Jan. 2, 2014.

United States Department of Agriculture, Agricultural Marking Service, Fruit and Vegetable Division, Fresh Products Branch, "United States Standards for Grades of Fresh Tomatoes," Effective 1973.

United States Department of Agriculture, Agricultural Marking Service, Fruit and Vegetable Division, Fresh Products Branch, "United States Standards for Grades of Fresh Tomatoes," Effective Oct. 1, 1991, Reprinted Jan. 1997.

Yokotani, N. et al., "Ripening-Associated Ethylene Biosynthesis in Tomato Fruit is Autocatalytically and Developmentally Regulated," Journal of Experimental Botany (2009), vol. 60, No. 12, pp. 3433-3442.

Extended European Search Report of EP 12193592, dated Mar. 20, 2013.

International Search Report and Written Opinion of PCT/EP2013/074309, dated Apr. 4, 2014.

\* cited by examiner

Figure 3

```
Le-ACS2            MGFEIAKTNS ILSKLATNEE HGENSPYFDG WKAYDSDPFH PLKNPNGVIQ
LeACS2_783_prot    MGFEIAKTNS ILSKLATNEE HGENSPYFDG WKAYDSDPFH PLKNPNGVIQ
LeACS2_2145_prot   MGFEIAKTNS ILSKLATNEE HGENSPYFDG WKAYDSDPFH PLKNPNGVIQ
LeACs2_2714_prot   MGFEIAKTNS ILSKLATNEE HGENSPYFDG WKAYDSDPFH PLKNPNGVIQ
LeACS2_3793_prot   MGFEIAKTNS ILSKLATNEE HGENSPYFDG WKAYDSDPFH PLKNPNGVIQ
LeACS2_4946_prot   MGFEIAKTNS ILSKLATNEE HGENSPYFDG WKAYDSDPFH PLKNPNGVIQ
LeACS2_7871_prot   MGFEIAKTNS ILSKLATNEE HGENSPYFDG WKAYDSDPFH PLKNPNGVIQ
LeACS2_8185_prot   MGFEIAKTNS ILSKLATNEE HGENSPYFDG WKAYDSDPFH PLKNPNGVIQ Le-ACS2            MGLAENQLCL DLIEDWIKRN PKGSICSEGI KSFKAIANFQ DYHGLPEFRK
LeACS2_783_prot    MGLAENQLCL DLIEDWIKRN PKGSICSEGI KSFKAIANFQ DYHGLPEFRK
LeACS2_2145_prot   MGLAENQLCL DLIEDWIKRN PKGSICSEGI KSFKAIANFQ DYHGLPEFRK
LeACs2_2714_prot   MGLAENQLCL DLIEDWIKRN PKGSICSEGI KSFKAIANFQ DYHGLPEFRK
LeACS2_3793_prot   MGLAENQLCL DLIEDWIKRN PKGSICSEGI KSFKAIANFQ DYHGLPEFRK
LeACS2_4946_prot   MGLAENQLCL DLIEDWIKRN PKGSICSEGI KSFKAIANFQ DYHGLPEFRK
LeACS2_7871_prot   MGLAENQLCL DLIEDWIKRN PKGSICSEGI KSFKAIANFQ DYHGLPEFRK
LeACS2_8185_prot   MGLAENQLCL DLIEDWIKRN PKGSICSEGI KSFKAIANFQ DYHGLPEFRK Le-ACS2            AIAKFMEKTR GGRVRFDPER VVMAGGATGA NETIIFCLAD PGDAFLVPSP
LeACS2_783_prot    AITKFMEKTR GGRVRFDPER VVMAGGATGA NETIIFCLAD PGDAFLVPSP
LeACS2_2145_prot   AIAKFMEKTR GRRVRFDPER VVMAGGATGA NETIIFCLAD PGDAFLVPSP
LeACs2_2714_prot   AIAKFMEKTR GGRVRFDLER VVMAGGATGA NETIIFCLAD PGDAFLVPSP
LeACS2_3793_prot   VIAKFMEKTR GGRVRFDPER VVMAGGATGA NETIIFCLAD PGDAFLVPSP
LeACS2_4946_prot   TIAKFMEKTR GGRVRFDPER VVMAGGATGA NETIIFCLAD PGDAFLVPSP
LeACS2_7871_prot   AIAKFMEKTR GGRVRFDPER VVMAGGATGA NETIIFCLAD PGDAFLVPSP
LeACS2_8185_prot   AIAKFMEKTR GGRVRFDPER VVMAGGATGA NETIIFCLAD PGDAFLEPSP Le-ACS2            YYPAFNRDLR WRTGVQLIPI HCESSNNFKI TSKAVKEAYE NAQKSNIKVK
LeACS2_783_prot    YYPAFNRDLR WRTGVQLIPI HCESSNNFKI TSKAVKEAYE NAQKSNIKVK
LeACS2_2145_prot   YYPAFNRDLR WRTGVQLIPI HCESSNNFKI TSKAVKEAYE NAQKSNIKVK
LeACs2_2714_prot   YYPAFNRDLR WRTGVQLIPI HCESSNNFKI TSKAVKEAYE NAQKSNIKVK
LeACS2_3793_prot   YYPAFNRDLR WRTGVQLIPI HCESSNNFKI TSKAVKEAYE NAQKSNIKVK
LeACS2_4946_prot   YYPAFNRDLR WRTGVQLIPI HCESSNNFKI TSKAVKEAYE NAQKSNIKVK
LeACS2_7871_prot   YYPAFNRDLR WRTGVQLIPI HCESSNNFKI TSKAVKEAYE NAQKSNIKVK
LeACS2_8185_prot   YYPAFNRDLR WRTGVQLIPI HCESSNNFKI TSKAVKEAYE NAQKSNIKVK Le-ACS2            GLILTNPSNP LGTTLDKDTL KSVLSFTNQH NIHLVCDEIY AATVFDTPQF
LeACS2_783_prot    GLILTNPSNP LGTTLDKDTL KSVLSFTNQH NIHLVCDEIY AATVFDTPQF
LeACS2_2145_prot   GLILTNPSNP LGTTLDKDTL KSVLSFTNQH NIHLVCDEIY AATVFDTPQF
LeACs2_2714_prot   GLILTNPSNP LGTTLDKDTL KSVLSFTNQH NIHLVCDEIY AATVFDTPQF
LeACS2_3793_prot   GLILTNPSNP LGTTLDKDTL KSVLSFTNQH NIHLVCDEIY AATVFDTPQF
LeACS2_4946_prot   GLILTNPSNP LGTTLDKDTL KSVLSFTNQH NIHLVCDEIY AATVFDTPQF
LeACS2_7871_prot   GLILTNPSNP LGTTLDKDTL KSVLSFTNQH NIHLVCDEIY AATVFDTPQF
LeACS2_8185_prot   GLILTNPSNP LGTTLDKDTL KSVLSFTNQH NIHLVCDEIY AATVFDTPQF Le-ACS2            VSIAEILDEQ EMTYCNKDLV HIVYSLSKDM GLPGFRVGII YSFNDDVVNC
LeACS2_783_prot    VSIAEILDEQ EMTYCNKDLV HIVYSLSKDM GLPGFRVGII YSFNDDVVNC
LeACS2_2145_prot   VSIAEILDEQ EMTYCNKDLV HIVYSLSKDM GLPGFRVGII YSFNDDVVNC
LeACs2_2714_prot   VSIAEILDEQ EMTYCNKDLV HIVYSLSKDM GLPGFRVGII YSFNDDVVNC
LeACS2_3793_prot   VSIAEILDEQ EMTYCNKDLV HIVYSLSKDM GLPGFRVGII YSFNDDVVNC
LeACS2_4946_prot   VSIAEILDEQ EMTYCNKDLV HIVYSLSKDM GLPGFRVGII YSFNDDVVNC
LeACS2_7871_prot   VSIAEILDEQ EMTYYNKDLV HIVYSLSKDM GLPGFRVGII YSFNDDVVNC
LeACS2_8185_prot   VSIAEILDEQ EMTYCNKDLV HIVYSLSKDM GLPGFRVGII YSFNDDVVNC Le-ACS2            ARKMSSFGLV STQTQYFLAA MLSDEKFVDN FLRESAMRLG KRHKHFTNGL
LeACS2_783_prot    ARKMSSFGLV STQTQYFLAA MLSDEKFVDN FLRESAMRLG KRHKHFTNGL
```

Figure 3 (continued)

```
LeACS2_2145_prot    ARKMSSFGLV STQTQYFLAA MLSDEKFVDN FLRESAMRLG KRHKHFTNGL
LeACs2_2714_prot    ARKMSSFGLV STQTQYFLAA MLSDEKFVDN FLRESAMRLG KRHKHFTNGL
LeACS2_3793_prot    ARKMSSFGLV STQTQYFLAA MLSDEKFVDN FLRESAMRLG KRHKHFTNGL
LeACS2_4946_prot    ARKMSSFGLV STQTQYFLAA MLSDEKFVDN FLRESAMRLG KRHKHFTNGL
LeACS2_7871_prot    ARKMSSFGLV STQTQYFLAA MLSDEKFVDN FLRESAMRLG KRHKHFTNGL
LeACS2_8185_prot    ARKMSSFGLV STQTQYFLAA MLSDEKFVDN FLRESAMRLG KRHKHFTNGL Le-ACS2             EVVGIKCLKN NAGLFCWMDL RPLLRESTFD SEMSLWRVII NDVKLNVSPG
LeACS2_783_prot     EVVGIKCLKN NAGLFCWMDL RPLLRESTFD SEMSLWRVII NDVKLNVSPG
LeACS2_2145_prot    EVVGIKCLKN NAGLFCWMDL RPLLRESTFD SEMSLWRVII NDVKLNVSPG
LeACs2_2714_prot    EVVGIKCLKN NAGLFCWMDL RPLLRESTFD SEMSLWRVII NDVKLNVSPG
LeACS2_3793_prot    EVVGIKCLKN NAGLFCWMDL RPLLRESTFD SEMSLWRVII NDVKLNVSPG
LeACS2_4946_prot    EVVGIKCLKN NAGLFCWMDL RPLLRESTFD SEMSLWRVII NDVKLNVSPG
LeACS2_7871_prot    EVVGIKCLKN NAGLFCWMDL RPLLRESTFD SEMSLWRVII NDVKLNVSPG
LeACS2_8185_prot    EVVGIKCLKN NAGLFCWMDL RPLLRESTFD SEMSLWRVII NDVKLNVSPG Le-ACS2             SSFECQEPGW FRVCFANMDD GTVDIALARI RRFVGVEKSG DKSSSMEQKQ
LeACS2_783_prot     SSFECQEPGW FRVCFANMDD GTVDIALARI RRFVGVEKSG DKSSSMEQKQ
LeACS2_2145_prot    SSFECQEPGW FRVCFANMDD GTVDIALARI RRFVGVEKSG DKSSSMEQKQ
LeACs2_2714_prot    SSFECQEPGW FRVCFANMDD GTVDIALARI RRFVGVEKSG DKSSSMEQKQ
LeACS2_3793_prot    SSFECQEPGW FRVCFANMDD GTVDIALARI RRFVGVEKSG DKSSSMEQKQ
LeACS2_4946_prot    SSFECQEPGW FRVCFANMDD GTVDIALARI RRFVGVEKSG DKSSSMEQKQ
LeACS2_7871_prot    SSFECQEPGW FRVCFANMDD GTVDIALARI RRFVGVEKSG DKSSSMEQKQ
LeACS2_8185_prot    SSFECQEPGW FRVCFANMDD GTVDIALARI RRFVGVEKSG DKSSSMEQKQ Le-ACS2             QWKKNNLRLS FSKRMYDESV LSPLSSPIPP SPLVR
LeACS2_783_prot     QWKKNNLRLS FSKRMYDESV LSPLSSPIPP SPLVR
LeACS2_2145_prot    QWKKNNLRLS FSKRMYDESV LSPLSSPIPP SPLVR
LeACs2_2714_prot    QWKKNNLRLS FSKRMYDESV LSPLSSPIPP SPLVR
LeACS2_3793_prot    QWKKNNLRLS FSKRMYDESV LSPLSSPIPP SPLVR
LeACS2_4946_prot    QWKKNNLRLS FSKRMYDESV LSPLSSPIPP SPLVR
LeACS2_7871_prot    QWKKNNLRLS FSKRMYDESV LSPLSSPIPP SPLVR
LeACS2_8185_prot    QWKKNNLRLS FSKRMYDESV LSPLSSPIPP SPLVR
```

Figure 5

```
                                                              Small domain
ACS4_WT_ID1      MDLETSEISN YKSSVVLSKL ASNEQHGENS PYFDGWKAYD NDPFHLVNNL  50
ACS4_2477_ID2    MDLETSEISN YKSSVVLSKL ASNEQHGENS PYFDGWKAYD NDPFHLVNNL
ACS4_4043_ID3    MDLETSEISN YKSSVVLSKL ASNEQHGENS PYFDGWKAYD NDPFHLVNNL
ACS4_4222_ID4    MDLETSEISN YKSSVVLSKL ASNEQHGENS PYFDGWKAYD NDPFHLVNNL
ACS4_4303_ID5    MDLETSEISN YKSSVVLSKL ASNEQHGENS PYFDGWKAYD NDPFHLVNNL
ACS4_4691_ID6    MDLETSEISN YKSSVVLSKL ASNEQHGENS PYFDGWKAYD NDPFHLVNNL
ACS4_5251_ID7    MDLETSEISN YKSSVVLSKL ASNEQHGENS PYFDGWKAYD NDPFHLVNNL Large domain
ACS4_WT_ID1      NGVIQMGLAE NQLSVDLIEE WIKRNPKASI CTNDGIESFR RIANFQDYHG  100
ACS4_2477_ID2    NGVIQMGLAE NQLSVDLIEE WIKRNPKASI CTNDGIESFR RIANFQDYHG
ACS4_4043_ID3    NGVIQMGLAE NQLSVDLIEE WIKRNPKASI CTNDGIESFR RIANFQDYHG
ACS4_4222_ID4    NGVIQMGLAE NQLSVDLIEE WIKRNPKASI CTNDGIESFR RIANFQDYHG
ACS4_4303_ID5    NGVIQMGLAE NQLSVDLIEE WIKRNPKASI CTNDGIESFR RIANFQDYHG
ACS4_4691_ID6    NGVIQMGLAE NQLSVDLIEE WIKRNPKASI CTNDGIESFR RIANFQDYHG
ACS4_5251_ID7    NGVIQMGLAE NQLSVDLIEE WIKRNPKASI CTNDGIESFR RIANFQDYHG ACS4_WT_ID1      LPEFTNAIAK FMEKTRGGKV KFDAKRVVMA GGATGANETL ILCLADPGDA  150
ACS4_2477_ID2    LPEFTNAIAK FMEKTRGGKV KFDAKRVVMA GGATGANETL ILCLADPGDA
ACS4_4043_ID3    LPEFTNAIAK FMEKTRGGKV KFDAKRVVMA GGATGANETL ILCLADPGDA
ACS4_4222_ID4    LPEFTNAIAK FMEKTRGGKV KFDAKRVVMA GGATGANETL ILCLADPGDA
ACS4_4303_ID5    LPEFTNAIAK FMEKTRGGKV KFDAKRVVMA GGATGANETL ILCLADPGDA
ACS4_4691_ID6    LPEFTNAIAK FMEKTRGGKV KFDAKRVVMA GGATGANETL ILCLADPGDA
ACS4_5251_ID7    LPEFTNAIAK FMEKTRGGKV KFDAKRVVMA GGATGANETL ILCLADPGDA ACS4_WT_ID1      FLVPTPYYPG FNRDLRWRSG VQLLPISCKS CNNFKITIEA IEEAYEKGQQ  200
ACS4_2477_ID2    FLVPTPYYPG FNRDLRWRSG VQLLPISCKS CNNFKITIEA IEEAYEKGQQ
ACS4_4043_ID3    FLVPTPYYPG FNRDLRWRSG VQLLPISCKS CNNFKITIEA IEEAYEKGQQ
ACS4_4222_ID4    FLVPTPYYPG FNRDLRWRSG VQLLPISCKS CNNFKITIEA IEEAYEKGQQ
ACS4_4303_ID5    FLVPTPYYPG FNRDLRWRSG VQLLPISCKS CNNFKITIEA IEEAYEKGQQ
ACS4_4691_ID6    FLVPTPYYPG FNRDLRWRSG VQLLPISCKS CNNFKITIEA IEEAYEKGQQ
ACS4_5251_ID7    FLVPTPYYPG FNRDLRWRSG VQLLPISCKS CNNFKITIEA IEEAYEKGQQ ACS4_WT_ID1      ANVKIKGLIL TNPCNPLGTI LDRDTLKKIS TFTNEHNIHL VCDEIYAATV  250
ACS4_2477_ID2    ANVKIKGLIL TNPCNPLGTI LDRDTLKKIS TFTNEHNIHL VCDEIYAATV
ACS4_4043_ID3    ANVKIKGLIL TNPCNPLGTI LDRDTLKKIS TFTNEHNIHL VCDEIYAVTV
ACS4_4222_ID4    ANV*
ACS4_4303_ID5    ANVKIKGLIL TNPCNPLGTI LDRDTLKKIS TFTNEHNIHL VCDEIYAATV
ACS4_4691_ID6    ANVKIKGLIL TNPCNPLGTI LDRDTLKKIS TFTNEHNIHL VCDEIYAATE
ACS4_5251_ID7    ANVKIKGLIL TNPCNPLGTI LDRDTLKKIS TFTNEHNIHL VCDEIYAATV ACS4_WT_ID1      FNSPKFVSIA EIINEDNCIN KDLVHIVSSL SKDLGFPGFR VGIVYSFNDD  300
ACS4_2477_ID2    FNSPKFVSIA EIINEDNCIN KDLVHIVSNL SKDLGFPGFR VGIVYSFNDD
ACS4_4043_ID3    FNSPKFVSIA EIINEDNCIN KDLVHIVSSL SKDLGFPGFR VGIVYSFNDD
ACS4_4222_ID4
ACS4_4303_ID5    FNSPKFVSIA EIINEDNCIN KDLVHIVSSL SKDLGFPGFR VGIVYSFNDD
ACS4_4691_ID6    FNSPKFVSIA EIINEDNCIN KDLVHIVSSL SKDLGFPGFR VGIVYSFNDD
ACS4_5251_ID7    FNSPKFVSIA EIINEDNCIN KDLVHIVSSL SKDLGFPGFR VGIVYSFNDD Small domain
ACS4_WT_ID1      VVNCARKMSS FGLVSTQTQH LLAFMLSDDE FVEEFLIESA KRLRERYEKF  350
ACS4_2477_ID2    VVNCARKMSS FGLVSTQTQH LLAFMLSDDE FVEEFLIESA KRLRERYEKF
ACS4_4043_ID3    VVNCARKMSS FGLVSTQTQH LLAFMLSDDE FVEEFLIESA KRLRERYEKF
ACS4_4222_ID4
ACS4_4303_ID5    VVNCARKMSS FGLVSTQTQH FLAFMLSDDE FVEEFLIESA KRLRERYEKF
ACS4_4691_ID6    VVNCARKMSS FGLVSTQTQH LLAFMLSDDE FVEEFLIESA KRLRERYEKF
ACS4_5251_ID7    VVNCARKMSS FGLVSIQTQH LLAFMLSDDE FVEEFLIESA KRLRERYEKF ACS4_WT_ID1      TRGLEEIGIK CLESNAGVYC WMDLRSLLKE ATLDAEMSLW KLIINEVKLN  400
ACS4_2477_ID2    TRGLEEIGIK CLESNAGVYC WMDLRSLLKE ATLDAEMSLW KLIINEVKLN
```

Figure 5 (continued)

```
ACS4_4043_ID3    TRGLEEIGIK CLESNAGVYC WMDLRSLLKE ATLDAEMSLW KLIINEVKLN
ACS4_4222_ID4
ACS4_4303_ID5    TRGLEEIGIK CLESNAGVYC WMDLRSLLKE ATLDAEMSLW KLIINEVKLN
ACS4_4691_ID6    TRGLEEIGIK CLESNAGVYC WMDLRSLLKE ATLDAEMSLW KLIINEVKLN
ACS4_5251_ID7    TRGLEEIGIK CLESNAGVYC WMDLRSLLKE ATLDAEMSLW KLIINEVKLN

ACS4_WT_ID1      VSPGSSFNCS EVGWFRVCFA NIDDQTMEIA LARIRMFMDA YNNVNKNGVM  450
ACS4_2477_ID2    VSPGSSFNCS EVGWFRVCFA NIDDQTMEIA LARIRMFMDA YNNVNKNGVM
ACS4_4043_ID3    VSPGSSFNCS EVGWFRVCFA NIDDQTMEIA LARIRMFMDA YNNVNKNGVM
ACS4_4222_ID4
ACS4_4303_ID5    VSPGSSFNCS EVGWFRVCFA NIDDQTMEIA LARIRMFMDA YNNVNKNGVM
ACS4_4691_ID6    VSPGSSFNCS EVGWFRVCFA NIDDQTMEIA LARIRMFMDA YNNVNKNGVM
ACS4_5251_ID7    VSPGSSFNCS EVGWFRVCFA NIDDQTMEIA LARIRMFMDA YNNVNKNGVM

ACS4_WT_ID1      KNKHNGRGTT YDLTPQMGST MKMLLA
ACS4_2477_ID2    KNKHNGRGTT YDLTPQMGST MKMLLA
ACS4_4043_ID3    KNKHNGRGTT YDLTPQMGST MKMLLA
ACS4_4222_ID4
ACS4_4303_ID5    KNKHNGRGTT YDLTPQMGST MKMLLA
ACS4_4691_ID6    KNKHNGRGTT YDLTPQMGST MKMLLA
ACS4_5251_ID7    KNKHNGRGTT YDLTPQMGST MKMLLA
```

SOLANUM LYCOPERSICUM PLANTS HAVING NON-TRANSGENIC ALTERATIONS IN THE ACS2 GENE

CROSS-REFERENCE TO RELATED APPLICATIONS

This application is the U.S. National Phase of International Patent Application No. PCT/EP2013/074309, filed Nov. 20, 2013, which claims the benefit to European Application No. 12193592.8, filed Nov. 21, 2012.

FIELD OF THE INVENTION

This invention relates to the field of plant biotechnology and plant breeding. Provided are *Solanum lycopersicum* plants comprising an acs2 allele having one or more mutations, said mutations resulting in production of a mutant acs2 protein having loss-of-function acs2 protein or reduced activity compared to wild type Acs2 protein. The invention provides plants the fruits of which show a lower ethylene production and/or slower fruit ripening and/or a longer shelf life compared to *Solanum lycopersicum* being homozygous for the wild type Acs2 allele. In addition, the invention provides tomato fruit, seeds, pollen, plant parts, and progeny of the *Solanum lycopersicum* plants of the invention. Food and food products comprising or consisting of fruits of the plants of the invention are provided too.

The invention further provides an endogenous acs2 gene and acs2 protein encoded by said gene, having at least one human-induced non-transgenic mutation.

In another embodiment methods for making tomato plants comprising one or more mutant acs2 alleles in their genome are provided herein.

BACKGROUND OF THE INVENTION

Breeding of *Solanum lycopersicum* aims at the production of commercial varieties optimally adapted to growing and storage conditions. A challenge breeders are facing is finding an improved balance between fruit firmness post-harvest and consumer desires in terms of taste, texture and colour. These consumer desires relate strongly to fruit ripening. Fruit ripening is a complex developmental process responsible for the transformation of the seed-containing organ into a tissue attractive to seed dispersers and agricultural consumers. The changes associated with fruit ripening, in particular post-harvest softening, limit the shelf life of fresh tomatoes.

For tomato fruit growth and development, a number of consecutive phases can be discerned: floral development, pollination, then early fruit development takes place which is characterised by a high frequency of cell division and the fruit is rapidly increasing in size mainly due to cell expansion. At the end of the third phase the fruit reaches the mature green stage. During the fourth phase, fruit ripening takes place which is characterised by a change in colour and flavour as well as fruit firmness and texture.

The build-up of the characteristic red colour of the tomato fruit is caused by the accumulation of lycopene and carotene. In general, different colouration phases are distinguished: mature green, breaker, pink and red. At the breaker stage, the typical red pigmentation initiates. Red ripe stage or red ripe harvested fruit stage is the stage where the fruit has reached its mature colour on the major part of the fruit.

In addition to the colour changes, during fruit ripening enzymatic activity leads to degradation of the middle lamellar region of the cell walls which leads to cell loosening which is manifested as softening and loss of texture of the fruit. Softening of the fruit is often measured as external resistance to compression which can be quantified for example by a penetrometer.

Modification of single genes known to be involved in ripening has not yet resulted in a fruit with normal ripening but minimal tissue softening.

Ripening and senescence in climacteric fruits such as tomatoes are promoted by ethylene. Ethylene is autocatalytic for its own biosynthesis through increases in 1-Aminocyclopropae-1-carboxilic acid (ACC) synthase (ACS) and ACC oxidase (ACO). ACS is also referred to as 1-aminocyclopropane-1-carboxylate synthase; Le-ACS; or S-adenosyl-L-methionine methylthioadenosine-lyase. An increase in the amount of ACS and ACO thus leads to an increased conversion of L-methionine into ethylene. At least eight ACS genes (LEACS1A, LEACS1B, and LEACS2-7) have been identified in tomato (Alexander et. al., Journal of Experimental Botany, Vol 53, No 377, pp 2039-2055, 2002) and each ACS has a different expression pattern.

ACC synthase (ACS) is an enzyme that catalyzes the synthesis of 1-aminocyclopropane-1-carboxylic acid (ACC) from S-Adenosyl methionine. ACC is then converted into ethylene catalyzed by ACO. The biosynthesis of ethylene is for example described by Stearns and Glick (Biotechnology Advances 2003, vol 21 pp 193-210), which is enclosed by reference.

ACS belongs to the α-family of pyridoxal-5'-phosphate (PLP) dependent enzymes and shares a modest level of similarity with other members of this family like aspartate amino-transferase (AATase and tyrosine aminotransferase (TATase). The structure of ACS from various sources has been described by Capitani et al. In a sequence alignment of eight ACS proteins (*Malus domestica, Phaseolus aureus, Solanum tuberosum, Pelargonium hortorum, Nicotiana tabacum, Cucumis melo, Lycopersicon esculentum*, and *Brassica oleracea*) they describe conserved regions which are indicated in FIG. 1 in this Capitani publication. (Capitani et al., Journal of Molecular Biology, 1999, vol 294, pp 745-756).

Two systems have been proposed to operate in climacteric plants regulating ethylene production. The first is functional during normal vegetative growth (system 1); it is auto inhibitory and responsible for production of basal ethylene levels that are detected in all tissues including those in non-climacteric plants. System 1 continues during fruit development until a competence to fruit ripening is attained. Then a transition period is reached wherein LEACS1A and LEACS4 are activated resulting in an increased level of ethylene. This increased ethylene level induces the expression of LEACS2 which starts system 2 which is active during the ripening of climacteric fruit. In system 2, ethylene production is auto catalytic. This complexity of the ethylene regulation has been studied using antisense inhibition of LEACS2 in transgenic plants (Barry et al., Plant Physiology vol 123, pp 979-986, 2000).

WO2005/016504 discloses "stay green" plants, i.e. a plant phenotype whereby leaf senescence is delayed compared to a standard reference. It discloses plants with disrupted ACS2, ACS6, ASC7 genes which disruption inhibits the expression or activity of said ACS.

Yokotani et al describe transgenic tomatoes with all known LeEIL genes (Ethylene Insensitive Like genes) suppressed to study the regulatory mechanisms of ethylene biosynthesis (Yokotani et al, Journal of Experimental Botany, vol 60, pp 3433-3442, 2009).

ACS2 mutants are known for instance from Vijee Mohan et al. They disclose (Vijee Mohan et al. Sol 2010, page 67 world wide web at so12010.org/so12010/files/file/SOL2010_Abstracts.pdf) EcoTILLING in tomato wherein nucleotide sequence diversity is used as a measure of the genetic variation that is present in a species, especially Single Nucleotide Polymorphisms (SNPs) are used to represent the most common variations across a genome. EcoTILLING is used as a high throughput, low cost technique for rapid discovery of polymorphisms in natural populations by heteroduplex analysis using a mismatch-specific endonuclease. A collection of tomato accessions was obtained from different sources like NBPGR (India), IIVR (India) and TGRC (California, USA) and were analyzed for the frequency of naturally occurring SNPs, among others in ACS2. A number of SNPs were detected for different genes but with a varying frequency. The morphological features during different developmental stages and chemotypic observations indicated wide variations among the accessions. Correlations between these variations with the location of the SNPs is suggested to be useful in finding promising alleles for crop development.

Studies on transgenic tomato fruit (ACS2 mutants) in which ethylene production was suppressed (Oeller et al, 1991 Science, vol 254, pp 437-439); (Picton et al. 1993 The Plant Journal vol 3 pp 469-481) showed delayed fruit ripening and revealed a critical role of ethylene in fruit ripening.

WO 92/04456 discloses control of plant development characteristics effected by ethylene in tomato and zuchini, among others by recombinant production of ACS and by using antisense technology or mutated ACS genes.

Despite the above, no useful alleles for tomato fruit ripening improvement have been found so far.

There is thus a need for cultivated tomato plants with a modified ethylene production having a delayed ripening and/or longer shelf-life of the tomato fruits compared to wild type tomato plants.

SUMMARY OF THE INVENTION

It is, thus, an object of the invention to generate and identify cultivated plants of the species *Solanum lycopersicum* having fruits that have delayed ripening and/or a longer shelf-life of the fruits.

The invention thus relates to a cultivated plant of the species *Solanum lycopersicum* comprising an acs2 allele having one or more mutations, said mutations resulting in production of a mutant acs2 protein, wherein said mutant acs2 protein has one or more amino acids changed selected from the group consisting of A101T, A101V, A103T, G112R, P118L, V147E, and C265Y of SEQ ID NO: 1 or in a wild type Acs2 protein having at least 85% amino acid sequence identity to SEQ ID NO: 1, i.e. in a variant of SEQ ID NO: 1 (as defined below).

In one embodiment the invention relates to a plant of the invention wherein said mutation results in production of a mutant acs2 protein having loss-of-function acs2 protein or reduced function compared to wild type Acs2 protein, wherein said wild type acs2 protein is a protein having at least 85% amino acid sequence identity to SEQ ID NO: 1 and wherein said mutant acs2 protein comprises sufficient function to result in ripening of the tomato fruits to the red stage when the mutant allele is present in heterozygous or homozygous form.

GENERAL DEFINITIONS

The term "nucleic acid sequence" (or nucleic acid molecule) refers to a DNA or RNA molecule in single or double stranded form, particularly a DNA encoding a protein or protein fragment according to the invention. An "isolated nucleic acid sequence" refers to a nucleic acid sequence which is no longer in the natural environment from which it was isolated, e.g. the nucleic acid sequence in a bacterial host cell or in the plant nuclear or plastid genome.

The terms "protein" or "polypeptide" are used interchangeably and refer to molecules consisting of a chain of amino acids, without reference to a specific mode of action, size, 3-dimensional structure or origin. A "fragment" or "portion" of Acs2 protein may thus still be referred to as a "protein". An "isolated protein" is used to refer to a protein which is no longer in its natural environment, for example in vitro or in a recombinant bacterial or plant host cell.

The term "gene" means a DNA sequence comprising a region (transcribed region), which is transcribed into an RNA molecule (e.g. an mRNA, hpRNA or an RNAi molecule) in a cell, operably linked to suitable regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sites. A gene may be an endogenous gene (in the species of origin) or a chimeric gene (e.g. a transgene or cis-gene).

"Expression of a gene" refers to the process wherein a DNA region, which is operably linked to appropriate regulatory regions, particularly a promoter, is transcribed into an RNA, which is biologically active, i.e. which is capable of being translated into a biologically active protein or peptide (or active peptide fragment) or which is active itself (e.g. in posttranscriptional gene silencing or RNAi). The coding sequence may be in sense-orientation and encodes a desired, biologically active protein or peptide, or an active peptide fragment.

An "active protein" or "functional protein" is a protein which has protein activity as measurable in vitro, e.g. by an in vitro activity assay, and/or in vivo, e.g. by the phenotype conferred by the protein. A "wild type" protein is a fully functional protein comprising at least 85% amino acid sequence identity to SEQ ID NO: 1 (also referred to as variant of SEQ ID NO:1). Likewise, the wild type Acs2 allele is the allele encoding said wild type protein or variant. A "mutant protein" is herein a protein comprising one or more mutations in the nucleic acid sequence encoding the protein, whereby the mutation results in (the mutant nucleic acid molecule encoding) a "reduced-function" or "loss-of-function" protein, as e.g. measurable in vivo, e.g. by the phenotype conferred by the mutant allele.

A "reduced function acs2 protein" or "reduced activity acs2 protein" refers to a mutant acs2 protein which has a reduced catalytic activity in synthesizing ACC from S-Adenosyl methionine, leading to reduced ethylene synthesis compared to wild-type Acs2 protein. Said reduced catalytic activity of the acs2 protein affects the ripening behaviour of the fruits comprising such reduced function acs2 protein when the allele encoding the mutant protein is present in homozygous or heterozygous form in the tomato plant, i.e. delayed ripening and/or longer shelf-life of the fruits. Such a reduced function acs2 protein can be obtained by the transcription and translation of a "partial knockout mutant acs2 allele" which is, for example, a wild-type Acs2 allele, which comprises one or more mutations in its nucleic acid sequence. In one aspect, such a partial knockout mutant acs2 allele is a wild-type Acs2 allele, which comprises one or more mutations that preferably result in the production of an acs2 protein wherein at least one conserved and/or functional amino acid is substituted for another amino acid, such that the biological activity is significantly reduced but not completely abolished. However, other mutations, such as one or more non-sense, missense, splice-site or frameshift mutations in the tomato Acs2 allele may also result in reduced function acs2 protein and such reduced function proteins may have one or more amino acids replaced, inserted or deleted, relative to the wild type ACS2 protein. Such partial knockout mutant acs2 allele may also encode a dominant negative acs2 protein, which is capable of adversely affecting the biological activity of other Acs2 proteins within the same cell. Such a dominant negative acs2 protein can be an Acs2 protein that is still capable of interacting with the same elements as the wild-type Acs2 protein, but that blocks some aspect of its function. Examples of dominant negative Acs2 proteins are acs2 proteins that lack, or have modifications in specific amino acid residues critical for activation and/or dimerization, but still contain their binding domain, such that not only their own biological activity is reduced or abolished, but that they further reduce the total acs2 activity in the cell by competing with wild type and/or partial knockout acs2 proteins present in the cell for binding sites. Mutant alleles can be either "natural mutant" alleles, which are mutant alleles found in nature (e.g. produced spontaneously without human application of mutagens) or "induced mutant" alleles, which are induced by human intervention, e.g. by mutagenesis.

A "loss-of-function Acs2 protein" refers to a mutant Acs2 protein which is has essentially no catalytic activity in synthesising ACC from S-Adenosyl methionine compared to wild-type Acs2 protein, leading to reduced ethylene synthesis compared to wild type Acs2 protein. Said lack of catalytic activity synthesis affects the ripening behaviour of the fruits comprising such loss-of-function acs2 protein when the allele encoding the mutant protein is present in homozygous or heterozygous form in the tomato plant. Fruits of tomato plants homozygous for such a "loss-of-function acs2 protein" may still produce ethylene catalysed by other proteins (e.g. other Acs proteins like Acs1A or Acs4). As a consequence, fruits of tomato plants homozygous for such a "loss-of-function acs2 protein" may still ripen, but ripening may be delayed and/or shelf life may be longer.

A "mutation" in a nucleic acid molecule coding for a protein is a change of one or more nucleotides compared to the wild type sequence, e.g. by replacement, deletion or insertion of one or more nucleotides. A "point mutation" is the replacement of a single nucleotide, or the insertion or deletion of a single nucleotide.

A "nonsense" mutation is a (point) mutation in a nucleic acid sequence encoding a protein, whereby a codon is changed into a stop codon. This results in a premature stop codon being present in the mRNA and in a truncated protein. A truncated protein may have reduced function or loss of function.

A "missense" or non-synonymous mutation is a (point) mutation in a nucleic acid sequence encoding a protein, whereby a codon is changed to code for a different amino acid. The resulting protein may have reduced function or loss of function.

A "splice-site" mutation is a mutation in a nucleic acid sequence encoding a protein, whereby RNA splicing of the pre-mRNA is changed, resulting in an mRNA having a different nucleotide sequence and a protein having a different amino acid sequence than the wild type. The resulting protein may have reduced function or loss of function.

A "frame-shift" mutation is a mutation in a nucleic acid sequence encoding a protein by which the reading frame of the mRNA is changed, resulting in a different amino acid sequence. The resulting protein may have reduced function or loss of function.

A mutation in a regulatory sequence, e.g. in a promoter of a gene, is a change of one or more nucleotides compared to the wild type sequence, e.g. by replacement, deletion or insertion of one or more nucleotides, leading for example to reduced or no mRNA transcript of the gene being made.

"Silencing" refers to a down-regulation or complete inhibition of gene expression of the target gene or gene family.

A "target gene" in gene silencing approaches is the gene or gene family (or one or more specific alleles of the gene) of which the endogenous gene expression is down-regulated or completely inhibited (silenced) when a chimeric silencing gene (or 'chimeric RNAi gene') is expressed and for example produces a silencing RNA transcript (e.g. a dsRNA or hairpin RNA capable of silencing the endogenous target gene expression). In mutagenesis approaches, a target gene is the endogenous gene which is to be mutated, leading to a change in (reduction or loss of) gene expression or a change in (reduction or loss of) function of the encoded protein.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous and, where necessary to join two protein encoding regions, contiguous and in reading frame so as to produce a "chimeric protein". A "chimeric protein" or "hybrid protein" is a protein composed of various protein "domains" (or motifs) which is not found as such in nature but which a joined to form a functional protein, which displays the functionality of the joined domains. A chimeric protein may also be a fusion protein of two or more proteins occurring in nature.

The term "food" is any substance consumed to provide nutritional support for the body. It is usually of plant or animal origin, and contains essential nutrients, such as carbohydrates, fats, proteins, vitamins, or minerals. The substance is ingested by an organism and assimilated by the organism's cells in an effort to produce energy, maintain life, or stimulate growth. The term food includes both substance consumed to provide nutritional support for the human and animal body.

The term "shelf life" or "post-harvest shelf life" designates the (average) length of time that a fruit is given before it is considered unsuitable for sale or consumption ('bad' or 'bad stage'). Shelf life is the period of time that products can be stored, during which the defined quality of a specified proportion of the goods remains acceptable under expected conditions of distribution, storage and display. Shelf life is influenced by several factors: exposure to light and heat, transmission of gases (including humidity), mechanical stresses, and contamination by things such as micro-organisms. Product quality is often mathematically modelled around the fruit firmness/softness parameter. Shelf-life can be defined as the (average) time it takes for fruits of a plant line to start to become bad and unsuitable for sale or consumption, starting for example from the first fruit of a plant entering breaker stage or turning stage or from the first fruit becoming fully red or from harvest. In one embodiment the mutants according to the invention have a shelf life that is significantly longer than the shelf life of wild type plants, for example the number of days from the first fruit being in breaker stage (or turning stage, pink stage, red stage or from harvest) up to the first fruit starting to become 'bad' and unsuitable for sale or consumption is significantly longer, e.g. at least 1, 2, 3, 4, 5, 6, 7, 8, 9, 10, or more, days longer than fruits of control plants (such as wild type Acs2/Acs2 plants), when plants are grown under the same conditions and fruits are treated the same way and kept under the same conditions. Thus, to determine the number of days required from a certain stage (e.g. from breaker stage or a later stage) to 'bad' stage, the day when the first fruit of the wild type control plant (grown under the same conditions as the mutant plants and being at the same developmental stage) enters a certain stage (e.g. breaker stage or a later stage) can, for example, be taken as the starting point (day 1) from when on periodically (at certain time intervals, e.g. after 1, 2, 3, 4, 5 or 6 days) the fruits are observed until the day that the first fruit has passed the fully ripe stage and becomes 'bad' (as determinable visually and/or through assessing fruit softness).

In this application the words "improved", "increased", "longer" and "extended" as used in conjunction with the word "shelf-life" are interchangeable and all mean that the fruits of a tomato plant according to the invention have on average, a longer shelf-life than the control fruits (Acs2/Acs2 fruits) such as Pusa Sheetal, Tapa, or TPAADASU.

"Delayed ripening" means that the fruits of a tomato plant or plant line (e.g. a mutant) according to the invention require on average significantly more days to reach the red stage from the mature green, breaker, turning stage, and/or pink stages of tomato fruit ripening compared to wild type control fruits of plants homozygous for the wild type Acs2 allele (Acs2/Acs2). Delayed ripening can be measured on the plant and/or after harvest as days required for a certain percentage of fruits (e.g. 10%, 20%, 30%, 40%, 50%, 60%, 70%, 80%, 90% and/or 100% of fruits) to reach the red stage. A plant is said to have a delayed ripening phenotype if it takes at least 2, 3, 4, 5, 6, 7, 8, 9, 10, 11, 12, 13, 14 or 15 days longer for 10%, 20%, 30% 40%, 50%, 60%, 70%, 80%, 90% and/or 100% of fruits to reach the red stage than it takes for the wild type control fruits to develop the same percentage of red fruits. It is understood that each combination of above-cited number of days (i.e. 2, 3, 4, 5, 6, 7, 8, 9, 10, 11, 12, 13, 14 or 15) with each % of fruits to reach the red stage (i.e. 10%, 20%, 30% 40%, 50%, 60%, 70%, 80%, 90% and/or 100%) is enclosed herein, both for the delayed ripening to be measured on the plant and after harvest. For example if it takes at least 2 days longer for 10%, 20%, 30% 40%, 50%, 60%, 70%, 80%, 90% and/or 100% of fruits to reach the red stage than it takes for the wild type control fruits to develop the same percentage of red fruits. Another example of how delayed ripening can be measured on the plant and/or after harvest is it takes at least 2, 3, 4, 5, 6, 7, 8, 9, 10, 11, 12, 13, 14 or 15 days longer for 100% of fruits to reach the red stage than it takes for the wild type control fruits to develop the same percentage of red fruits. The day when the first fruit of the wild type control plant (grown under the same conditions as the mutant plants and being at the same developmental stage) enters a certain stage (e.g. breaker stage) can, for example, be taken as the starting point (day 1) from when on periodically (at certain time intervals, e.g. after 1, 2, 3, 4, 5 or 6 days) the number of fruits that are in breaker stage and the number of fruit that are in red stage are counted, both for the mutant plant line and control plants (see Examples).

In this application the word senescence means biological aging i.e. the change in the biology of an organism as it ages after its maturity.

As used herein, "reduced ethylene production" refers herein to statistically significant reduced amounts of ethylene being produced by tomato fruits according to the invention (compared to wild type Acs2/Acs2 fruits) during fruit ripening, e.g. at the pink stage and/or at the light red stage and/or at the red stage, as described in the Examples, and as measurable by real time ethylene measurements. In one embodiment, ethylene levels are significantly reduced throughout fruit ripening from pink stage through to red stage.

It is understood that comparisons between different plant lines involves growing a number of plants of a line (e.g. at least 5 plants, preferably at least 10 plants per line) under the same conditions as the plants of one or more control plant lines (preferably wild type plants) and the determination of statistically significant differences between the plant lines when grown under the same environmental conditions.

"Delay of breaker stage" refers to the mutants according to the invention requiring significantly more days than wild type controls for the first fruits and/or for all fruits to have entered breaker stage, e.g. at least 1 more day, preferably at least 2, 3, 4, 5, 6, 7, 8, 9, 10, 11 or 12 more days than the wild type control, when grown under the same conditions.

The "ripening stage" of a tomato fruit can be divided as follows: (1) Mature green stage: surface is completely green; the shade of green may vary from light to dark. (2) Breaker stage: there is a definite break in color from green to tannish-yellow, pink or red on not more than 10% of the surface; (3) Turning stage: 10% to 30% of the surface is not green; in the aggregate, shows a definite change from green to tannish-yellow, pink, red, or a combination thereof. (4) Pink stage: 30% to 60% of the surface is not green; in the aggregate, shows pink or red color. (5) Light red stage: 60% to 90% of the surface is not green; in the aggregate, shows pinkish-red or red. (6) Red stage: More than 90% of the surface is not green; in the aggregate, shows red color.

"Sequence identity" and "sequence similarity" can be determined by alignment of two peptide or two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximizing the number of matches and minimises the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff & Henikoff, 1992, PNAS 89, 1091510919). Sequence alignments and scores for percentage sequence identity may for example be determined using computer programs, such as EMBOSS (world wide web at ebLac.uk/Tools/psa/emboss_needle/). Alternatively sequence similarity or identity may be determined by searching against databases such as FASTA, BLAST, etc., but hits should be retrieved and aligned pairwise to compare sequence identity. Two proteins or two protein domains, or two nucleic acid sequences have "substantial sequence identity" if the percentage sequence identity is at least 85%, 90%, 95%, 98%, 99% or more (e.g. at least 99.1, 99.2 99.3 99.4, 99.5, 99.6, 99.7, 99.8, 99.9 or more (as determined by Emboss "needle" using default parameters, i.e. gap creation penalty =10, gap extension penalty =0.5, using scoring matrix DNAFULL for nucleic acids an Blosum62 for proteins).

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one". It is further understood that, when referring to "sequences" herein, generally the actual physical molecules with a certain sequence of subunits (e.g. amino acids) are referred to.

As used herein, the term "plant" includes the whole plant or any parts or derivatives thereof, such as plant organs (e.g., harvested or non-harvested fruits, flowers, leaves, etc.), plant cells, plant protoplasts, plant cell or tissue cultures from which whole plants can be regenerated, regenerable or non-regenerable plant cells, plant calli, plant cell clumps, and plant cells that are intact in plants, or parts of plants, such as embryos, pollen, ovules, ovaries, fruits (e.g., harvested tissues or organs, such as harvested tomatoes or parts thereof), flowers, leaves, seeds, tubers, clonally propagated plants, roots, stems, cotyledons, hypocotyls, root tips and the like. Also any developmental stage is included, such as seedlings, immature and mature, etc.

A "plant line" or "breeding line" refers to a plant and its progeny. As used herein, the term "inbred line" refers to a plant line which has been repeatedly selfed.

"Plant variety" is a group of plants within the same botanical taxon of the lowest grade known, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of 1 locus or gene (or a series of phenotypical characteristics due to this single locus or gene), but which can otherwise differ from one another enormously as regards the other loci or genes.

"F1, F2, etc." refers to the consecutive related generations following a cross between two parent plants or parent lines. The plants grown from the seeds produced by crossing two plants or lines is called the F1 generation. Selling the F1 plants results in the F2 generation, etc. "F1 hybrid" plant (or F1 seed) is the generation obtained from crossing two inbred parent lines. An "M1 population" is a plurality of mutagenized seeds/plants of a certain plant line or cultivar. "M2, M3, M4, etc." refers to the consecutive generations obtained following selling of a first mutagenized seed/plant (M1).

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

The term "locus" (loci plural) means a specific place or places or a site on a chromosome where for example a gene or genetic marker is found. The ACS2 locus is thus the location in the genome where the ACS2 gene is found.

"Wild type allele" (WT or Wt) refers herein to a version of a gene encoding a fully functional protein (wild type protein). Such a sequence encoding a fully functional Acs2 protein is for example the wild type Acs2 eDNA (mRNA) sequence depicted in SEQ ID NO: 9, based on GenBank NM001247249.1 Tomato 1-aminocyclopropane-1-carboxylate synthase mRNA, complete cds world wide web at ncbi.nlm.nih.gov/nuccore/NM 001247249.1 or world wide web at ncbi.nlm.nih.gov/nuccore/AY326958.1. or the wild type Acs2 genomic sequence depicted in SEQ ID NO: 17. The protein sequence encoded by this wild type Acs2 mRNA is depicted in SEQ ID NO: 1. It consists of 485 amino acids. Other fully functional Acs2 protein encoding alleles (i.e. alleles which confer ripening and ethylene production to the same extent as the protein of SEQ ID NO 1) may exist in other *Solanum lycopersicum* plants and may comprise substantial sequence identity with SEQ ID NO: 1, i.e. at least about 85%, 90%, 95%, 98%, 99%, 99.2%, 99.3%, 99.4%, 99.5%, 99.6%, 99.7% sequence identity with SEQ ID NO: 1. Such fully functional wild type Acs2 proteins are herein referred to as "variants" of SEQ ID NO: 1. Likewise the nucleotide sequences encoding such fully functional Acs2 proteins are referred to as variants of SEQ ID NO: 9 and SEQ ID NO: 17.

The following mutant acs2 alleles are exemplary of the reduced ethylene production and/or delayed-ripening and/or extended shelf-life conferring acs2 mutations identified according to the present invention. It is noted that nucleotide sequences referred to herein (SEQ ID NO: 9-16) are cDNA, i.e. coding DNA sequences, encoding the proteins of SEQ ID NO: 1-8. Obviously, when reference is made to these cDNA nucleotide sequences, it is understood that the cDNA is the coding region of the corresponding *Solanum lycopersicum* genomic acs2 sequence, which, however, additionally contains introns and therefore the nucleotides have different numbering. Thus, when reference is made to a tomato plant comprising an acs2 sequence according to e.g. any one of SEQ ID NO: 9-16, it is, therefore, understood that the tomato plant comprising the genomic acs2 sequence which comprises the coding DNA (cDNA), from which the mRNA of SEQ ID NO: 8-14 is transcribed (and which is in turn translated into protein). The mRNA has the same nucleotide sequence as the cDNA, except that Thymine (T) is Uracil (U) in the mRNA. Further, when reference is made to a tomato plant comprising a nucleotide sequence encoding a protein according to the invention (i.e. a mutant protein of SEQ ID No: 2, 3, 4, 5, 6, 7, or 8), this encompasses different nucleotide sequences, due to the degeneracy of the genetic code. In one embodiment the plant comprises the genomic Acs2 sequence depicted in SEQ ID NO:17 or a genomic Acs2 sequence substantially identical thereto (e.g. having at least about 70%, 75%, 80%, 85%, 90%, 95%, 98%, 99%, 99.2%, 99.3%, 99.4%, 99.5%, 99.6%, 99.7% sequence identity with SEQ ID NO: 17), but with one or more mutations in said sequence, especially in the exons of said genomic sequence (exon 1 ranges from nucleotide 1 to 171; exon 2 ranges from nucleotide 270 to 399, exon 3 ranges from nucleotide 485 to 644 and exon 4 ranges from nucleotide 1526 to 2523; counting A in the ATG of the START CODON as nucleotide position 1), causing reduced function or loss of function of the encoded mutant acs2 protein.

One exemplary mutant acs2 allele (mutant 783) conferring reduced ethylene production and/or delayed ripening and/or extended shelf-life, identified according to the present invention, comprises a mutation resulting in an alanine (Ala or A) to threonine (Thr or T) substitution at amino acid 103 (A103T) in the encoded protein. The protein sequence of mutant 783 is depicted in SEQ ID NO: 2. The amino acid substitution is due to a G to A mutation at nucleotide 307 of SEQ ID NO: 9 counting A in the ATG of the START CODON as nucleotide position 1. The mutant cDNA of mutant 783 is depicted in SEQ ID NO: 10.

Yet another exemplary mutant acs2 allele (mutant 2145) conferring reduced ethylene production and/or delayed ripening and/or extended shelf-life, identified according to the present invention, comprises a mutation resulting in a glycine (Gly or G) to arginine (Arg or R) substitution at amino acid 112 (G112R) in the encoded protein. The protein sequence of mutant 2145 is depicted in SEQ ID NO: 3. The amino acid substitution is due to a change from G to A at nucleotide 334 as shown in SEQ ID NO: 9 counting A in the ATG of the START CODON as nucleotide position 1. The mutant cDNA of mutant 2145 is depicted in SEQ ID NO: 11.

Another exemplary mutant acs2 allele (mutant 2714) conferring reduced ethylene production and/or delayed ripening and/or extended shelf-life, identified according to the present invention, comprises a mutation resulting in a change from a proline (Pro or P) to leucine (Leu or L) at amino acid 118 (P118L) in the encoded protein (SEQ ID NO: 4). The protein sequence of mutant 2714 is depicted in SEQ ID NO: 4. The amino acid substitution is due to a C to T mutation at nucleotide 353 (C353T) of SEQ ID NO: 9, counting A in the ATG of the START CODON as nucleotide position 1. The mutant cDNA 2714 is depicted in SEQ ID NO: 12.

Still another exemplary mutant acs2 allele (mutant 3793) conferring reduced ethylene production and/or delayed ripening and/or extended shelf-life, identified according to the present invention, comprises a mutation resulting in a change from a alanine (Ala or A) to valine (Val or V) at amino acid 101 (A101V) in the encoded protein (SEQ ID NO: 5). The amino acid substitution is due to a C to T mutation at nucleotide 302 (C302T) of SEQ ID NO: 9, counting A in the ATG of the START CODON as nucleotide position 1. The mutant cDNA is depicted in SEQ ID NO: 13.

Another exemplary mutant acs2 allele (mutant 4946) conferring reduced ethylene production and/or delayed ripening and/or extended shelf-life, identified according to the present invention, comprises a mutation resulting in a change from alanine (Ala or A) to threonine (Thr or T) at amino acid 101 (A101T) in the encoded protein (SEQ ID NO: 6). The amino acid substitution is due to a change from G to A at nucleotide 301 (G301A) of SEQ ID NO: 9, counting A in the ATG of the START CODON as nucleotide position 1. The mutant cDNA is depicted in SEQ ID NO: 14.

Yet another exemplary mutant acs2 allele (mutant 7871) conferring reduced ethylene production and/or delayed ripening and/or extended shelf-life, identified according to the present invention, comprises a mutation resulting in a change from a cysteine (Cys or C) to tyrosine (Tyr or Y) at amino acid 265 (C265Y) in the encoded protein (SEQ ID NO: 7). The amino acid substitution is due to a G to A mutation at nucleotide 794 (G794A) of SEQ ID NO: 9, counting A in the ATG of the START CODON as nucleotide position 1. The mutant cDNA is depicted in SEQ ID NO: 15.

Another exemplary mutant acs2 allele (mutant 8185) conferring reduced ethylene production and/or delayed ripening and/or extended shelf-life, identified according to the present invention, comprises a mutation resulting in a change from valine (Val or V) to glutamic acid (Glu or E) at amino acid 147 (V147E) in the encoded protein (SEQ ID NO: 8). The amino acid substitution is due to a change from T to A at nucleotide 440 (T440A) of SEQ ID NO: 9, counting A in the ATG of the START CODON as nucleotide position 1. The mutant cDNA is depicted in SEQ ID NO: 16.

"Mutant allele" refers herein to an allele comprising one or more mutations in the coding sequence (mRNA, cDNA or genomic sequence) compared to the wild type allele. Such mutation(s) (e.g. insertion, inversion, deletion and/or replacement of one or more nucleotide(s)) may lead to the encoded protein having reduced in vitro and/or in vivo functionality (reduced function) or no in vitro and/or in vivo functionality (loss-of-function), e.g. due to the protein e.g. being truncated or having an amino acid sequence wherein one or more amino acids are deleted, inserted or replaced. Such changes may lead to the protein having a different 3D conformation, being targeted to a different sub-cellular compartment, having a modified catalytic domain, having a modified binding activity to nucleic acids or proteins, etc.

"Wild type plant" and "wild type fruits" or "normal ripening" plants/fruits refers herein to a tomato plant comprising two copies of a wild type (WT or Wt) Acs2 allele (Acs2/Acs2) encoding a fully functional Acs2 protein (e.g. in contrast to "mutant plants", comprising a mutant acs2 allele). Such plants are for example suitable controls in phenotypic assays. Preferably wild type and/or mutant plants are "cultivated tomato plants". For example the cultivar Moneymaker is a wild type plant, as is cultivar Ailsa Craig, cultivar Tapa and many others.

"Tomato plants" or "cultivated tomato plants" are plants of the *Solanum lycopersicum*, i.e. varieties, breeding lines or cultivars of the species *Solanum lycopersicum*, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of a species. The so-called heirloom varieties or cultivars, i.e. open pollinated varieties or cultivars commonly grown during earlier periods in human history and often adapted to specific geographic regions, are in one aspect of the invention encompassed herein as cultivated tomato plants.

Wild relatives of tomato include *S. arcanum, S. chmielewskii, S. neorickii (=L. parviflorum), S. cheesmaniae, S. galapagense, S. pimpinellifolium, S. chilense, S. corneliomulleri, S. habrochaites (=L. hirsutum), S. huaylasense, S. sisymbriifolium, S. peruvianum, S. hirsutum* or *S. pennellii*.

"Average" refers herein to the arithmetic mean.

BRIEF DESCRIPTION OF THE SEQUENCE LISTING

SEQ ID NO: 1 shows the *Solarium lycopersicum* wild type, fully functional, ACS2 protein sequence as derived from the mRNA based on NCBI Reference Sequence: NM_001247249.1; world wide web at ncbi.nlm.nih.gov/nuccore/NM 001247249.

SEQ ID NO: 2 shows the *Solarium lycopersicum* mutant 783 acs2 protein sequence.

SEQ ID NO: 3 shows the *Solarium lycopersicum* mutant 2145 acs2 protein sequence.

SEQ ID NO: 4 shows the *Solanum lycopersicum* mutant 2714 acs2 protein sequence.

SEQ ID NO: 5 shows the *Solanum lycopersicum* mutant 3793 acs2 protein sequence.

SEQ ID NO: 6 shows the *Solanum lycopersicum* mutant 4946 acs2 protein sequence.

SEQ ID NO: 7 shows the *Solanum lycopersicum* mutant 7871 acs2 protein sequence.

SEQ ID NO: 8 shows the *Solanum lycopersicum* mutant 8185 acs2 protein sequence.

SEQ ID NO: 9 shows the *Solanum lycopersicum* wild type Acs2 cDNA based on NCBI Reference Sequence: N_001247249.1 (world wide web at ncbi.nlm.nih.gov/nuccore/NM_001247249) for *Solanum lycopersicum* ripening-related ACC synthase 2 (ACS2), mRNA.

SEQ ID NO: 10 shows the *Solarium lycopersicum* mutant 783 acs2 cDNA.

SEQ ID NO: 11 shows the *Solarium lycopersicum* mutant 2145 acs2 cDNA.

SEQ ID NO: 12 shows the *Solarium lycopersicum* mutant 2714 acs2 cDNA.

SEQ ID NO: 13 shows the *Solanum lycopersicum* mutant 3793 acs2 cDNA.

SEQ ID NO: 14 shows the *Solanum lycopersicum* mutant 4946 acs2 cDNA.

SEQ ID NO: 15 shows the *Solanum lycopersicum* mutant 7871 acs2 cDNA.

SEQ ID NO: 16 shows the *Solanum lycopersicum* mutant 8185 acs2 cDNA.

SEQ ID NO: 17 shows the *Solanum lycopersicum* wild type Acs2 genomic DNA as obtained from the solgenomics network (world wide web at solgenomics.net sequence region s12.40ch01:78217541-78213542). The position of the exons as described herein, is derived from this sequence.

SEQ ID NO: 18 shows amino acids 58 to and including 154 of the *Solanum lycopersicum* mutant 783 acs2 protein sequence as shown in SEQ ID NO: 2.

SEQ ID NO: 19 shows amino acids 58 to and including 154 of the *Solanum lycopersicum* mutant 2145 acs2 protein sequence as shown in SEQ ID NO: 3.

SEQ ID NO: 20 shows amino acids 58 to and including 154 of the *Solanum lycopersicum* mutant 2714 acs2 protein sequence as shown in SEQ ID NO: 4.

SEQ ID NO: 21 shows amino acids 58 to and including 154 of the *Solanum lycopersicum* mutant 3793 acs2 protein sequence as shown in SEQ ID NO: 5.

SEQ ID NO: 22 shows amino acids 58 to and including 154 of the *Solanum lycopersicum* mutant 4946 acs2 protein sequence as shown in SEQ ID NO: 6.

SEQ ID NO: 23 shows amino acids 184 to and including 297 of the *Solarium lycopersicum* mutant 7871 acs2 protein sequence as shown in SEQ ID NO: 7.

SEQ ID NO: 24 shows amino acids 58 to and including 154 of the *Solanum lycopersicum* mutant 8185 acs2 protein sequence as shown in SEQ ID NO: 8.

SEQ ID NO: 25 shows the *Solanum lycopersicum* wild type, fully functional, ACS4protein sequence as derived from the mRNA based on Genbank Accession number AAA34131.1 (encoded by the cDNA of GenBank Accession number M63490.1).

SEQ ID NO: 26 shows the *Solanum lycopersicum* mutant 2477 acs4 protein sequence.

SEQ ID NO: 27 shows the *Solanum lycopersicum* mutant 4043 acs4 protein sequence.

SEQ ID NO: 28 shows the *Solanum lycopersicum* mutant 4222 acs4 protein sequence.

SEQ ID NO: 29 shows the *Solanum lycopersicum* mutant 4303 acs4 protein sequence.

SEQ ID NO: 30 shows the *Solanum lycopersicum* mutant 4691 acs4 protein sequence.

SEQ ID NO: 31 shows the *Solanum lycopersicum* mutant 5251 acs4 protein sequence.

BRIEF DESCRIPTION OF THE FIGURES

FIG. 3: Alignment of SEQ ID NO: 1-8. The mutations are depicted in bold and underlined.

FIG. 5: Alignment of amino acid sequence of wild type Acs4 amino acid sequence (ACS4 WT ID1, equal to SEQ ID NO: 25) with six acs4 mutants: mutant 2477 (ACS4 2477 ID2, equal to SEQ ID NO: 26), mutant 4043 (ACS4 4043 ID3, equal to SEQ ID NO: 27), mutant 4222 (ACS4 4222 ID4, equal to SEQ ID NO: 28), mutant 4303 (ACS4 4303 IDS, equal to SEQ ID NO: 29), mutant 4691 (ACS4 4691 ID6, equal to SEQ ID NO: 30), and mutant 5251 (ACS4 5251 ID7, equal to SEQ ID NO: 31). Acs4 small and large domains are also depicted (light gray), as are the mutations (in bold and underlined).

DETAILED DESCRIPTION OF THE INVENTION

Figure 1:
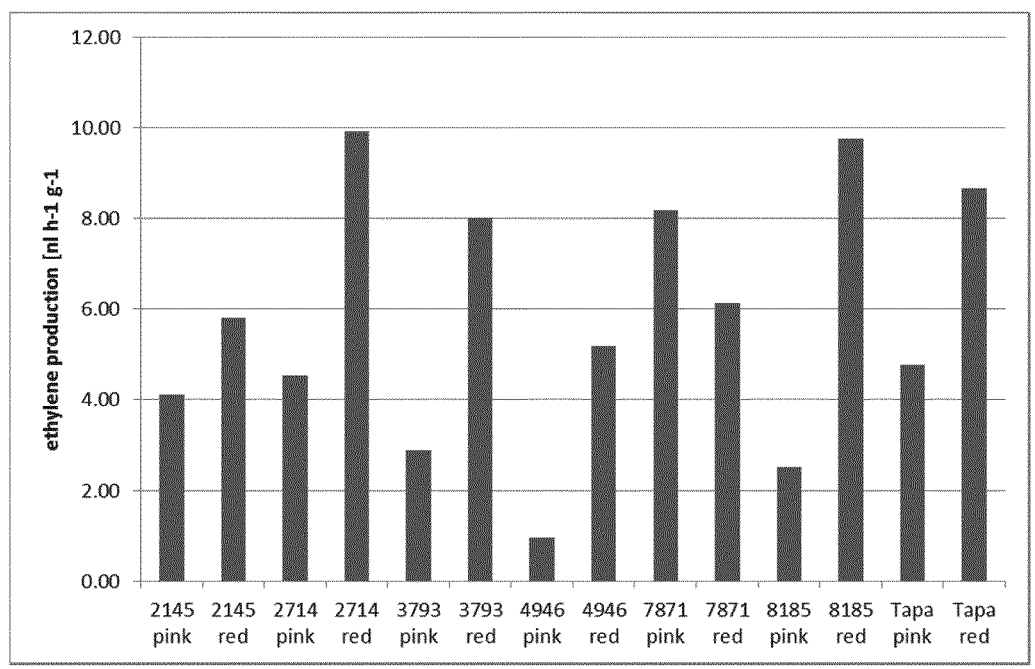
FIG. 1: Ethylene-release measured in nl/(h·g), also written as nl·h$^{-1}$·g$^{-}$, from tomato fruits of various acs2 mutants at Pink stage and Red stage. Tapa is a type (Acs2/Acs2) plant.

The present invention discloses a cultivated plant of the species *Solanum lycopersicum* comprising an acs2 allele having one or more mutations, said mutations resulting in production of a mutant acs2 protein having loss-of-function and/or reduced function compared to wild type Acs2 protein.

In one aspect the invention relates to a cultivated plant of the species *Solanum lycopersicum*, and/or parts thereof (e.g. fruits), comprising an acs2 allele having one or more mutations, said mutations resulting in production of a mutant acs2 protein having loss-of-function or reduced function compared to wild type Acs2 protein wherein said mutation or mutations result in reduced ethylene production and/or delayed fruit ripening and/or a longer shelf life compared to *Solanum lycopersicum* plants which are homozygous for the wild type fully functional Acs2 allele (Acs2/Acs2) (encoding a functional Acs2 protein of SEQ ID NO: 1 or a functional variant).

A *S. lycopersicum* plant encoding the protein of SEQ ID NO: 1 is for example described by Kamiyoshihara Y, et al. in Plant J. 2010 Vol 64(1) pp 140-50; Turnover of LeACS2, a wound-inducible 1-aminocyclopropane-1-carboxylic acid synthase in tomato, is regulated by phosphorylation/dephosphorylation.

In one aspect the invention relates to a cultivated plant of the species *Solanum lycopersicum* and/or parts thereof (e.g. fruit or seed) comprising an acs2 allele having one or more mutations, said mutations resulting in production of a mutant acs2 protein, wherein said mutant acs2 protein has one or more amino acids changed selected from the group consisting of A101T, A101V, A103T, G112R, P118L, V147E, and C265Y in the wild type Acs2 protein of SEQ ID NO: 1 or in a functional variant thereof. Which functional variant is a wild type Acs2 protein having at least 85% sequence identity to SEQ ID NO: 1; and optionally wherein said mutation results in production of a mutant acs2 protein having loss-of-function or reduced function compared to wild type Acs2 protein.

In another aspect the invention relates to a plant of the invention wherein said mutant acs2 protein comprises amino acids 58 to and including 154 and/or amino acids 184 to and including 297 or SEQ ID NO: 1 and wherein said mutant acs2 protein has one or more amino acids changed selected from the group consisting of A101T, A101V, A103T, G112R, P118L, V147E, and C265Y of SEQ ID NO: 1.

In yet another aspect the invention relates to a cultivated plant of the species *Solarium lycopersicum* and/or parts thereof (e.g. fruit or seed) comprising an acs2 allele having one or more mutations, wherein said mutant acs2 protein encoded by said allele, has one or more amino acids changed selected from the group consisting of A101T, A101V, A103T, G112R, P118L, V147E, and C265Y of SEQ ID NO:1 or of a wild type variant of SEQ ID NO: 1 having at least 85% amino acid sequence identity to SEQ ID NO:1.

In a further aspect the invention relates to a mutant acs2 protein having one or more amino acids changed selected from the group consisting of A101T, A101V, A103T, G112R, P118L, V147E, and C265Y of SEQ ID NO:1 or of a wild type variant of SEQ ID NO: 1 having at least 85% amino acid sequence identity to SEQ ID NO:1. Preferably said mutant acs2 protein is a *Solanum lycopersicum* acs2 protein.

In another aspect the invention relates to a plant of the invention wherein said mutation or mutations result in reduced ethylene production and/or delayed fruit ripening and/or a longer shelf life compared to *Solanum lycopersicum* plants which are homozygous for the wild type fully functional Acs2 allele (Acs2/Acs2) (encoding a functional Acs2 protein of SEQ ID NO: 1 or a functional variant of SEQ ID NO: 1). In another aspect, the mutation or mutations in the plant of the invention result in reduced ethylene production compared to *Solanum lycopersicum* being homozygous for the wild type Acs2 allele encoding the protein of SEQ ID NO:1 or of a wild type variant of SEQ ID NO: 1 having at least 85% amino acid sequence identity to SEQ ID NO:1.

In another aspect, the mutation or mutations in the plant of the invention result in delayed fruit ripening and/or a longer shelf life compared to *Solanum lycopersicum* being homozygous for the wild type Acs2 allele.

In yet another aspect, the invention relates to a cultivated plant of the species *Solanum lycopersicum* and/or parts thereof (e.g. fruits) comprising an acs2 allele having one or more mutations, said mutations resulting in production of a mutant acs2 protein, wherein said mutant acs2 protein has one or more amino acids changed selected from the group consisting of A101T, A101V, A103T, G112R, P118L, V147E, C265Y of SEQ ID NO: 1 or variants of SEQ ID NO: 1 and wherein said mutation(s) result(s) in production of a mutant acs2 protein having loss-of-function or reduced function compared to wild type Acs2 protein (or wild type variant) whereby the fruits of the plant do ripen to the red stage (preferably slower than plants homozygous for the wild type allele, encoding a fully functional Acs2 protein (or wild type variant).

In one aspect the plant is homozygous for the allele encoding the mutant acs2 protein.

In still another embodiment such mutant acs2 allele is derived from and/or generated in a cultivated tomato (e.g. a breeding line, variety or heirloom variety) or a wild relative of tomato. Such a human-induced mutation may, for example, be induced using targeted mutagenesis as described in EP1963505. Mutant acs2 alleles generated in wild relatives of tomato are then easily transferred into cultivated tomato by breeding.

In yet another aspect, the invention relates to a plant of the invention having reduced ethylene production and/or delayed ripening and/or longer shelf-life than wild type (Acs2/Acs2) plants, due to said plants comprising an endogenous acs2 allele encoding a loss-of-function acs2 protein or reduced-function acs2 protein having substantial sequence identity to SEQ. ID NO: 2 or to SEQ. ID NO: 3, or to SEQ. ID NO: 4, or to SEQ. ID NO: 5 or to SEQ. ID NO: 6, or to SEQ. ID NO: 7 or to SEQ. ID NO: 8.

In a specific aspect, the invention relates to cultivated tomato plants comprising an acs2 allele as found in, and is derivable from or obtainable from (or derived from or obtained from) seed deposited under accession number NCIMB 42032, NCIMB 42033, NCIMB 42035, NCIMB 42036, NCIMB 42040, NCIMB 42042, or NCIMB 42043 in one or two copies, i.e. in homozygous or heterozygous form. In heterozygous form, the other allele may be a wild type Acs2 allele or another mutant acs2 allele, such as from any one of the other mutants provided herein, or any other mutant acs2 allele encoding for a loss-of-function acs2 protein or reduced-function acs2 protein as described herein. In heterozygous form, the other allele may, thus, be a reduced function or a loss-of-function acs2 allele.

In still another aspect, the invention relates to an endogenous acs2 allele, or to a loss-of-function acs2 protein or a reduced-function acs2 protein encoded by it, said protein comprising an amino acid sequence having substantial sequence identity to SEQ. ID NO: 18 or to SEQ. ID NO: 19 or to SEQ. ID NO: 20 or to SEQ. ID NO: 21 or to SEQ. ID NO: 22 or to SEQ. ID NO: 23 or to SEQ. ID NO: 24.

In another aspect the invention relates to an endogenous acs2 allele, or to a loss-of-function acs2 protein or a reduced-function acs2 protein encoded by it, said protein having substantial sequence identity to SEQ. ID NO: 2 or to SEQ. ID NO: 3, or to SEQ. ID NO: 4, or to SEQ. ID NO: 5 or to SEQ. ID NO: 6, or to SEQ. ID NO: 7, or to SEQ. ID NO: 8 as found in and/or as derivable from or obtainable from (and as derived from or obtained from) seed deposited under accession number NCIMB 42032, NCIMB 42033, NCIMB 42035, NCIMB 42036, NCIMB 42040, NCIMB 42042, or NCIMB 42043, respectively.

In yet another aspect, the invention relates to a tomato plant or plant part of the invention comprising an endogenous acs2 allele encoding an acs2 protein having 100% sequence identity to SEQ. ID NO: 2, or to SEQ. ID NO: 3, or to SEQ. ID NO: 4, or to SEQ. ID NO: 5, or to SEQ. ID NO: 6, or to SEQ. ID NO: 7 or to SEQ. ID NO: 8.

In still another aspect the invention relates to a tomato plant or plant part comprising an endogenous acs2 allele encoding an acs2 protein wherein said protein comprises a part having substantial sequence identity to SEQ. ID NO: 18 or to SEQ. ID NO: 19 or to SEQ. ID NO: 20 or to SEQ. ID NO: 21 or to SEQ. ID NO: 22 or to SEQ. ID NO: 23 or to SEQ. ID NO: 24; preferably wherein said protein comprises a part having 100% sequence identity to SEQ. ID NO: 18 or to SEQ. ID NO: 19 or to SEQ. ID NO: 20 or to SEQ. ID NO: 21 or to SEQ. ID NO: 22 or to SEQ. ID NO: 23 or to SEQ. ID NO: 24.

The invention further relates to tomato seeds, plants and plant parts comprising an endogenous acs2 gene encoding a cDNA (mRNA) having substantial sequence identity to SEQ. ID NO: 9 and having at least one non-transgenic mutation within said endogenous acs2 gene, wherein the mutation results in an amino acid substitution selected from the group consisting of Ala101, Ala103, Gly112, Pro118, and Val147 and Cys265 of the wild type Acs2 protein, e.g. wherein the mutation is selected from the group consisting of Ala101Thr, Ala101Val, Ala103Thr, Gly112Arg, Pro118Leu, Val147Glu, and Cys265Tyr.

In another aspect the invention relates to tomato seeds, plants and plant parts of the invention wherein said at least one non-transgenic mutation results in the production of a mutant acs2 protein having loss-of-function acs2 protein or reduced activity compared to wild type Acs2 protein. Preferably, said mutation results in reduced ethylene production and/or slower fruit ripening and/or a longer shelf life compared to *Solanum lycopersicum* being homozygous for the functional wild type Acs2 allele, encoding the protein of SEQ ID NO: 1 or a functional variant thereof. The mutation described anywhere herein may be human-induced or it may be a natural mutation. The plant is preferably a cultivated tomato plant. In another embodiment, said mutation is selected from the group consisting of G307A, G334A, C353T, C302T, G301A, G794A, and T440A of SEQ ID NO: 9.

In another aspect the invention relates to tomato seeds, plants and plant parts comprising an endogenous mutant acs2 gene wherein said non-transgenic mutation creates an amino acid change in the acs2 protein encoded by and produced by transcription and translation of the acs2 gene, wherein said amino acid change is selected from the group consisting of A101T, A101V, A103T, G112R, P118L, V147E, and C265Y of SEQ ID NO: 1 or of a functional variant of SEQ ID NO: 1 having at least 85% amino acid sequence identity to SEQ ID NO: 1.

In yet another aspect the invention relates to acs2 protein having substantial sequence identity to SEQ ID NO: 2. In still another aspect the invention relates to acs2 protein having substantial sequence identity to SEQ ID NO: 3. In a further aspect the invention relates to acs2 protein having substantial sequence identity to SEQ ID NO: 4. In yet another aspect the invention relates to acs2 protein having substantial sequence identity to SEQ ID NO: 5. In still another aspect the invention relates to acs2 protein having substantial sequence identity to SEQ ID NO: 6. In a further aspect the invention relates to acs2 protein having substantial sequence identity to SEQ ID NO: 7. In yet another aspect the invention relates to acs2 protein having substantial sequence identity to SEQ ID NO: 8. The invention also relates to tomato seeds, plants and plant parts comprising a nucleotide sequence encoding these proteins.

In still another aspect, the invention relates to tomato fruit, seeds, pollen, plant parts, and/or progeny of a plant of the invention. Preferably, the invention relates to fruit or seeds of the plant of the invention. More preferably, the invention relates to tomato fruit having delayed ripening and/or an increased post-harvest shelf life caused by a non-transgenic mutation in at least one acs2 allele, as described elsewhere herein.

In still another aspect, the invention relates to tomato fruit, seeds, pollen, plant parts, and/or progeny of a plant of the invention comprising an acs2 protein having one or more amino acids changed selected from the group consisting of A101T, A101V, A103T, G112R, P118L, V147E, and C265Y in a wild type Acs2 protein, said protein having at least 85% amino acid sequence identity to SEQ ID NO: 1. In another embodiment, the invention relates to fruit or seeds of such plant of the invention. In still another embodiment, the invention relates to tomato fruit having delayed ripening and/or an increased post-harvest shelf life caused by a non-transgenic mutation in at least one acs2 allele, as described elsewhere herein.

In one aspect the tomato plants according to the invention have a delay of breaker stage, meaning that the mutants according to the invention require significantly more days e.g. 1, 2, 3, 4, 5, 6, 7, 8, 9, or 10 or more days than wild type Acs2/Acs2 controls, such as TAPA, TPAADASU, or Pusa Sheetal, for the first fruits and/or for all fruits to have entered breaker stage.

In another aspect fruits of the tomato plants of the invention require more days to go from breaker stage to red stage, e.g. fruits of the plants of the invention require 1, 2, 3, 4, 5, 6, 7, 8, 9, 10, 11, 12, 13 or 14 or more days than wild type Acs2/Acs2 controls to go from breaker stage to red stage.

In another aspect the invention relates to a fruit of a plant of the invention having a the shelf life that is at least 2 days longer than the shelf life of a tomato fruit being homozygous for the wild type Acs2 allele. In still another aspect the invention relates to a fruit according to a plant of the invention having a reduced ethylene production that is at least 10% reduced, or at least 15% reduced or at least 20% reduced compared to *Solanum lycopersicum* being homozygous for the wild type Acs2 allele. In another aspect the invention relates to a fruit according to a plant of the invention having a reduced ethylene production that is at least 10% reduced, or at least 15% reduced or at least 20% reduced compared to *Solanum lycopersicum* being homozygous for the wild type Acs2 allele, when measured at the pink or red stage.

In a particular aspect the tomato plants according to the invention have a shelf life that is significantly longer than the shelf life of wild type plants, for example the number of days from the first fruit being in breaker stage (or turning stage, pink stage, red stage or from harvest) up to the first fruit starting to become 'bad' and unsuitable for sale or consumption is significantly longer, e.g. at least 1, 2, 3, 4, 5, 6, 7, 8, 9, 10, or more, days longer than fruits of control plants (such as wild type Acs2/Acs2 plants), when plants are grown under the same conditions and fruits are treated the same way and kept under the same conditions.

Figure 2:
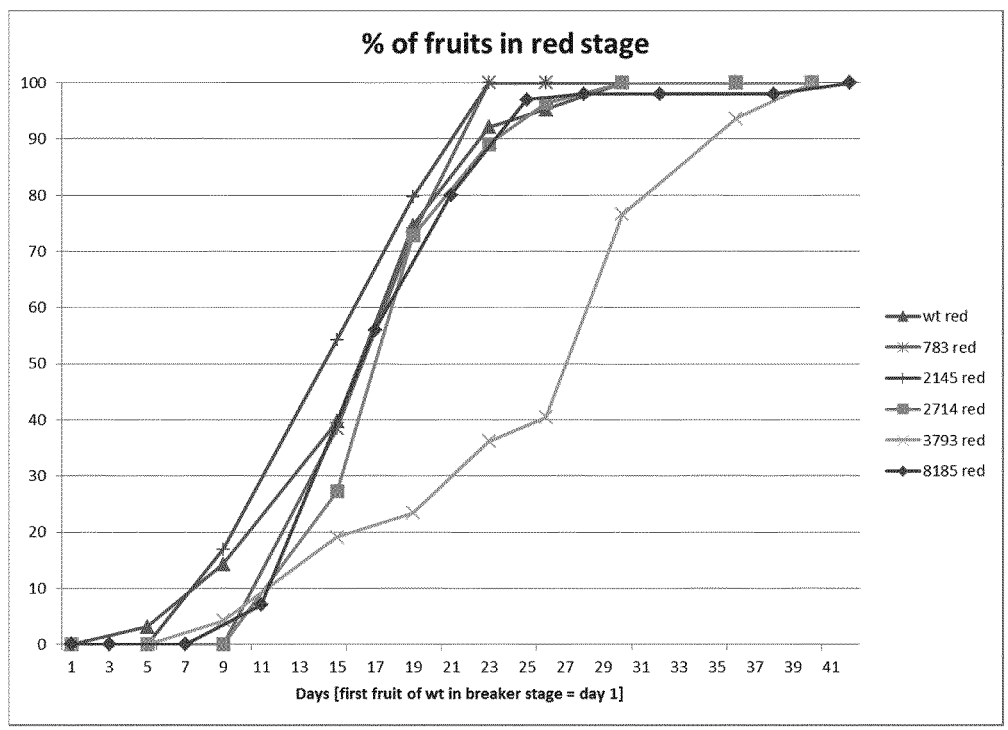
FIG. 2: In this graph the percentage of fruits in red stage is shown, determined at various days after the wild type control fruits started entering breaker stage [at day 1, the first fruit of Wild type was in breaker stage]. Fruits of the mutant plants (indicated by the mutant number) were homozygous for a specific acs2 mutation (acs2/acs2).
Figure 4:
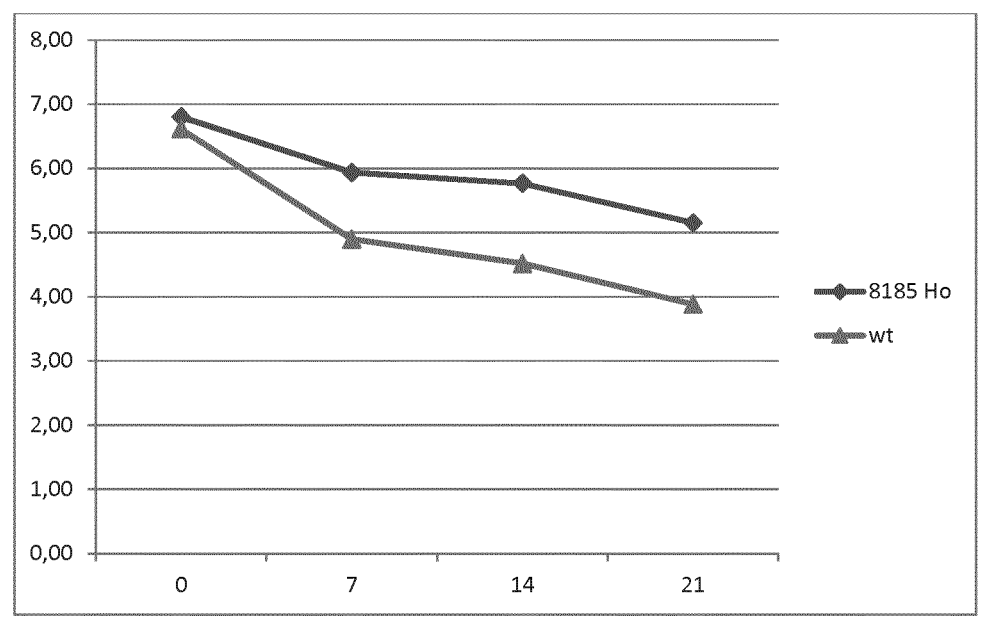
FIG. 4: Average firmness necessary to decrease the fruit diameter 1 mm per cm fruit (10%) of mutant 8185 (8185 Ho) and wild type (wt; i.e. Tapa) in Newton [N]. The same fruits were repeatedly measured at 0 (red stage, day of harvest) and 7, 14, and 21 days after harvest.

A delayed ripening and/or extended shelf-life can have the advantage that more time is available for transport of picked fruits e.g. to retailers and supermarkets and/or that the consumer can keep the fruits longer. Tomatoes can be harvested at mature green stage or at breaker stage, or thereafter. When harvested before breaker stage, ethylene exposure is needed, while harvest around breaker stage or thereafter does not require ethylene exposure, as the fruits produce ethylene themselves. As seen in FIG. 2, delayed-ripening mutants according to the invention produce less ethylene at pink stage and red stage than wild type fruits, but sufficient ethylene to ripen to the red stage. In one aspect of the invention tomato plants are provided comprising a mutant acs2 allele encoding a loss-of-function acs2 protein or reduced function acs2 protein, wherein the fruits of said plants produce significantly less ethylene than wild type (Acs2/Acs2) plants. "Significantly less ethylene" refers to the fruit producing equal to or less than 75%, equal to or less than 70%, equal to or less than 65%, equal to or less than 60%, equal to or less than 55%, equal to or less than 50%, equal to or less than 45%, equal to or less than 40%, equal to or less than 35%, equal to or less than 30%, equal to or less than 25% equal to or less than 20%, or equal to or less than 15% of the ethylene produced by homozygeous Acs2/Acs2 fruits at the pink or red stage. Thus, the ethylene produced at the pink stage is in one aspect below about 3.5 nl/(h·g), such as equal to or below about 3 nl/(h·g) or equal to or below about 2.5 nl/(h·g) or equal to or below about 2.0 nl/(h·g) or equal to or below about 1.5 nl/(h·g) or equal to or below about 1.0 nl/(h·g) or equal to or below about 0.5 nl/(h·g). The ethylene produced at the red stage is in one aspect below about 6 nl/(h·g), such as equal to or below about 5.5 nl/(h·g) or equal to or below about 5.0 nl/(h·g), or equal to or below 4.5 nl/(h·g), or equal to or below about 3.5 nl/(h·g), or equal to or below about 3 nl/(h·g) or equal to or below about 2.5 nl/(h·g) or equal to or below about 2.0 nl/(h·g) or equal to or below about 1.5 nl/(h·g) or equal to or below about 1.0 nl/(h·g) or equal to or below about 0.5 nl/(h·g).

In another aspect, the invention relates to tomato fruit of a plant of the invention having a longer ripening period and/or an increased post-harvest shelf life caused by a non-transgenic mutation in at least one acs2 allele wherein the longer ripening period and/or the longer post-harvest shelf life is at least 110% of the ripening period and/or of the post-harvest shelf life of a tomato fruit being homozygous for the wild type Acs2 allele. Preferably, the ripening period and/or post-harvest shelf life is at least 115%, more preferably at least 120%, even more preferably at least 125% of the ripening period and/or post-harvest shelf life of a tomato fruit being homozygous for the wild type Acs2 allele. In another aspect, the ripening period and/or post-harvest shelf life is at least 135%, more preferably at least 150%, even more preferably at least 165% of the ripening period and/or post-harvest shelf life of a tomato fruit being homozygous for the wild type Acs2 allele. In yet another aspect, the ripening period and/or post-harvest shelf life is at least 180%, more preferably at least 200% even more preferably at least 250% of the ripening period and/or post-harvest shelf life of a tomato fruit being homozygous for the wild type Acs2 allele.

In yet another aspect, the invention relates to a tomato plant comprising an acs2 allele encoding a mutant acs2 protein said allele being derived or derivable, or obtained or obtainable from a plant of the invention representative seed of which having been deposited under Accession Number NCIMB 42032, NCIMB 42033, NCIMB 42035, NCIMB 42036, NCIMB 42040, NCIMB 42042, or NCIMB 42043.

In still another aspect of the invention tomato plants are provided that have the same or similar delayed ripening and/or increased shelf life as tomato plants of the invention, of which representative seeds were deposited by Nunhems B. V. and accepted for deposit on 21 Aug. 2012 at the NCIMB Ltd. (Ferguson Building, Craibstone Estate, Bucksburn Aberdeen, Scotland AB21 9YA, UK) according to the Budapest Treaty, under the Expert Solution (EPC 2000, Rule 32(1)). Seeds were given the following deposit numbers: NCIMB 42032 (mutant 783), NCIMB 42033 (mutant 2145), NCIMB 42035 (mutant 2714), NCIMB 42036 mutant (3793), NCIMB 42040 (mutant 4946), NCIMB 42042 (mutant 7871), or NCIMB 42043 (mutant 8185).

According to a further aspect the invention provides a cell culture or tissue culture of the tomato plant of the invention. The cell culture or tissue culture comprises regenerable cells. Such cells can be derived from leaves, pollen, embryos, cotyledon, hypocotyls, meristematic cells, roots, root tips, anthers, flowers, seeds and stems.

Seeds from which plants according to the invention can be grown are also provided, as well as packages or containers containing such seeds. Also a vegetative propagation of plants according to the invention are an aspect encompassed herein. Likewise harvested fruits and fruit parts, either for fresh consumption or for processing or in processed form are encompassed. Fruits may be graded, sized and/or packaged. Fruits may be sliced or diced or further processed.

In another aspect the invention relates to one or more cells of a plant of the invention.

The invention also relates to food and/or food products comprising or consisting of the fruit, or part of a fruit, of a tomato plant of the invention. As used herein, food refers to nutrients consumed by human or animal species. Examples are sandwiches, salads, sauces, ketchup and the like.

A method of producing a tomato plant of the invention comprising the steps of:
a. obtaining plant material from a tomato plant;
b. treating said plant material with a mutagen to create mutagenized plant material;
c. analyzing said mutagenized plant material to identify a plant having at least one mutation in at least one acs2 allele having substantial sequence identity to SEQ ID NO: 1 or in a functional variant thereof.

The method may further comprise analyzing the ripening period and/or shelf life of tomato fruits of the selected plant or progeny of the plant and selecting a plant of which the fruit have delayed ripening and/or extended shelf-life.

In one aspect the mutation is selected from a mutation resulting in an amino acid substitution selected from the group consisting of A101T, A101V, A103T, G112R, P118L, V147E, C265Y of SEQ ID NO: 1 or of a part thereof. In a further aspect, the mutation is selected from a mutation causing a change in the cDNA selected from the group consisting of G307A, G334A, C353T, C302T, G301A, G794A, and T440A of SEQ ID NO: 9. In this method, the plant material of step a) is preferably selected from the group consisting of seeds, pollen, plant cells, or plant tissue of a tomato plant line or cultivar. Plant seeds being more preferred. In another aspect, the mutagen used in this method is ethyl methanesulfonate. In step b) and step c) the mutagenized plant material is preferably a mutant population, such as a tomato TILLING population.

Thus, in one aspect a method for producing a tomato plant comprising delayed fruit ripening and/or longer fruit shelf-life is provided comprising the steps of:
a) providing a tomato TILLING population,
b) screening said TILLING population for mutants in the acs2 gene, and
c) selecting from the mutant plants of b) those plants (or progeny of those plants) of which the fruits have a reduced ethylene production and/or a delayed ripening and/or longer shelf life than wild type (Acs2/Acs2) fruits.

Mutant plants (M1) are preferably selfed one or more times to generate for example M2 populations or preferably M3 or M4 populations for phenotyping. In M2 populations the mutant allele is present in a ratio of 1 (homozygous for mutant allele):2 (heterozygous for mutant allele):1 (homozygous for wild type allele).

In yet a further aspect the invention relates to a method for producing a hybrid *Solanum lycopersicum* plant, said method comprising:
(a) obtaining a first *Solanum lycopersicum* plant of the current invention or from a seed from which a plant of the invention can be grown; and (b) crossing said first *Solanum lycopersicum* plant with a second *Solanum lycopersicum* plant to obtain hybrid seeds, wherein said hybrid *Solanum lycopersicum* plant comprises an acs2 allele having one or more mutations wherein said mutations result in production of a mutant acs2 protein having one or more amino acids changed selected from the group consisting of A101T, A101V, A103T, G112R, P118L, V147E, and C265Y of SEQ ID NO: 1 or of a variant of SEQ ID NO: 1.

Plants and plant parts (e.g. fruits, cells, etc.) of the invention can be homozygous or heterozygous for the mutant acs2 allele.

Preferably the plants according to the invention, which comprise one or more mutant acs2 alleles, and which produce a mutant acs2 protein having loss-of-function acs2 protein or reduced activity compared to wild type Acs2 protein, do not produce fewer fruits than the wild type plants. Thus, fruit number per plant is preferably not reduced.

Other putative ACS2 genes/proteins can be identified in silico, e.g. by identifying nucleic acid or protein sequences in existing nucleic acid or protein database (e.g. GEN-BANK, SWISSPROT, TrEMBL) and using standard sequence analysis software, such as sequence similarity search tools (BLASTN, BLASTP, BLASTX, TBLAST, FASTA, etc.).

In one embodiment loss-of-function acs2 protein or reduced-function mutant acs2 proteins (including variants or orthologs, such as acs2 proteins of wild tomato relatives) are provided and plants and plant parts comprising one or more acs2 alleles in their genome, which encode loss-of-function acs2 protein or reduced-function mutants, whereby the reduced-function confers reduced ethylene production and/or slower fruit ripening and/or a longer shelf life compared to *Solanum lycopersicum* being homozygous for the wild type Acs2 allele.

Any type of mutation may lead to a reduction in function of the encoded Acs2 protein, e.g. insertion, deletion and/or replacement of one or more nucleotides in the genomic DNA which comprises the cDNA (SEQ ID NO: 9, or variants thereof). In a preferred embodiment an acs2 nucleic acid sequence, encoding a loss-of-function acs2 protein or reduced-function acs2 protein due to one or more mutation(s), is provided, said acs2 protein causing reduced ethylene production and/or conferring slower fruit ripening and/or a longer shelf life compared to *Solanum lycopersicum* being homozygous for the wild type Acs2 allele.

The in vivo loss-of-function acs2 protein or reduced-function of such proteins can be tested as described herein, by determining the effect this mutant allele has on ethylene production and/or ripening period and/or shelf life period. Plants comprising a nucleic acid sequence encoding such mutant loss-of-function acs2 protein or reduced-function proteins and having a reduced ethylene production and/or slower fruit ripening and/or a longer shelf life compared to *Solanum lycopersicum* being homozygous for the wild type Acs2 allele can for example be generated using e.g. mutagenesis and identified by TILLING or identified using EcoTILLING, as known in the art. Also transgenic methods can be used to test in vivo functionality of a mutant acs2 allele encoding a mutant acs2 protein. A mutant allele can be operably linked to a plant promoter and the chimeric gene can be introduced into a tomato plant by transformation. Regenerated plants (or progeny, e.g. obtained by selfing), can be tested for ethylene production and/or fruit ripening period and/or shelf life. For example a tomato plant comprising a non-functional acs2 allele can be transformed to test the functionality of the transgenic acs2 allele.

TILLING (Targeting Induced Local Lesions IN Genomes) is a general reverse genetics technique that uses traditional chemical mutagenesis methods to create libraries of mutagenized individuals that are later subjected to high throughput screens for the discovery of mutations. TILLING combines chemical mutagenesis with mutation screens of pooled PCR products, resulting in the isolation of missense and non-sense mutant alleles of the targeted genes. Thus, TILLING uses traditional chemical mutagenesis (e.g. EMS or MNU mutagenesis) or other mutagenesis methods (e.g. radiation such as UV) followed by high-throughput screening for mutations in specific target genes, such as Acs2 according to the invention. Si nucleases, such as CEL1 or ENDOI, are used to cleave heteroduplexes of mutant and wildtype target DNA and detection of cleavage products using e.g. electrophoresis such as a LI-COR gel analyzer system, see e.g. Henikoff et al. Plant Physiology 2004, 135: 630-636. TILLING has been applied in many plant species, such as tomato. (see world wide web at tilling.ucdavis.edu/index.nlin/Tomato_Tilling), rice (Till et al. 2007, BMC Plant Biol 7: 19), Arabidopsis (Till et al. 2006, Methods Mol Biol 323: 127-35),-Brassica, maize (Till et al. 2004, BMC Plant Biol 4: 12), etc. Also EcoTILLING, whereby mutants in natural populations are detected, has been widely used, see Till et al. 2006 (Nat Protoc 1: 2465-77) and Comai et al. 2004 (Plant J 37: 778-86).

In one embodiment of the invention (cDNA or genomic) nucleic acid sequences encoding such mutant acs2 proteins comprise one or more non-sense and/or missense mutations, e.g. transitions (replacement of purine with another purine (A⇌G) or pyrimidine with another pyrimidine (C⇌T)) or transversions (replacement of purine with pyrimidine, or vice versa (C/T⇌A/G). In one embodiment the non-sense and/or missense mutation(s) is/are in the nucleotide sequence encoding any of the Acs2 exons, or an essentially similar domain of a variant Acs2 protein, i.e. in a domain comprising at least 80%, 90%, 95%, 98%, 99% amino acid sequence identity to amino acids of SEQ ID NO: 1 or to a variant thereof.

In one embodiment an acs2 nucleotide sequence comprising one or more non-sense and/or missense mutations in one of the exon-encoding sequence are provided, as well as a plant comprising such a mutant allele resulting in reduced ethylene production and/or delayed fruit ripening and/or a longer shelf life compared to *Solanum lycopersicum* being homozygous for the wild type Acs2 allele.

In a specific embodiment of the invention tomato plants and plant parts (fruits, seeds, etc.) comprising a mutant loss-of-function or reduced-function acs2 allele are provided.

Also provided are nucleic acid sequences (genomic DNA, cDNA, RNA) encoding loss-of-function acs2 protein or reduced-function acs2 proteins, such as for example acs2 depicted in SEQ ID NO: 2, 3, 4, 5, 6, 7, or 8; or variants thereof as defined above (including any chimeric or hybrid proteins or mutated proteins or truncated proteins). Due to the degeneracy of the genetic code various nucleic acid sequences may encode the same amino acid sequence. The nucleic acid sequences provided include naturally occurring, artificial or synthetic nucleic acid sequences. A nucleic acid sequence encoding Acs2 is provided for in SEQ ID NO: 9 (wild type cDNA), NCBI Reference Sequence: NM_001247249.1 world wide web at ncb.nih.gov/nuc-corefNM 001247249.

It is understood that when sequences are depicted as DNA sequences while RNA is referred to, the actual base sequence of the RNA molecule is identical with the difference that thymine (T) is replace by uracil (U). When referring herein to nucleotide sequences (e.g DNA or RNA) italics are used, e.g. acs2 allele, while when referring to proteins, no italics are used, e.g. acs2 protein. Mutants are in small letters (e.g acs2 allele or acs2 protein), while wild type/functional forms start with a capital letter (Acs2 allele or Acs2 protein).

Also provided are nucleic acid sequences (genomic DNA, cDNA, RNA) encoding mutant acs2 proteins, i.e. loss-of-function acs2 protein or reduced function acs2 proteins, as described above, and plants and plant parts comprising such mutant sequences. For example, acs2 nucleic acid sequences comprising one or more non-sense and/or missense mutations in the wild type Acs2 coding sequence, rendering the encoded protein having a loss-of-function or reduced function in vivo. Also sequences with other mutations are provided, such as splice-site mutants, i.e. mutations in the genomic acs2 sequence leading to aberrant splicing of the pre-mRNA, and/or frame-shift mutations, and/or insertions (e.g. transposon insertions) and/or deletions of one or more nucleic acids.

It is clear that many methods can be used to identify, synthesise or isolate variants or fragments of acs2 nucleic acid sequences, such as nucleic acid hybridization, PCR technology, in silico analysis and nucleic acid synthesis, and the like. Variants of SEQ ID NO: 9, may either encode wild type, functional Acs2 proteins, or they may encode loss-of-function acs2 protein or reduced-function mutant alleles of any of these, as for example generated e.g. by mutagenesis and/or identified by methods such as TILLING or EcoTILLING, or other methods.

A plant of the invention can be used in a conventional plant breeding scheme to produce more plants with the same characteristics or to introduce the mutated acs2 allele into other plant lines or varieties of the same or related plant species.

Also transgenic plants can be made using the mutant acs2 nucleotide sequences of the invention using known plant transformation and regeneration techniques in the art. An "elite event" can be selected, which is a transformation event having the chimeric gene (comprising a promoter operably linked to a nucleotide sequence encoding a loss-of-function acs2 protein or reduced-function acs2 protein) inserted in a particular location in the genome, which results in good expression of the desired phenotype.

The plants of the invention as described above are homozygous for the mutant acs2 allele, or heterozygous. To generate plants comprising the mutant allele in homozygous form, selling can be used. The mutant acs2 alleles according to the invention can be transferred to any other tomato plant by traditional breeding techniques, such as crossing, selfing, backcrossing, etc. Thus any type of tomato having delayed ripening and/or longer shelf life due to the presence of at least one mutant acs2 allele according to the invention can be generated. Any S. lycopersicum may be generated and/or identified having at least one mutant acs2 allele in its genome and producing a acs2 protein having loss-of-function acs2 protein or reduced activity compared to wild type Acs2 protein. The tomato plant may, thus, be any cultivated tomato, any commercial variety, any breeding line or other, it may be determinate or indeterminate, open pollinated or hybrid, producing fruits of any colour, shape and size. The mutant allele generated and/or identified in a particular tomato plant, or in a sexually compatible relative of tomato, may be easily transferred into any other tomato plant by breeding (crossing with a plant comprising the mutant allele and then selecting progeny comprising the mutant allele).

The presence or absence of a mutant acs2 allele according to the invention in any tomato plant or plant part and/or the inheritance of the allele to progeny plants can be determined phenotypically and/or using molecular tools (e.g. detecting the presence or absence of the acs2 nucleotide sequence or acs2 protein using direct or indirect methods).

The mutant allele is in one embodiment generated or identified in a cultivated plant, but may also be generated and/or identified in a wild plant or non-cultivated plant and then transferred into an cultivated plant using e.g. crossing and selection (optionally using interspecific crosses with e.g. embryo rescue to transfer the mutant allele). Thus, a mutant acs2 allele may be generated (human induced mutation using mutagenesis techniques to mutagenize the target acs2 gene or variant thereof) and/or identified (spontaneous or natural allelic variation) in *Solarium lycopersicum* or in other *Solarium* species include for example wild relatives of tomato, such as *S. cheesmanii, S. chilense, S. habrochaites* (*L. hirsutum*), *S. chmielewskii, S. lycopersicum*×*S. peruvianum, S. glandulosum, S. hirsutum, S. minutum, S. parviflorum, S. pennellii, S. peruvianum, S. peruvianum* var. *humifusum* and *S. pimpinellifolium*, and then transferred into a cultivated *Solarium* plant, e.g. *Solanum lycopersicum* by traditional breeding techniques. The term "traditional breeding techniques" encompasses herein crossing, selfing, selection, double haploid production, embryo rescue, protoplast fusion, transfer via bridge species, etc. as known to the breeder, i.e. methods other than genetic modification by which alleles can be transferred.

In another embodiment, the plant comprising the mutant acs2 allele (e.g. tomato) is crossed with another plant of the same species or of a closely related species, to generate a hybrid plant (hybrid seed) comprising the mutant acs2 allele. Such a hybrid plant is also an embodiment of the invention.

In one embodiment F1 hybrid tomato seeds (i.e. seeds from which F1 hybrid tomato plants can be grown) are provided, comprising at least one acs2 allele according to the invention. F1 hybrid seeds are seeds harvested from a cross between two inbred tomato parent plants. Such an F1 hybrid may comprise one or two mutant acs2 alleles according to the invention. Such an F1 hybrid comprising two mutant acs2 alleles according to the invention may comprise two copies of the same acs2 allele or two different acs2 alleles according to the invention. Thus, in one embodiment a plant according to the invention is used as a parent plant to produce an F1 hybrid, the fruit of which have reduced ethylene production and/or delayed ripening and/or longer shelf-life than wild type Acs2/Acs2 plants.

Also a method for transferring a mutant acs2 allele to another plant is provided, comprising providing a plant comprising a mutant acs2 allele in its genome, whereby the plant comprising the mutant allele produce fruits that show reduced ethylene production and/or slower fruit ripening and/or a longer shelf life compared to *Solanum lycopersicum* being homozygous for the wild type Acs2 allele (as described above), crossing said plant with another plant and obtaining the seeds of said cross. Optionally plants obtained from these seeds may be further selfed and/or crossed and progeny selected comprising the mutant allele and producing fruits with delayed ripening and/or longer shelf-life and/or reduced ethylene production due to the presence of the mutant allele compared to plants comprising the wild type Acs2 allele.

As mentioned, it is understood that other mutagenesis and/or selection methods may equally be used to generate mutant plants according to the invention. Seeds may for example be radiated or chemically treated to generate mutant populations. Also direct gene sequencing of acs2 may be used to screen mutagenized plant populations for mutant alleles. For example KeyPoint screening is a sequence based method which can be used to identify plants comprising mutant acs2 alleles (Rigola et al. PloS One, March 2009, Vol 4(3):e4761).

Thus, non-transgenic mutant tomato plants which produce lower levels of wild type Acs2 protein in fruits are provided, or which completely lack wild type Acs2 protein in fruits, and which produce loss-of-function acs2 protein or reduced-function acs2 protein in fruits due to one or more mutations in one or more endogenous acs2 alleles, are provided. These mutants may be generated by mutagenesis methods, such as TILLING or variants thereof, or they may be identified by EcoTILLING or by any other method. Acs2 alleles encoding loss-of-function acs2 protein or reduced-functional acs2 protein may be isolated and sequenced or may be transferred to other plants by traditional breeding methods.

Any part of the plant, or of the progeny thereof, is provided, including harvested fruit, harvested tissues or organs, seeds, pollen, flowers, ovaries, etc. comprising a mutant acs2 allele according to the invention in the genome. Also plant cell cultures or plant tissue cultures comprising in their genome a mutant acs2 allele are provided. Preferably, the plant cell cultures or plant tissue cultures can be regenerated into whole plants comprising a mutant acs2 allele in its genome. Also double haploid plants (and seeds from which double haploid plants can be grown), generated by chromosome doubling of haploid cells comprising an acs2 mutant allele, and hybrid plants (and seeds from which hybrid plants can be grown) comprising a mutant acs2 allele in their genome are encompassed herein, whereby the double haploid plants and hybrid plants produce delayed ripening and/or longer shelf life fruits according to the invention.

The invention further relates to an endogenous acs2 protein having at least one human-induced non-transgenic mutation selected from A101T, A101V, A103T, G112R, P118L, V147E and C265Y of SEQ ID NO: 1 or an endogenous acs2 allele encoding such protein.

In another aspect the invention relates to a cultivated plant or plant part (e.g. seed) of the species Solanum lycopersicum of the invention comprising in addition to the one or more mutations in the acs2 allele as described herein, an acs4 allele having one or more mutations, said mutations in said acs4 allele resulting in production of a mutant acs4 protein having loss-of-function or reduced function compared to Solanum lycopersicum wild type Acs4 protein, having a protein sequence as shown in FIG. 5 and/or as derived from the mRNA based on Genbank Accession number AAA34131.1 (encoded by the cDNA of GenBank Accession number M63490.1).

A "reduced function acs4 protein" or "reduced activity acs4 protein" refers to a mutant acs4 protein which has a reduced catalytic activity in synthesizing ACC from S-Adenosyl methionine, leading to reduced ethylene synthesis compared to wild-type Acs4 protein. Said reduced catalytic activity of the acs4 protein affects the ripening behaviour of the fruits comprising such reduced function acs4 protein when the allele encoding the mutant protein is present in homozygous or heterozygous form in the tomato plant, i.e. delayed ripening and/or longer shelf-life of the fruits. Such a reduced function acs4 protein can be obtained by the transcription and translation of a "partial knockout mutant acs4 allele" which is, for example, a wild-type Acs4 allele, which comprises one or more mutations in its nucleic acid sequence. In one aspect, such a partial knockout mutant acs4 allele is a wild-type Acs4 allele, which comprises one or more mutations that preferably result in the production of an acs4 protein wherein at least one conserved and/or functional amino acid is substituted for another amino acid, such that the biological activity is significantly reduced but not completely abolished. However, other mutations, such as one or more non-sense, missense, splice-site or frameshift mutations in the tomato Acs4 allele may also result in reduced function acs4 protein and such reduced function proteins may have one or more amino acids replaced, inserted or deleted, relative to the wild type ACS4 protein. Such partial knockout mutant acs4 allele may also encode a dominant negative acs4 protein, which is capable of adversely affecting the biological activity of other Acs4 proteins within the same cell. Such a dominant negative acs4 protein can be an acs4 protein that is still capable of interacting with the same elements as the wild-type Acs4 protein, but that blocks some aspect of its function. Examples of dominant negative acs4 proteins are acs4 proteins that lack, or have modifications in specific amino acid residues critical for activation, but still contain their binding domain, such that not only their own biological activity is reduced or abolished, but that they further reduce the total acs4 activity in the cell by competing with wild type and/or partial knockout acs4 proteins present in the cell for binding sites. Mutant alleles can be either "natural mutant" alleles, which are mutant alleles found in nature (e.g. produced spontaneously without human application of mutagens) or "induced mutant" alleles, which are induced by human intervention, e.g. by mutagenesis.

A "loss-of-function acs4 protein" refers to a mutant acs4 protein which has essentially no catalytic activity in synthesising ACC from S-Adenosyl methionine compared to wild-type Acs4 protein, leading to reduced ethylene synthesis compared to wild type Acs4 protein. Said lack of catalytic activity synthesis affects the ripening behaviour of the fruits comprising such loss-of-function acs4 protein when the allele encoding the mutant protein is present in homozygous or heterozygous form in the tomato plant. Fruits of tomato plants homozygous for such a "loss-of-function acs4 protein" may still produce ethylene catalysed by other proteins (e.g. other Acs proteins like Acs1A). As a consequence, fruits of tomato plants homozygous for such a "loss-of-function acs4 protein" may still ripen, but ripening may be delayed and/or shelf life may be longer.

In one aspect said mutant acs4 allele is the allele as found in, and as obtained from and/or obtainable from and/or derived from and/or derivable from seed of mutant 2477 and/or mutant 4043 and/or mutant 4222, and/or mutant 4303 and/or mutant 4691 and/or mutant 5251. These acs4 mutants have been described in detail in EP application number 12186606.5. Preferably, said mutations in said acs2 and/or acs4 alleles results in reduced ethylene production and/or slower fruit ripening and/or a longer shelf life of tomato fruits compared to Solanum lycopersicum being homozygous for the functional wild type Acs2 and Acs4 allele (e.g. Pusa Sheetal, Tapa, or TPAADASU) or variants thereof. Such plants may be obtained via breeding methods known in the art by crossing a plant having the desired acs2 mutation with a plant having the desired acs4 mutation. Such plants or plant parts can be homozygous or heterozygous for the acs2 mutation or for the acs4 mutation or for both the acs2 and acs4 mutation. Thus, the plant may genetically be acs2/Acs2 acs4/Acs4 or acs2/acs2 acs4/Acs4 or acs2/Acs2 acs4/acs4 or acs2/acs2 acs4/acs4.

Preferably, the mutant plants also have good other agronomic characteristics, i.e. they do not have reduced fruit numbers and/or reduced fruit quality compared to wild type plants. In a preferred embodiment the plant is a tomato plant and the fruit is a tomato fruit, such as a processing tomato, fresh market tomato of any shape or size or colour. Thus, also harvested products of plants or plant parts comprising one or two mutant acs2 alleles are provided. This includes downstream processed products, such as tomato paste, ketchup, tomato juice, cut tomato fruit, canned fruit, dried fruit, peeled fruit, etc. The products can be identified by comprising the mutant allele in their genomic DNA.

Seed Deposits

A representative sample of seeds of seven (7) tomato TILLING mutants (acs2 mutants) according to Example 1, were deposited by Nunhems B. V. and accepted for deposit on 21 Aug. 2012 at the NCIMB Ltd. (Ferguson Building, Craibstone Estate, Bucksburn Aberdeen, Scotland AB21 9YA, UK) according to the Budapest Treaty, under the Expert Solution (EPC 2000, Rule 32(1)). Seeds were given the following deposit numbers: NCIMB 42032 (mutant 783), NCIMB 42033 (mutant 2145), NCIMB 42035 (mutant 2714), NCIMB 42036 mutant (3793), NCIMB 42040 (mutant 4946), NCIMB 42042 (mutant 7871), or NCIMB 42043 (mutant 8185).

A representative sample of seeds of five tomato TILLING mutants (acs4 mutants) according to Example 1, were deposited by Nunhems B. V. and accepted for deposit on 21 Aug. 2012 at the NCIMB Ltd. (Ferguson Building, Craibstone Estate, Bucksburn Aberdeen, Scotland AB21 9YA, UK) according to the Budapest Treaty, under the Expert Solution (EPC 2000, Rule 32(1)). Seeds were given the following deposit numbers: NCIMB 42034 (mutant 2477), NCIMB 42037 (mutant 4043), NCIMB 42038 (mutant 4222), NCIMB 42039 (mutant 4691), NCIMB 42041 (mutant 5251). These acs4 mutants have been described in European Patent Application number 12186606.5.

The Applicant requests that samples of the biological material and any material derived therefrom be only released to a designated Expert in accordance with Rule 32(1) EPC or related legislation of countries or treaties having similar rules and regulation, until the mention of the grant of the patent, or for 20 years from the date of filing if the application is refused, abandoned, withdrawn or deemed to be withdrawn.

Access to the deposit will be available during the pendency of this application to persons determined by the Director of the U.S. Patent Office to be entitled thereto upon request. Subject to 37 C.F.R. §1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

EXAMPLES

General Methods

PCR amplification products were directly sequenced by a service company (BaseClear, The Netherlands, world wide web at www.basedear.com/) using the same primers as were used for the amplification. The obtained sequences were aligned using a computer program (CLC Bio Main Work Bench, Denmark, world wide web at cicbio.com) to identify the nucleotide changes.

Materials

Water used for analyses and mutagenis is tap water filtered in an Milli-Q water Integral system, Milli-Q type Reference A+ supplied with a Q-gard T2 Cartridge and a Quantum TEX Cartridge. Water resistance is >=18 MOhm.

Ethyl Methanesulfonate (EMS) (pure) was obtained from Sigma, product number M0880.

Measurement of Tomato Ripening and/or Shelf-life Time or Periods

Tomato ripening and/or shelf life time or periods can be measured by various methods known in the art like for example making periodically visual assessments of fruits and/or measurement of fruit firmness or softening, measurement of lycopene contents in the tomato fruits, ethylene production by the fruits, colour of the fruits or any alternative method or combination of methods. Fruit firmness can for example be measured by evaluating resistance to deformation in units of for example 0.1 mm as measured with a penetrometer fitted with a suitable probe (e.g. a probe of 3 mm) (Mutschler et al, 1992, Hortscience 27 pp 352-355) (Martinez et al 1995 Acta Horticulturae 412 pp 463-469). Alternative methods exist in the art, such as use of a texturometer (Bui et al. 2010; International Journal of Food Properties, Volume 13, Issue 4 pp 830 846).

Fruit colour can be classified by the U.S. standards for grades of fresh tomato (U.S. Dept of Agriculture, 1973, US standards for grades of fresh tomatoes, U.S. Dept Agr. Agr. Mktg. Serv., Washington D.C.), measuring the colour with a chromometer (Mutschler et al 1992, Hortscience 27 pp 352-355) or by comparing the colour to a colour chart like the Royal Horticultural Society (RHS) Color Chart (world wide web at rhs.org.uk).

Lycopene content can be determined according to the reduced volumes of organic solvents method of Fish et al. A quantitative assay for lycopene that utilizes reduced volumes of organic solvents. Fish et al. *J. Food Compos. Anal.* 2002, 15, 309-317. This method can be used to determine lycopene content measured directly on intact tomato fruit while simultaneously estimating the basic physicochemical characteristics: color, firmness, soluble solids, acidity, and pH (Clement et al, *J. Agric. Food Chem.* 2008, 56, 9813-9818).

Ethylene release can be measured by placing the fruit in a closed space, e.g. in a 0.5 l glass holder. One ml of holder atmosphere can be extracted after one hour and amount of ethylene gas produced can be quantified using a gas chromatograph (e.g. a Hewlett-Packard 5890) equipped with a suitable detection unit, e.g. a flame ionisation detector, and a suitable column (e.g. a 3 m stainless steel column with an inner diameter of 3.5 mm containing activated alumina of 80/100 mesh). Ethylene production can be expressed as the amount in nl of ethylene given off per gram of fruit per hour (nl g−1 h−1) (Martinez et al 1995 Acta Horticulturae 412 pp 463-469).

Alternatively, ethylene production can be measured as described further below, using real-time measurements with a laser-based ethylene detector (ETD-300, Sensor Sense B. V., Nijmegen, the Netherlands) in combination with a gas handling system (Cristescu et al., 2008 Laser-based systems for trace gas detection in life sciences. Appl Phys B 2008; 92 pp 343-9).

Example 1

Mutagenesis

A highly homozygous inbred line used in commercial processing tomato breeding was used for mutagenesis treatment with the following protocol. After seed imbibition on damp Whatman® paper for 24 h, ~20,000 seeds, divided in 8 batches of 2500 respectively, were soaked in 100 ml of ultrapure water and ethyl methanesulfonate (EMS) at a concentration of 1% in conical flasks. The flasks were gently shaken for 16 h at room temperature. Finally, EMS was rinsed out under flowing water. Following EMS treatment, seeds were directly sown in the greenhouse. Out of the 60% of the seeds that germinated, 10600 plantlets were transplanted in the field. From these 10600 plantlets, 1790 were either sterile or died before producing fruit. For each remaining M1 mutant plant one fruits was harvested and its seeds isolated. The obtained population, named M2 population, is composed of 8810 seeds lots each representing one M2 family. Of these, 585 families were excluded from the population due to low seed set.

DNA was extracted from a pool of 10 seeds originating from each M2 seed lot. Per mutant line, 10 seeds were pooled in a Micronic® deepwell tube; world wide web at micronic.com from a 96 deep-well plate, 2 stainless balls were added to each tube. The tubes and seeds were frozen in liquid nitrogen for 1 minute and seeds were immediately ground to a fine powder in a Deepwell shaker (Vaskon grinder, Belgium; world wide web at vaskon.com) for 2 minutes at 16,8 Hz (80% of the maximum speed). 300 µl Agowa® Lysis buffer P from the AGOWA® Plant DNA Isolation Kit world wide web at agowa.de was added to the sample plate and the powder was suspended in solution by shaking 1 minute at 16,8 Hz in the Deepwell shaker. Plates were centrifuged for 10 minutes at 4000 rpm. 75 µl of the supernatant was pipetted out to a 96 Kingfisher plate using a Janus MDT® (Perkin Elmer, USA; world wide web at perkinelmer.com) platform (96head). The following steps were performed using a Perkin Elmer Janus® liquid handler robot and a 96 Kingfisher® (Thermo labsystems, Finland; world wide web at thermo.com). The supernatant containing the DNA was diluted with binding buffer (150 µl) and magnetic beads (20 IA). Once DNA was bound to the beads, two successive washing steps were carried out (Wash buffer 1: Agowa wash buffer 1 ⅓, ethanol ⅓, isopropanol ⅓; Wash buffer 2: 70% ethanol, 30% Agowa wash buffer 2) and finally eluted in elution buffer (100 µl MQ, 0,025 µl Tween).

Grinding ten *S. lycopersicum* seeds produced enough DNA to saturate the magnetic beads, thus highly homogenous and comparable DNA concentrations of all samples were obtained. Comparing with lambda DNA references, a concentration of 30 ng/µl for each sample was estimated. Two times diluted DNA was 4 fold flat pooled. 2 µl pooled DNA was used in multiplex PCRs for mutation detection analysis.

Primers used to amplify gene fragments for HRM were designed using a computer program (Primer3, world wide web at primer3.sourceforge.net/). The length of the amplification product was limited between 200 and 400 base pairs. Quality of the primers was determined by a test PCR reaction that should yield a single product.

Polymerase Chain Reaction (PCR) to amplify gene fragments. 10 ng of genomic DNA was mixed with 4 µl reaction buffer (5× Reaction Buffer), 2 µl 10×LC dye ((LCGreen+ dye, Idaho Technology Inc., UT, USA), 5 pmole of forward and reverse primers each, 4 nmole dNTPs (Life Technologies, NY, USA) and 1 unit DNA polymerase (Hot Start II DNA Polymerase) in a total volume of 10 µl. Reaction conditions were: 30 s 98° C., then 40 cycles of 10 s. 98° C., 15 s 60° C., 25 s of 72° C. and finally 60 s at 72° C.

High Resolution Melt curve analysis (HRM) has been proven to be sensitive and high-throughput methods in human and plant genetics. HRM is a non-enzymatic screening technique. During the PCR amplification dye (LCGreen+ dye, Idaho Technology Inc., UT, USA) molecules intercalate between each annealed base pair of the double stranded DNA molecule. When captured in the molecule, the dye emits fluorescence at 510 nm after excitation at 470 nm. A camera in a fluorescence detector (LightScanner, Idaho Technology Inc., UT, USA) records the fluorescence intensity while the DNA sample is progressively heated. At a temperature dependent on the sequence specific stability of the DNA helices, the double stranded PCR product starts to melt, releasing the dye. The release of dye results in decreased fluorescence that is recorded as a melting curve by the fluorescence detector. Pools containing a mutation form hetero duplexes in the post-PCR fragment mix. These are identified as differential melting temperature curves in comparison to homo duplexes.

The presence of the particular mutation in individual plants was confirmed repeating the HRM analysis on DNA from the individual M2 seed lots of the identified corresponding DNA pool. When the presence of the mutation, based on the HRM profile, was confirmed in one of the four individual M2 family DNA samples, the PCR fragments were sequenced to identify the mutation in the gene.

Once the mutation was known the effect of such an mutation was predicted using a computer program CODDLe (for Choosing codons to Optimize Discovery of Deleterious Lesions, world wide web at proweb.org/coddle/) that identifies the region(s) of a user-selected gene and of its coding sequence where the anticipated point mutations are most likely to result in deleterious effects on the gene's function.

Seeds from M2 families that contain mutations with predicted effect on protein activity were sown for phenotypic analysis of the plants.

Homozygous mutants were selected or obtained after selling and subsequent selection. The effect of the mutation on the corresponding protein and phenotype of the plant was determined.

Seeds containing the different identified mutations were germinated and plants were grown in pots with soil the greenhouse with 16/8 light dark regime and 18° C. night and 22-25° C. day temperature. For each genotype 5 plants were raised. The second, third and fourth inflorescence were used for the analysis. The inflorescences were pruned leaving six flowers per inflorescence that were allowed to set fruit by self-pollination. The dates of fruit set of the first and sixth flower was recorded as was the date of breaker and red stage of the first and sixth fruit. At breaker of the sixth fruit the truss was harvested and stored in an open box in the greenhouse. Condition of the fruits was recorded during the whole ripening period.

At later stages fruit condition was determined based on visual assessment of the fruits and the date when the oldest fruit became 'bad' was recorded and further fruit deterioration was recorded (indicated by further fruit softness assessed by pinching the fruits, and visual assessment of dehydration/water loss, breaking of the skin and fungal growth).

The following mutants were identified: mutant 783, mutant 2145, mutant 2714, mutant 3793, mutant 4946, mutant 7871, and mutant 8185, and seeds were deposited at the NCIMB under the Accession numbers given above.

The mutations in the nucleotide sequence compared to the cDNA of wild type Acs2 as depicted in SEQ ID NO 9, and its effect on the protein sequence of each mutant has been described above.

Plants comprising mutations in the target sequence, such as the above mutant plants or plants derived therefrom (e.g. by selfing or crossing) and comprising the mutant acs2 allele, show a normal vegetative growth of all plant parts when compared to wild-type plants except for the ripening of the tomato fruits. The plants comprising mutations in the target sequence were screened phenotypically for their fruit ripening, ethylene production and shelf live.

Example 2

Ripening Behaviour of the Acs2 Mutants

Seeds containing the different mutations were germinated and plants were grown in pots with soil the greenhouse with 16/8 light dark regime and 18° C. night and 22-25° C. day temperature. For each genotype 5 plants were raised. The second, third and fourth inflorescence were used for the analysis. The inflorescences were pruned, leaving six flowers per inflorescence that were allowed to set fruit by self-pollination. The dates of fruit set of the first and sixth flower was recorded as was the date of breaker and red stage of the first and sixth fruit. At red stage of the 4$^{th}$ fruit the truss was harvested and stored in an open box in the greenhouse. Condition of the fruits was recorded during the whole ripening period by making pictures from each truss. After harvest pictures were made per box containing all trusses from one genotype.

At later stages fruit condition was determined based on visual assessment of the fruits and the date when the oldest fruit became 'bad' was recorded and further fruit deterioration was recorded (indicated by further fruit softness assessed by pinching the fruits, and visual assessment of dehydration/water loss, breaking of the skin and fungal growth).

The ripening behaviour of the fruits is shown in FIG. 2. The day on which the first fruit of the wild type plant came into breaker stage was taken as day 1. The days thereafter were numbered as consecutive days. Mutants show a delay in ripening, i.e. fruits of the mutants require more days to become red and/or become "bad". Especially mutant 3793 and 2714 show a significant delay of several days. Mutant 3793 shows that it takes more time for this mutant to go from first fruit in breaker stage to 100% fruit in red stage.

A characteristic of fruits of the plants of the invention is that breaker stage starts later (e.g. mutant 783, 2145, 2714, 3793). Post-harvest characteristics are shown below. The day on which the first fruit of the wild type plant came into breaker stage was taken as day 1. The days thereafter were numbered as consecutive days.

Example 3

Ethylene Release

Ethylene released by tomato fruits was measured in real-time with a laser-based ethylene detector (ETD-300, Sensor Sense B. V., Nijmegen, the Netherlands) in combination with a gas handling system (Cristescu et al., Laser-based systems for trace gas detection in life sciences. Appl Phys B 2008; 92 pp 343-9). Six glass cuvettes (100 mL volume) were used per experiment, one as a reference without plant material. Air was sampled from the lab and passed through a platinum based catalyzer (Sensor Sense B. V., Nijmegen, the Netherlands) to remove traces of ethylene or other hydrocarbons. Between the sample and the detector scrubbers with KOH and CaCl2 were placed to reduce the CO2 concentration (to less than 1 ppm) and decrease the water content in the gas flow, respectively.

Comparison of the ethylene released from fruits of mutant 2145, 2714, 3793, 4946, 7871, and 8185 with wild type (Tapa) at pink stage and red stage (as shown in FIG. 1) revealed that the ethylene production of all mutants had reduced compared to wild type (Tapa) in at least one of these stages. Tapa is a highly homozygous inbred parental line used in commercial processing tomato (TPAADASU in Gady et al, 2012 Molecular Breeding 29 pp 801-812) and is homozygous for the wild type Acs2 allele (Acs2/Acs2). Mutant 2145, 3793, and 4946 produced less ethylene compared to Tapa in both stages whereas mutant 2714 and 8185 only in pink, and 7871 only in red stage.

At pink stage mutant 2145 produced about 14% less ethylene than wild type, mutant 2714 produced about 5% less ethylene than wild type, mutants 3793, and 8185 produced between about 39 and about 47% less ethylene than wild type. Mutant 4946 produced about 80% less ethylene at pink stage compared to wild-type: <about 1.0 nl/(h·g) versus about 4.8 nl/(h·g) for the wild type. While in red stage mutants 2714 and 8185 produce about 14 and 12%, respectively more ethylene than wild type. Mutant 3793 produced at red stage about 8% less ethylene than wild type, mutants 7871, 2145, and 4946 produced about 29, 33, 40%, less ethylene than wild type, respectively. Wherein nl/(h·g) means nano liter per hour per gram of fruit.

Example 4

Tomato Fruit Firmness/Compression Test

Seeds of mutant 8185 lines were sown and 6 plants were gown from February to September in 5 L pots under standard greenhouse conditions. Per plant three clusters of tomatoes were selected and labeled. From each fruit cluster the 3rd and 4th tomato were selected for fruit development and softening analysis during the ripening process. In total

|         | First fruit in Breaker stage | All Fruits in Breaker stage | First Fruit in red stage | All fruits in red stage | First fruits in "bad" stage |
|---------|------------------------------|------------------------------|---------------------------|-------------------------|------------------------------|
| Wt      | 1                            | 25                           | 4                         | 29                      | 42                           |
| 783 Ho  | 8                            | 18                           | 14                        | 22                      | 49                           |
| 2145 Ho | 4                            | 22                           | 8                         | 22                      | >51                          |
| 2714 Ho | 4                            | 25                           | 23                        | 29                      | >51                          |
| 3793 Ho | 4                            | 35                           | 8                         | 39                      | >51                          |

As can be seen, mutant fruits enter breaker stage later. Equally, mutant fruits come into the red stage later and the date when the first fruits of a mutant line are in "bad" stage is also significantly later than for the wild type.

six tomatoes per plant where used for the analysis. Date of the breaker, yellow/pink, and full red stage were noted for each tomato. Stages were defined based on United States Standards for Grade of Fresh Tomatoes (USDA; 1997, US department of Agriculture, Agricultural Marketing, Service, Washington, D.C. Tomato ripening stage was determined by the tomato color (RHS color chart). Mature green, 144B; Breaker, N144D; Orange, N163C/D; Red, 44A/B; Overripe (bad) N34A and 46A).

Tomatoes that entered the full red stage (day 0) were labeled and, either picked from the plant for analysis, or left on the plant to be analyzed at later time point. In the latter case fruits that remained on the plant were picked at day 3, 7, 10, 14 or 18 after full red for analysis. Thus 6 fruits were picked at each time point. Harvested tomatoes were stored at 22° C. after measurements. Fruit firmness was measured with a texturometer (Compressor/load frame Instron, http://www.instron.us, System ID: 3342L2018; Force Transducer model 2519-104) controlled by a computer running Bluehill 3 program (Instron).

Firmness of tomatoes was measured according a method developed by Sirisomboon and Tanaka (Panmanas Sirisomboon, Munehiro Tanaka, Takayuki Kojima 2012 Evaluation of tomato textural mechanical properties. J Food Engineering 111, 618-624) adjusted to our preferences. The fruit was compressed between two steel plates (the upper one is the load cell plateau) moving with 1 mm per second generating an incremental force until 4 Newton was reached. This force was empirically determined as a high enough to generate quantifiable fruit compression without damaging the fruit tissue, also allowing repetitive measurements. Immediately thereafter the pressure was released to 0.1N. Then pressure was increased again until 4N was measured. The average deformation (Day) during the force increment from 0.1N to 4N was calculated from the two measurements (Day/3.9 (mm/N)). As fruits differ in size a deformation was calculated relative to the fruit diameter (Drel=Dav/Fruit diameter (mm/(N·cm)). The firmness of a fruit was expressed as the force necessary to decrease the fruit diameter 1 mm per cm fruit (10%) (Firmness=1/Drel (N)).

Day=0 equals to the day at which the fruits were harvested and measured for the first time. So, the same fruits were measured 4 times to obtain data points at 7, 7, 14 and 21 days. Fruit firmness measurement shows that mutant 8185 has a higher fruit firmness especially at about 7, 14, and/or 21 days where fruits of mutant 8185 require about 1 N more to decrease the fruit diameter 1 mm per cm fruit (10%).

The invention claimed is:

1. A plant, fruit, seed, or part thereof of the species *Solanum lycopersicum* comprising an acs2 allele having one or more mutations, said mutations resulting in production of a mutant acs2 protein, wherein said mutant acs2 protein has one or more amino acids comprising A101V or V147E, the amino acid positions corresponding to SEQ ID NO: 1,
wherein said one or more mutations results in reduced ethylene production and/or delayed fruit ripening and/or a longer shelf life compared to *Solanum lycopersicum* being homozygous for the wild type Acs2 allele encoding a wild type Acs2 protein, said wild type Acs2 protein comprises at least 95% amino acid sequence identity to SEQ ID NO: 1.

2. The plant, fruit, seed, or part thereof of claim 1, wherein said one or more mutations results in production of a mutant acs2 protein having loss-of-function or reduced function compared to said wild type Acs2 protein.

3. The plant, fruit, seed, or part thereof according to claim 1, wherein said mutation or mutations result in the tomato fruits requiring at least 2 days longer for 10% of fruits to reach the red stage compared to *Solanum lycopersicum* being homozygous for the wild type Acs2 allele encoding said wild type Acs2 protein.

4. The plant, fruit, seed, or part thereof according to claim 1, wherein said mutation or mutations result in the tomato fruits requiring at least 1 day longer to pass the fully ripe stage compared to *Solanum lycopersicum* being homozygous for the wild type Acs2 allele encoding said wild type Acs2 protein.

5. The plant, fruit, seed, or part thereof according to claim 1, wherein said one or more mutations results in the tomato fruits of said plant having at least a 10% reduced ethylene production compared to *Solanum lycopersicum* being homozygous for the wild type Acs2 allele encoding said wild type Acs2 protein.

6. The plant according to claim 1, wherein the plant is an F1 hybrid plant.

7. The plant, fruit, seed, or part thereof according to claim 1, wherein the acs2 allele having one or more mutations, is in homozygous form.

8. The plant, fruit, seed, or part thereof according to claim 1, wherein the plant additionally comprises an acs4 allele having one or more mutations, said mutations in said acs4 allele resulting in production of a mutant acs4 protein having loss-of-function or reduced function compared to wild type Acs4 protein, said wild type Acs4 protein comprises at least 85% amino acid sequence identity to SEQ ID NO: 25.

9. Seed from which the plant according to claim 1 can be grown.

10. Tomato fruit or parts thereof, seeds, pollen, plant parts, or progeny of the plant of claim 1 comprising an acs2 protein having one or more mutations comprising A101V or V147E, the amino acid positions corresponding to SEQ ID NO:1, wherein said one or more mutations results in reduced ethylene production and/or delayed fruit ripening and/or a longer shelf life compared to *Solanum lycopersicum* being homozygous for the wild type Acs2 allele encoding a wild type Acs2 protein, said wild type Acs2 protein comprises at least 95% amino acid sequence identity to SEQ ID NO: 1.

11. The fruit according to claim 10, wherein the shelf life is at least 2 days longer than the shelf life of a tomato fruit being homozygous for the wild type Acs2 allele.

12. The fruit according to claim 10, wherein the reduced ethylene production is at least 10% reduced compared to *Solanum lycopersicum* being homozygous for the wild type Acs2 allele.

13. The plant according to claim 5, wherein the reduced ethylene production is determined in the pink and/or red stage of the fruit.

14. Food or food products comprising of the fruit or parts thereof according to claim 10.

15. The fruit according to claim 12, wherein the reduced ethylene production is determined in the pink and/or red stage of the fruit.

16. A method for producing a hybrid *Solanum lycopersicum* plant comprising:
   crossing the *Solanum lycopersicum* plant of claim 1 with a second *Solanum lycopersicum* plant to obtain hybrid seeds, wherein said hybrid seeds produce a hybrid *Solanum lycopersicum* plant comprising an acs2 allele having one or more mutations, said mutations resulting in production of a mutant acs2 protein, wherein said mutant acs2 protein has one or more amino acids comprising A101V or V147E, the amino acid positions corresponding to SEQ ID NO:1,
   wherein said one or more mutations results in reduced ethylene production and/or delayed fruit ripening and/or a longer shelf life compared to *Solanum lycopersicum* being homozygous for the wild type Acs2 allele encoding a wild type Acs2 protein, said wild type Acs2 protein comprises at least 95% amino acid sequence identity to SEQ ID NO: 1.

17. The plant, fruit, seed, or part thereof according claim 8, wherein said mutant acs4 allele is obtained from NCIMB Accession No. 42034, 42037, 42038, 42039 or 42041.

18. The plant, fruit, seed, or part thereof of claim 1, wherein the plant is a variety, breeding line or cultivar.

19. The plant, fruit, seed, or part thereof of claim 1, wherein said mutant acs2 protein comprises V147E.

20. The plant, fruit, seed, or part thereof of claim 1, wherein said mutant acs2 protein comprises A101V.

21. The plant, fruit, seed, or part thereof of claim 18, wherein said mutant acs2 protein comprises V147E.

22. The plant, fruit, seed, or part thereof of claim 18, wherein said mutant acs2 protein comprises A101V.

* * * * *

SEQUENCE LISTING

```
<160> NUMBER OF SEQ ID NOS: 31

<210> SEQ ID NO 1
<211> LENGTH: 485
<212> TYPE: PRT
<213> ORGANISM: Lycopersicon esculentum

<400> SEQUENCE: 1

Met Gly Phe Glu Ile Ala Lys Thr Asn Ser Ile Leu Ser Lys Leu Ala
1               5                   10                  15

Thr Asn Glu Glu His Gly Glu Asn Ser Pro Tyr Phe Asp Gly Trp Lys
            20                  25                  30

Ala Tyr Asp Ser Asp Pro Phe His Pro Leu Lys Asn Pro Asn Gly Val
        35                  40                  45

Ile Gln Met Gly Leu Ala Glu Asn Gln Leu Cys Leu Asp Leu Ile Glu
    50                  55                  60

Asp Trp Ile Lys Arg Asn Pro Lys Gly Ser Ile Cys Ser Glu Gly Ile
65                  70                  75                  80

Lys Ser Phe Lys Ala Ile Ala Asn Phe Gln Asp Tyr His Gly Leu Pro
                85                  90                  95

Glu Phe Arg Lys Ala Ile Ala Lys Phe Met Glu Lys Thr Arg Gly Gly
            100                 105                 110

Arg Val Arg Phe Asp Pro Glu Arg Val Val Met Ala Gly Gly Ala Thr
        115                 120                 125

Gly Ala Asn Glu Thr Ile Ile Phe Cys Leu Ala Asp Pro Gly Asp Ala
    130                 135                 140

Phe Leu Val Pro Ser Pro Tyr Tyr Pro Ala Phe Asn Arg Asp Leu Arg
145                 150                 155                 160

Trp Arg Thr Gly Val Gln Leu Ile Pro Ile His Cys Glu Ser Ser Asn
                165                 170                 175

Asn Phe Lys Ile Thr Ser Lys Ala Val Lys Glu Ala Tyr Glu Asn Ala
            180                 185                 190

Gln Lys Ser Asn Ile Lys Val Lys Gly Leu Ile Leu Thr Asn Pro Ser
        195                 200                 205

Asn Pro Leu Gly Thr Thr Leu Asp Lys Asp Thr Leu Lys Ser Val Leu
    210                 215                 220
```

-continued

Ser Phe Thr Asn Gln His Asn Ile His Leu Val Cys Asp Glu Ile Tyr
225                 230                 235                 240

Ala Ala Thr Val Phe Asp Thr Pro Gln Phe Val Ser Ile Ala Glu Ile
                245                 250                 255

Leu Asp Glu Gln Glu Met Thr Tyr Cys Asn Lys Asp Leu Val His Ile
            260                 265                 270

Val Tyr Ser Leu Ser Lys Asp Met Gly Leu Pro Gly Phe Arg Val Gly
        275                 280                 285

Ile Ile Tyr Ser Phe Asn Asp Asp Val Val Asn Cys Ala Arg Lys Met
    290                 295                 300

Ser Ser Phe Gly Leu Val Ser Thr Gln Thr Gln Tyr Phe Leu Ala Ala
305                 310                 315                 320

Met Leu Ser Asp Glu Lys Phe Val Asp Asn Phe Leu Arg Glu Ser Ala
                325                 330                 335

Met Arg Leu Gly Lys Arg His Lys His Phe Thr Asn Gly Leu Glu Val
            340                 345                 350

Val Gly Ile Lys Cys Leu Lys Asn Asn Ala Gly Leu Phe Cys Trp Met
        355                 360                 365

Asp Leu Arg Pro Leu Leu Arg Glu Ser Thr Phe Asp Ser Glu Met Ser
    370                 375                 380

Leu Trp Arg Val Ile Ile Asn Asp Val Lys Leu Asn Val Ser Pro Gly
385                 390                 395                 400

Ser Ser Phe Glu Cys Gln Glu Pro Gly Trp Phe Arg Val Cys Phe Ala
                405                 410                 415

Asn Met Asp Asp Gly Thr Val Asp Ile Ala Leu Ala Arg Ile Arg Arg
            420                 425                 430

Phe Val Gly Val Glu Lys Ser Gly Asp Lys Ser Ser Met Glu Gln
        435                 440                 445

Lys Gln Gln Trp Lys Lys Asn Asn Leu Arg Leu Ser Phe Ser Lys Arg
    450                 455                 460

Met Tyr Asp Glu Ser Val Leu Ser Pro Leu Ser Ser Pro Ile Pro Pro
465                 470                 475                 480

Ser Pro Leu Val Arg
                485

<210> SEQ ID NO 2
<211> LENGTH: 485
<212> TYPE: PRT
<213> ORGANISM: Lycopersicon esculentum

<400> SEQUENCE: 2

Met Gly Phe Glu Ile Ala Lys Thr Asn Ser Ile Leu Ser Lys Leu Ala
1               5                   10                  15

Thr Asn Glu Glu His Gly Glu Asn Ser Pro Tyr Phe Asp Gly Trp Lys
                20                  25                  30

Ala Tyr Asp Ser Asp Pro Phe His Pro Leu Lys Asn Pro Asn Gly Val
            35                  40                  45

Ile Gln Met Gly Leu Ala Glu Asn Gln Leu Cys Leu Asp Leu Ile Glu
        50                  55                  60

Asp Trp Ile Lys Arg Asn Pro Lys Gly Ser Ile Cys Ser Glu Gly Ile
65                  70                  75                  80

Lys Ser Phe Lys Ala Ile Ala Asn Phe Gln Asp Tyr His Gly Leu Pro
                85                  90                  95

Glu Phe Arg Lys Ala Ile Thr Lys Phe Met Glu Lys Thr Arg Gly Gly

```
            100                 105                 110
Arg Val Arg Phe Asp Pro Glu Arg Val Val Met Ala Gly Gly Ala Thr
        115                 120                 125
Gly Ala Asn Glu Thr Ile Ile Phe Cys Leu Ala Asp Pro Gly Asp Ala
    130                 135                 140
Phe Leu Val Pro Ser Pro Tyr Tyr Pro Ala Phe Asn Arg Asp Leu Arg
145                 150                 155                 160
Trp Arg Thr Gly Val Gln Leu Ile Pro Ile His Cys Glu Ser Ser Asn
                165                 170                 175
Asn Phe Lys Ile Thr Ser Lys Ala Val Lys Glu Ala Tyr Glu Asn Ala
            180                 185                 190
Gln Lys Ser Asn Ile Lys Val Lys Gly Leu Ile Leu Thr Asn Pro Ser
        195                 200                 205
Asn Pro Leu Gly Thr Thr Leu Asp Lys Asp Thr Leu Lys Ser Val Leu
    210                 215                 220
Ser Phe Thr Asn Gln His Asn Ile His Leu Val Cys Asp Glu Ile Tyr
225                 230                 235                 240
Ala Ala Thr Val Phe Asp Thr Pro Gln Phe Val Ser Ile Ala Glu Ile
                245                 250                 255
Leu Asp Glu Gln Glu Met Thr Tyr Cys Asn Lys Asp Leu Val His Ile
            260                 265                 270
Val Tyr Ser Leu Ser Lys Asp Met Gly Leu Pro Gly Phe Arg Val Gly
        275                 280                 285
Ile Ile Tyr Ser Phe Asn Asp Asp Val Val Asn Cys Ala Arg Lys Met
    290                 295                 300
Ser Ser Phe Gly Leu Val Ser Thr Gln Thr Gln Tyr Phe Leu Ala Ala
305                 310                 315                 320
Met Leu Ser Asp Glu Lys Phe Val Asp Asn Phe Leu Arg Glu Ser Ala
                325                 330                 335
Met Arg Leu Gly Lys Arg His Lys His Phe Thr Asn Gly Leu Glu Val
            340                 345                 350
Val Gly Ile Lys Cys Leu Lys Asn Asn Ala Gly Leu Phe Cys Trp Met
        355                 360                 365
Asp Leu Arg Pro Leu Leu Arg Glu Ser Thr Phe Asp Ser Glu Met Ser
    370                 375                 380
Leu Trp Arg Val Ile Ile Asn Asp Val Lys Leu Asn Val Ser Pro Gly
385                 390                 395                 400
Ser Ser Phe Glu Cys Gln Glu Pro Gly Trp Phe Arg Val Cys Phe Ala
                405                 410                 415
Asn Met Asp Asp Gly Thr Val Asp Ile Ala Leu Ala Arg Ile Arg Arg
            420                 425                 430
Phe Val Gly Val Glu Lys Ser Gly Asp Lys Ser Ser Met Glu Gln
        435                 440                 445
Lys Gln Gln Trp Lys Lys Asn Asn Leu Arg Leu Ser Phe Ser Lys Arg
    450                 455                 460
Met Tyr Asp Glu Ser Val Leu Ser Pro Leu Ser Ser Pro Ile Pro Pro
465                 470                 475                 480
Ser Pro Leu Val Arg
                485

<210> SEQ ID NO 3
<211> LENGTH: 485
<212> TYPE: PRT
<213> ORGANISM: Lycopersicon esculentum
```

<400> SEQUENCE: 3

Met Gly Phe Glu Ile Ala Lys Thr Asn Ser Ile Leu Ser Lys Leu Ala
1               5                   10                  15

Thr Asn Glu Glu His Gly Glu Asn Ser Pro Tyr Phe Asp Gly Trp Lys
            20                  25                  30

Ala Tyr Asp Ser Asp Pro Phe His Pro Leu Lys Asn Pro Asn Gly Val
        35                  40                  45

Ile Gln Met Gly Leu Ala Glu Asn Gln Leu Cys Leu Asp Leu Ile Glu
    50                  55                  60

Asp Trp Ile Lys Arg Asn Pro Lys Gly Ser Ile Cys Ser Glu Gly Ile
65                  70                  75                  80

Lys Ser Phe Lys Ala Ile Ala Asn Phe Gln Asp Tyr His Gly Leu Pro
                85                  90                  95

Glu Phe Arg Lys Ala Ile Ala Lys Phe Met Glu Lys Thr Arg Gly Arg
            100                 105                 110

Arg Val Arg Phe Asp Pro Glu Arg Val Val Met Ala Gly Gly Ala Thr
        115                 120                 125

Gly Ala Asn Glu Thr Ile Ile Phe Cys Leu Ala Asp Pro Gly Asp Ala
    130                 135                 140

Phe Leu Val Pro Ser Pro Tyr Tyr Pro Ala Phe Asn Arg Asp Leu Arg
145                 150                 155                 160

Trp Arg Thr Gly Val Gln Leu Ile Pro Ile His Cys Glu Ser Ser Asn
                165                 170                 175

Asn Phe Lys Ile Thr Ser Lys Ala Val Lys Glu Ala Tyr Glu Asn Ala
            180                 185                 190

Gln Lys Ser Asn Ile Lys Val Lys Gly Leu Ile Leu Thr Asn Pro Ser
        195                 200                 205

Asn Pro Leu Gly Thr Thr Leu Asp Lys Asp Thr Leu Lys Ser Val Leu
    210                 215                 220

Ser Phe Thr Asn Gln His Asn Ile His Leu Val Cys Asp Glu Ile Tyr
225                 230                 235                 240

Ala Ala Thr Val Phe Asp Thr Pro Gln Phe Val Ser Ile Ala Glu Ile
                245                 250                 255

Leu Asp Glu Gln Glu Met Thr Tyr Cys Asn Lys Asp Leu Val His Ile
            260                 265                 270

Val Tyr Ser Leu Ser Lys Asp Met Gly Leu Pro Gly Phe Arg Val Gly
        275                 280                 285

Ile Ile Tyr Ser Phe Asn Asp Asp Val Val Asn Cys Ala Arg Lys Met
    290                 295                 300

Ser Ser Phe Gly Leu Val Ser Thr Gln Thr Gln Tyr Phe Leu Ala Ala
305                 310                 315                 320

Met Leu Ser Asp Glu Lys Phe Val Asp Asn Phe Leu Arg Glu Ser Ala
                325                 330                 335

Met Arg Leu Gly Lys Arg His Lys His Phe Thr Asn Gly Leu Glu Val
            340                 345                 350

Val Gly Ile Lys Cys Leu Lys Asn Asn Ala Gly Leu Phe Cys Trp Met
        355                 360                 365

Asp Leu Arg Pro Leu Leu Arg Glu Ser Thr Phe Asp Ser Glu Met Ser
    370                 375                 380

Leu Trp Arg Val Ile Ile Asn Asp Val Lys Leu Asn Val Ser Pro Gly
385                 390                 395                 400

Ser Ser Phe Glu Cys Gln Glu Pro Gly Trp Phe Arg Val Cys Phe Ala

```
            405                 410                 415
Asn Met Asp Asp Gly Thr Val Asp Ile Ala Leu Ala Arg Ile Arg Arg
            420                 425                 430

Phe Val Gly Val Glu Lys Ser Gly Asp Lys Ser Ser Met Glu Gln
            435                 440                 445

Lys Gln Gln Trp Lys Lys Asn Asn Leu Arg Leu Ser Phe Ser Lys Arg
    450                 455                 460

Met Tyr Asp Glu Ser Val Leu Ser Pro Leu Ser Ser Pro Ile Pro Pro
465                 470                 475                 480

Ser Pro Leu Val Arg
            485

<210> SEQ ID NO 4
<211> LENGTH: 485
<212> TYPE: PRT
<213> ORGANISM: Lycopersicon esculentum

<400> SEQUENCE: 4

Met Gly Phe Glu Ile Ala Lys Thr Asn Ser Ile Leu Ser Lys Leu Ala
1               5                   10                  15

Thr Asn Glu Glu His Gly Glu Asn Ser Pro Tyr Phe Asp Gly Trp Lys
            20                  25                  30

Ala Tyr Asp Ser Asp Pro Phe His Pro Leu Lys Asn Pro Asn Gly Val
        35                  40                  45

Ile Gln Met Gly Leu Ala Glu Asn Gln Leu Cys Leu Asp Leu Ile Glu
    50                  55                  60

Asp Trp Ile Lys Arg Asn Pro Lys Gly Ser Ile Cys Ser Glu Gly Ile
65                  70                  75                  80

Lys Ser Phe Lys Ala Ile Ala Asn Phe Gln Asp Tyr His Gly Leu Pro
                85                  90                  95

Glu Phe Arg Lys Ala Ile Ala Lys Phe Met Glu Lys Thr Arg Gly Gly
            100                 105                 110

Arg Val Arg Phe Asp Leu Glu Arg Val Val Met Ala Gly Gly Ala Thr
        115                 120                 125

Gly Ala Asn Glu Thr Ile Ile Phe Cys Leu Ala Asp Pro Gly Asp Ala
    130                 135                 140

Phe Leu Val Pro Ser Pro Tyr Tyr Pro Ala Phe Asn Arg Asp Leu Arg
145                 150                 155                 160

Trp Arg Thr Gly Val Gln Leu Ile Pro Ile His Cys Glu Ser Ser Asn
                165                 170                 175

Asn Phe Lys Ile Thr Ser Lys Ala Val Lys Glu Ala Tyr Glu Asn Ala
            180                 185                 190

Gln Lys Ser Asn Ile Lys Val Lys Gly Leu Ile Leu Thr Asn Pro Ser
        195                 200                 205

Asn Pro Leu Gly Thr Thr Leu Asp Lys Asp Thr Leu Lys Ser Val Leu
    210                 215                 220

Ser Phe Thr Asn Gln His Asn Ile His Leu Val Cys Asp Glu Ile Tyr
225                 230                 235                 240

Ala Ala Thr Val Phe Asp Thr Pro Gln Phe Val Ser Ile Ala Glu Ile
                245                 250                 255

Leu Asp Glu Gln Glu Met Thr Tyr Cys Asn Lys Asp Leu Val His Ile
            260                 265                 270

Val Tyr Ser Leu Ser Lys Asp Met Gly Leu Pro Gly Phe Arg Val Gly
        275                 280                 285
```

```
Ile Ile Tyr Ser Phe Asn Asp Asp Val Val Asn Cys Ala Arg Lys Met
    290                 295                 300

Ser Ser Phe Gly Leu Val Ser Thr Gln Thr Gln Tyr Phe Leu Ala Ala
305                 310                 315                 320

Met Leu Ser Asp Glu Lys Phe Val Asp Asn Phe Leu Arg Ser Ala
                325                 330                 335

Met Arg Leu Gly Lys Arg His Lys His Phe Thr Asn Gly Leu Glu Val
                340                 345                 350

Val Gly Ile Lys Cys Leu Lys Asn Asn Ala Gly Leu Phe Cys Trp Met
        355                 360                 365

Asp Leu Arg Pro Leu Leu Arg Glu Ser Thr Phe Asp Ser Glu Met Ser
    370                 375                 380

Leu Trp Arg Val Ile Ile Asn Asp Val Lys Leu Asn Val Ser Pro Gly
385                 390                 395                 400

Ser Ser Phe Glu Cys Gln Glu Pro Gly Trp Phe Arg Val Cys Phe Ala
                405                 410                 415

Asn Met Asp Asp Gly Thr Val Asp Ile Ala Leu Ala Arg Ile Arg Arg
                420                 425                 430

Phe Val Gly Val Glu Lys Ser Gly Asp Lys Ser Ser Met Glu Gln
                435                 440                 445

Lys Gln Gln Trp Lys Lys Asn Asn Leu Arg Leu Ser Phe Ser Lys Arg
450                 455                 460

Met Tyr Asp Glu Ser Val Leu Ser Pro Leu Ser Ser Pro Ile Pro Pro
465                 470                 475                 480

Ser Pro Leu Val Arg
                485

<210> SEQ ID NO 5
<211> LENGTH: 485
<212> TYPE: PRT
<213> ORGANISM: Lycopersicon esculentum

<400> SEQUENCE: 5

Met Gly Phe Glu Ile Ala Lys Thr Asn Ser Ile Leu Ser Lys Leu Ala
1               5                   10                  15

Thr Asn Glu Glu His Gly Glu Asn Ser Pro Tyr Phe Asp Gly Trp Lys
                20                  25                  30

Ala Tyr Asp Ser Asp Pro Phe His Pro Leu Lys Asn Pro Asn Gly Val
            35                  40                  45

Ile Gln Met Gly Leu Ala Glu Asn Gln Leu Cys Leu Asp Leu Ile Glu
        50                  55                  60

Asp Trp Ile Lys Arg Asn Pro Lys Gly Ser Ile Cys Ser Glu Gly Ile
65                  70                  75                  80

Lys Ser Phe Lys Ala Ile Ala Asn Phe Gln Asp Tyr His Gly Leu Pro
                85                  90                  95

Glu Phe Arg Lys Val Ile Ala Lys Phe Met Glu Lys Thr Arg Gly Gly
                100                 105                 110

Arg Val Arg Phe Asp Pro Glu Arg Val Val Met Ala Gly Gly Ala Thr
            115                 120                 125

Gly Ala Asn Glu Thr Ile Ile Phe Cys Leu Ala Asp Pro Gly Asp Ala
        130                 135                 140

Phe Leu Val Pro Ser Pro Tyr Tyr Pro Ala Phe Asn Arg Asp Leu Arg
145                 150                 155                 160

Trp Arg Thr Gly Val Gln Leu Ile Pro Ile His Cys Glu Ser Ser Asn
                165                 170                 175
```

```
Asn Phe Lys Ile Thr Ser Lys Ala Val Lys Glu Ala Tyr Glu Asn Ala
            180                 185                 190

Gln Lys Ser Asn Ile Lys Val Lys Gly Leu Ile Leu Thr Asn Pro Ser
        195                 200                 205

Asn Pro Leu Gly Thr Thr Leu Asp Lys Asp Thr Leu Lys Ser Val Leu
210                 215                 220

Ser Phe Thr Asn Gln His Asn Ile His Leu Val Cys Asp Glu Ile Tyr
225                 230                 235                 240

Ala Ala Thr Val Phe Asp Thr Pro Gln Phe Val Ser Ile Ala Glu Ile
                245                 250                 255

Leu Asp Glu Gln Glu Met Thr Tyr Cys Asn Lys Asp Leu Val His Ile
            260                 265                 270

Val Tyr Ser Leu Ser Lys Asp Met Gly Leu Pro Gly Phe Arg Val Gly
        275                 280                 285

Ile Ile Tyr Ser Phe Asn Asp Asp Val Val Asn Cys Ala Arg Lys Met
    290                 295                 300

Ser Ser Phe Gly Leu Val Ser Thr Gln Thr Gln Tyr Phe Leu Ala Ala
305                 310                 315                 320

Met Leu Ser Asp Glu Lys Phe Val Asp Asn Phe Leu Arg Glu Ser Ala
                325                 330                 335

Met Arg Leu Gly Lys Arg His Lys His Phe Thr Asn Gly Leu Glu Val
            340                 345                 350

Val Gly Ile Lys Cys Leu Lys Asn Asn Ala Gly Leu Phe Cys Trp Met
        355                 360                 365

Asp Leu Arg Pro Leu Leu Arg Glu Ser Thr Phe Asp Ser Glu Met Ser
    370                 375                 380

Leu Trp Arg Val Ile Ile Asn Asp Val Lys Leu Asn Val Ser Pro Gly
385                 390                 395                 400

Ser Ser Phe Glu Cys Gln Glu Pro Gly Trp Phe Arg Val Cys Phe Ala
                405                 410                 415

Asn Met Asp Asp Gly Thr Val Asp Ile Ala Leu Ala Arg Ile Arg Arg
            420                 425                 430

Phe Val Gly Val Glu Lys Ser Gly Asp Lys Ser Ser Met Glu Gln
        435                 440                 445

Lys Gln Gln Trp Lys Lys Asn Asn Leu Arg Leu Ser Phe Ser Lys Arg
    450                 455                 460

Met Tyr Asp Glu Ser Val Leu Ser Pro Leu Ser Ser Pro Ile Pro Pro
465                 470                 475                 480

Ser Pro Leu Val Arg
            485

<210> SEQ ID NO 6
<211> LENGTH: 485
<212> TYPE: PRT
<213> ORGANISM: Lycopersicon esculentum

<400> SEQUENCE: 6

Met Gly Phe Glu Ile Ala Lys Thr Asn Ser Ile Leu Ser Lys Leu Ala
1               5                   10                  15

Thr Asn Glu Glu His Gly Glu Asn Ser Pro Tyr Phe Asp Gly Trp Lys
            20                  25                  30

Ala Tyr Asp Ser Asp Pro Phe His Pro Leu Lys Asn Pro Asn Gly Val
        35                  40                  45

Ile Gln Met Gly Leu Ala Glu Asn Gln Leu Cys Leu Asp Leu Ile Glu
```

-continued

```
               50                  55                  60
Asp Trp Ile Lys Arg Asn Pro Lys Gly Ser Ile Cys Ser Glu Gly Ile
 65                  70                  75                  80

Lys Ser Phe Lys Ala Ile Ala Asn Phe Gln Asp Tyr His Gly Leu Pro
                 85                  90                  95

Glu Phe Arg Lys Thr Ile Ala Lys Phe Met Glu Lys Thr Arg Gly Gly
                100                 105                 110

Arg Val Arg Phe Asp Pro Glu Arg Val Val Met Ala Gly Gly Ala Thr
                115                 120                 125

Gly Ala Asn Glu Thr Ile Ile Phe Cys Leu Ala Asp Pro Gly Asp Ala
            130                 135                 140

Phe Leu Val Pro Ser Pro Tyr Tyr Pro Ala Phe Asn Arg Asp Leu Arg
145                 150                 155                 160

Trp Arg Thr Gly Val Gln Leu Ile Pro Ile His Cys Glu Ser Ser Asn
                165                 170                 175

Asn Phe Lys Ile Thr Ser Lys Ala Val Lys Glu Ala Tyr Glu Asn Ala
                180                 185                 190

Gln Lys Ser Asn Ile Lys Val Lys Gly Leu Ile Leu Thr Asn Pro Ser
            195                 200                 205

Asn Pro Leu Gly Thr Thr Leu Asp Lys Asp Thr Leu Lys Ser Val Leu
210                 215                 220

Ser Phe Thr Asn Gln His Asn Ile His Leu Val Cys Asp Glu Ile Tyr
225                 230                 235                 240

Ala Ala Thr Val Phe Asp Thr Pro Gln Phe Val Ser Ile Ala Glu Ile
                245                 250                 255

Leu Asp Glu Gln Glu Met Thr Tyr Cys Asn Lys Asp Leu Val His Ile
                260                 265                 270

Val Tyr Ser Leu Ser Lys Asp Met Gly Leu Pro Gly Phe Arg Val Gly
            275                 280                 285

Ile Ile Tyr Ser Phe Asn Asp Asp Val Val Asn Cys Ala Arg Lys Met
            290                 295                 300

Ser Ser Phe Gly Leu Val Ser Thr Gln Thr Gln Tyr Phe Leu Ala Ala
305                 310                 315                 320

Met Leu Ser Asp Glu Lys Phe Val Asp Asn Phe Leu Arg Glu Ser Ala
                325                 330                 335

Met Arg Leu Gly Lys Arg His Lys His Phe Thr Asn Gly Leu Glu Val
            340                 345                 350

Val Gly Ile Lys Cys Leu Lys Asn Asn Ala Gly Leu Phe Cys Trp Met
            355                 360                 365

Asp Leu Arg Pro Leu Leu Arg Glu Ser Thr Phe Asp Ser Glu Met Ser
        370                 375                 380

Leu Trp Arg Val Ile Ile Asn Asp Val Lys Leu Asn Val Ser Pro Gly
385                 390                 395                 400

Ser Ser Phe Glu Cys Gln Glu Pro Gly Trp Phe Arg Val Cys Phe Ala
                405                 410                 415

Asn Met Asp Asp Gly Thr Val Asp Ile Ala Leu Ala Arg Ile Arg Arg
                420                 425                 430

Phe Val Gly Val Glu Lys Ser Gly Asp Lys Ser Ser Met Glu Gln
            435                 440                 445

Lys Gln Gln Trp Lys Lys Asn Asn Leu Arg Leu Ser Phe Ser Lys Arg
        450                 455                 460

Met Tyr Asp Glu Ser Val Leu Ser Pro Leu Ser Ser Pro Ile Pro Pro
465                 470                 475                 480
```

Ser Pro Leu Val Arg
            485

<210> SEQ ID NO 7
<211> LENGTH: 485
<212> TYPE: PRT
<213> ORGANISM: Lycopersicon esculentum

<400> SEQUENCE: 7

Met Gly Phe Glu Ile Ala Lys Thr Asn Ser Ile Leu Ser Lys Leu Ala
1               5                   10                  15

Thr Asn Glu Glu His Gly Glu Asn Ser Pro Tyr Phe Asp Gly Trp Lys
            20                  25                  30

Ala Tyr Asp Ser Asp Pro Phe His Pro Leu Lys Asn Pro Asn Gly Val
        35                  40                  45

Ile Gln Met Gly Leu Ala Glu Asn Gln Leu Cys Leu Asp Leu Ile Glu
    50                  55                  60

Asp Trp Ile Lys Arg Asn Pro Lys Gly Ser Ile Cys Ser Glu Gly Ile
65                  70                  75                  80

Lys Ser Phe Lys Ala Ile Ala Asn Phe Gln Asp Tyr His Gly Leu Pro
                85                  90                  95

Glu Phe Arg Lys Ala Ile Ala Lys Phe Met Glu Lys Thr Arg Gly Gly
            100                 105                 110

Arg Val Arg Phe Asp Pro Glu Arg Val Val Met Ala Gly Gly Ala Thr
        115                 120                 125

Gly Ala Asn Glu Thr Ile Ile Phe Cys Leu Ala Asp Pro Gly Asp Ala
    130                 135                 140

Phe Leu Val Pro Ser Pro Tyr Tyr Pro Ala Phe Asn Arg Asp Leu Arg
145                 150                 155                 160

Trp Arg Thr Gly Val Gln Leu Ile Pro Ile His Cys Glu Ser Ser Asn
                165                 170                 175

Asn Phe Lys Ile Thr Ser Lys Ala Val Lys Glu Ala Tyr Glu Asn Ala
            180                 185                 190

Gln Lys Ser Asn Ile Lys Val Lys Gly Leu Ile Leu Thr Asn Pro Ser
        195                 200                 205

Asn Pro Leu Gly Thr Thr Leu Asp Lys Asp Thr Leu Lys Ser Val Leu
    210                 215                 220

Ser Phe Thr Asn Gln His Asn Ile His Leu Val Cys Asp Glu Ile Tyr
225                 230                 235                 240

Ala Ala Thr Val Phe Asp Thr Pro Gln Phe Val Ser Ile Ala Glu Ile
                245                 250                 255

Leu Asp Glu Gln Glu Met Thr Tyr Tyr Asn Lys Asp Leu Val His Ile
            260                 265                 270

Val Tyr Ser Leu Ser Lys Asp Met Gly Leu Pro Gly Phe Arg Val Gly
        275                 280                 285

Ile Ile Tyr Ser Phe Asn Asp Asp Val Val Asn Cys Ala Arg Lys Met
    290                 295                 300

Ser Ser Phe Gly Leu Val Ser Thr Gln Thr Gln Tyr Phe Leu Ala Ala
305                 310                 315                 320

Met Leu Ser Asp Glu Lys Phe Val Asp Asn Phe Leu Arg Glu Ser Ala
                325                 330                 335

Met Arg Leu Gly Lys Arg His Lys His Phe Thr Asn Gly Leu Glu Val
            340                 345                 350

Val Gly Ile Lys Cys Leu Lys Asn Asn Ala Gly Leu Phe Cys Trp Met

```
                355                 360                 365
Asp Leu Arg Pro Leu Arg Glu Ser Thr Phe Asp Ser Glu Met Ser
            370                 375                 380

Leu Trp Arg Val Ile Ile Asn Asp Val Lys Leu Asn Val Ser Pro Gly
385                 390                 395                 400

Ser Ser Phe Glu Cys Gln Glu Pro Gly Trp Phe Arg Val Cys Phe Ala
                405                 410                 415

Asn Met Asp Asp Gly Thr Val Asp Ile Ala Leu Ala Arg Ile Arg Arg
            420                 425                 430

Phe Val Gly Val Glu Lys Ser Gly Asp Lys Ser Ser Ser Met Glu Gln
                435                 440                 445

Lys Gln Gln Trp Lys Lys Asn Asn Leu Arg Leu Ser Phe Ser Lys Arg
            450                 455                 460

Met Tyr Asp Glu Ser Val Leu Ser Pro Leu Ser Ser Pro Ile Pro Pro
465                 470                 475                 480

Ser Pro Leu Val Arg
                485

<210> SEQ ID NO 8
<211> LENGTH: 485
<212> TYPE: PRT
<213> ORGANISM: Lycopersicon esculentum

<400> SEQUENCE: 8

Met Gly Phe Glu Ile Ala Lys Thr Asn Ser Ile Leu Ser Lys Leu Ala
1               5                   10                  15

Thr Asn Glu Glu His Gly Glu Asn Ser Pro Tyr Phe Asp Gly Trp Lys
            20                  25                  30

Ala Tyr Asp Ser Asp Pro Phe His Pro Leu Lys Asn Pro Asn Gly Val
        35                  40                  45

Ile Gln Met Gly Leu Ala Glu Asn Gln Leu Cys Leu Asp Leu Ile Glu
    50                  55                  60

Asp Trp Ile Lys Arg Asn Pro Lys Gly Ser Ile Cys Ser Glu Gly Ile
65                  70                  75                  80

Lys Ser Phe Lys Ala Ile Ala Asn Phe Gln Asp Tyr His Gly Leu Pro
                85                  90                  95

Glu Phe Arg Lys Ala Ile Ala Lys Phe Met Glu Lys Thr Arg Gly Gly
            100                 105                 110

Arg Val Arg Phe Asp Pro Glu Arg Val Val Met Ala Gly Gly Ala Thr
        115                 120                 125

Gly Ala Asn Glu Thr Ile Ile Phe Cys Leu Ala Asp Pro Gly Asp Ala
    130                 135                 140

Phe Leu Glu Pro Ser Pro Tyr Tyr Pro Ala Phe Asn Arg Asp Leu Arg
145                 150                 155                 160

Trp Arg Thr Gly Val Gln Leu Ile Pro Ile His Cys Glu Ser Ser Asn
                165                 170                 175

Asn Phe Lys Ile Thr Ser Lys Ala Val Lys Glu Ala Tyr Glu Asn Ala
            180                 185                 190

Gln Lys Ser Asn Ile Lys Val Lys Gly Leu Ile Leu Thr Asn Pro Ser
        195                 200                 205

Asn Pro Leu Gly Thr Thr Leu Asp Lys Asp Thr Leu Lys Ser Val Leu
    210                 215                 220

Ser Phe Thr Asn Gln His Asn Ile His Leu Val Cys Asp Glu Ile Tyr
225                 230                 235                 240
```

Ala Ala Thr Val Phe Asp Thr Pro Gln Phe Val Ser Ile Ala Glu Ile
            245                 250                 255

Leu Asp Glu Gln Glu Met Thr Tyr Cys Asn Lys Asp Leu Val His Ile
        260                 265                 270

Val Tyr Ser Leu Ser Lys Asp Met Gly Leu Pro Gly Phe Arg Val Gly
    275                 280                 285

Ile Ile Tyr Ser Phe Asn Asp Val Val Asn Cys Ala Arg Lys Met
    290                 295                 300

Ser Ser Phe Gly Leu Val Ser Thr Gln Thr Gln Tyr Phe Leu Ala Ala
305                 310                 315                 320

Met Leu Ser Asp Glu Lys Phe Val Asp Asn Phe Leu Arg Glu Ser Ala
                325                 330                 335

Met Arg Leu Gly Lys Arg His Lys His Phe Thr Asn Gly Leu Glu Val
                340                 345                 350

Val Gly Ile Lys Cys Leu Lys Asn Asn Ala Gly Leu Phe Cys Trp Met
            355                 360                 365

Asp Leu Arg Pro Leu Leu Arg Glu Ser Thr Phe Asp Ser Glu Met Ser
    370                 375                 380

Leu Trp Arg Val Ile Ile Asn Asp Val Lys Leu Asn Val Ser Pro Gly
385                 390                 395                 400

Ser Ser Phe Glu Cys Gln Glu Pro Gly Trp Phe Arg Val Cys Phe Ala
                405                 410                 415

Asn Met Asp Asp Gly Thr Val Asp Ile Ala Leu Ala Arg Ile Arg Arg
                420                 425                 430

Phe Val Gly Val Glu Lys Ser Gly Asp Lys Ser Ser Met Glu Gln
            435                 440                 445

Lys Gln Gln Trp Lys Lys Asn Asn Leu Arg Leu Ser Phe Ser Lys Arg
    450                 455                 460

Met Tyr Asp Glu Ser Val Leu Ser Pro Leu Ser Ser Pro Ile Pro Pro
465                 470                 475                 480

Ser Pro Leu Val Arg
            485

<210> SEQ ID NO 9
<211> LENGTH: 1459
<212> TYPE: DNA
<213> ORGANISM: Lycopersicon esculentum

<400> SEQUENCE: 9
atgggatttg agattgcaaa gaccaactca atcttatcaa aattggctac taatgaagag      60
catggcgaaa actcgccata ttttgatggg tggaaagcat acgatagtga tcctttccac     120
cctctaaaaa accccaacgg agttatccaa atgggtcttg ctgaaaatca gctttgttta     180
gacttgatag aagattggat taagagaaac ccaaaaggtt caatttgttc tgaaggaatc     240
aaatcattca aggccattgc caactttcaa gattatcatg gcttgcctga attcagaaaa     300
gcgattgcga aatttatgga gaaacaaga ggaggaagag ttagatttga tccagaaaga     360
gttgttatgg ctggtggtgc cactggggct aatgagacaa ttatattttg tttggctgat     420
cctggcgatg catttttagt accttccacca tactacccag catttaacag agatttaaga     480
tggagaactg gagtacaact tattccaatt cactgtgaga gctccaataa tttcaaaatt     540
acttcaaaag cagtaaaaga agcatatgaa aatgcacaaa aatcaaacat caaagtaaaa     600
ggtttgattt tgaccaatcc atcaaatcca ttgggcacca ctttggacaa agacacactg     660
aaaagtgtct tgagtttcac caaccaacac aacatccacc ttgtttgtga cgaaatctac     720

```
gcagccactg tctttgacac gcctcaattc gtcagtatag ctgaaatcct cgatgaacag      780
gaaatgactt actgcaacaa agatttagtt cacatcgtct acagtctttc aaaagacatg      840
gggttaccag gatttagagt cggaatcata tattctttta acgacgatgt cgttaattgt      900
gctagaaaaa tgtcgagttt cggtttagta tctacacaaa cgcaatattt tttagcggca      960
atgctatcgg acgaaaaatt cgtcgataat tttctaagag aaagcgcgat gaggttaggt     1020
aaaaggcaca acattttac taatggactt gaagtagtgg gaattaaatg cttgaaaaat      1080 aatgcgggc ttttttgttg gatggatttg cgtccacttt taagggaatc gactttcgat     1140
agcgaaatgt cgttatggag agttattata aacgatgtta agcttaacgt ctcgcctgga     1200
tcttcgtttg aatgtcaaga gccagggtgg ttccgagttt gttttgcaaa tatggatgat     1260
ggaacggttg atattgcgct cgcgaggatt cggaggttcg taggtgttga gaaaagtgga     1320
gataaatcga gttcgatgga acagaagcaa caatggaaga agaataattt gagacttagt     1380
ttttcgaaaa gaatgtatga tgaaagtgtt ttgtcaccac tttcgtcacc tattcctccc     1440
tcaccattag ttcgttaag                                                   1459

<210> SEQ ID NO 10
<211> LENGTH: 1459
<212> TYPE: DNA
<213> ORGANISM: Lycopersicon esculentum

<400> SEQUENCE: 10
atgggatttg agattgcaaa gaccaactca atcttatcaa aattggctac taatgaagag       60
catggcgaaa actcgccata ttttgatggg tggaaagcat acgatagtga tccttttccac     120 cctctaaaaa accccaacgg agttatccaa atgggtcttg ctgaaaatca gctttgtttta     180 gacttgatag aagattggat taagagaaac ccaaaaggtt caatttgttc tgaaggaatc      240
aaatcattca aggccattgc caactttcaa gattatcatg gcttgcctga attcagaaaa      300
gcgattacga aatttatgga gaaaacaaga ggaggaagag ttagatttga tccagaaaga      360
gttgttatgg ctggtggtgc cactgggggct aatgagacaa ttatattttg tttggctgat     420
cctggcgatg cattttttagt accttcacca tactacccag catttaacag agatttaaga     480
tggagaactg gagtacaact tattccaatt cactgtgaga gctccaataa tttcaaaatt      540
acttcaaaag cagtaaaaga agcatatgaa aatgcacaaa atcaaacat caaagtaaaa       600 ggtttgattt tgaccaatcc atcaaatcca ttgggcacca ctttggacaa agacacactg      660
aaaagtgtct tgagtttcac caaccaacac aacatccacc ttgttgtga cgaaatctac       720 gcagccactg tctttgacac gcctcaattc gtcagtatag ctgaaatcct cgatgaacag      780
gaaatgactt actgcaacaa agatttagtt cacatcgtct acagtctttc aaaagacatg      840
gggttaccag gatttagagt cggaatcata tattctttta acgacgatgt cgttaattgt      900
gctagaaaaa tgtcgagttt cggtttagta tctacacaaa cgcaatattt tttagcggca      960
atgctatcgg acgaaaaatt cgtcgataat tttctaagag aaagcgcgat gaggttaggt     1020
aaaaggcaca acattttac taatggactt gaagtagtgg gaattaaatg cttgaaaaat      1080 aatgcgggc ttttttgttg gatggatttg cgtccacttt taagggaatc gactttcgat     1140
agcgaaatgt cgttatggag agttattata aacgatgtta agcttaacgt ctcgcctgga     1200
tcttcgtttg aatgtcaaga gccagggtgg ttccgagttt gttttgcaaa tatggatgat     1260
ggaacggttg atattgcgct cgcgaggatt cggaggttcg taggtgttga gaaaagtgga     1320
```

| | |
|---|---|
| gataaatcga gttcgatgga acagaagcaa caatggaaga agaataattt gagacttagt | 1380 |
| ttttcgaaaa gaatgtatga tgaaagtgtt ttgtcaccac tttcgtcacc tattcctccc | 1440 |
| tcaccattag ttcgttaag | 1459 |

<210> SEQ ID NO 11
<211> LENGTH: 1459
<212> TYPE: DNA
<213> ORGANISM: Lycopersicon esculentum

<400> SEQUENCE: 11

| | |
|---|---|
| atgggatttg agattgcaaa gaccaactca atcttatcaa aattggctac taatgaagag | 60 |
| catggcgaaa actcgccata ttttgatggg tggaaagcat acgatagtga tcctttccac | 120 |
| cctctaaaaa accccaacgg agttatccaa atgggtcttg ctgaaaatca gctttgttta | 180 |
| gacttgatag aagattggat taagagaaac ccaaaaggtt caatttgttc tgaaggaatc | 240 |
| aaatcattca aggccattgc caactttcaa gattatcatg gcttgcctga attcagaaaa | 300 |
| gcgattgcga aatttatgga gaaaacaaga ggaagaagag ttagatttga tccagaaaga | 360 |
| gttgttatgg ctggtggtgc cactgggggct aatgagacaa ttatattttg tttggctgat | 420 |
| cctggcgatg catttttagt accttcacca tactacccag catttaacag agatttaaga | 480 |
| tggagaactg gagtacaact tattccaatt cactgtgaga gctccaataa tttcaaaatt | 540 |
| acttcaaaag cagtaaaaga agcatatgaa aatgcacaaa atcaaacat caaagtaaaa | 600 |
| ggtttgattt tgaccaatcc atcaaatcca ttgggcacca ctttggacaa agacacactg | 660 |
| aaaagtgtct tgagtttcac caaccaacac aacatccacc ttgttgtga cgaaatctac | 720 |
| gcagccactg tctttgacac gcctcaattc gtcagtatag ctgaaatcct cgatgaacag | 780 |
| gaaatgactt actgcaacaa agatttagtt cacatcgtct acagtctttc aaaagacatg | 840 |
| gggttaccag gatttagagt cggaatcata tattctttta acgacgatgt cgttaattgt | 900 |
| gctagaaaaa tgtcgagttt cggtttagta tctacacaaa cgcaatattt tttagcggca | 960 |
| atgctatcgg acgaaaaatt cgtcgataat tttctaagag aaagcgcgat gaggttaggt | 1020 |
| aaaaggcaca acattttac taatggactt gaagtagtgg gaattaaatg cttgaaaaat | 1080 |
| aatgcgggc ttttttgttg gatggatttg cgtccacttt taagggaatc gactttcgat | 1140 |
| agcgaaatgt cgttatggag agttattata aacgatgtta agcttaacgt ctcgcctgga | 1200 |
| tcttcgtttg aatgtcaaga gccagggtgg ttccgagttt gttttgcaaa tatggatgat | 1260 |
| ggaacggttg atattgcgct cgcgaggatt cggaggttcg taggtgttga gaaaagtgga | 1320 |
| gataaatcga gttcgatgga acagaagcaa caatggaaga agaataattt gagacttagt | 1380 |
| ttttcgaaaa gaatgtatga tgaaagtgtt ttgtcaccac tttcgtcacc tattcctccc | 1440 |
| tcaccattag ttcgttaag | 1459 |

<210> SEQ ID NO 12
<211> LENGTH: 1459
<212> TYPE: DNA
<213> ORGANISM: Lycopersicon esculentum

<400> SEQUENCE: 12

| | |
|---|---|
| atgggatttg agattgcaaa gaccaactca atcttatcaa aattggctac taatgaagag | 60 |
| catggcgaaa actcgccata ttttgatggg tggaaagcat acgatagtga tcctttccac | 120 |
| cctctaaaaa accccaacgg agttatccaa atgggtcttg ctgaaaatca gctttgttta | 180 |
| gacttgatag aagattggat taagagaaac ccaaaaggtt caatttgttc tgaaggaatc | 240 |

```
aaatcattca aggccattgc caactttcaa gattatcatg cttgcctga attcagaaaa      300 gcgattgcga aatttatgga gaaaacaaga ggaggaagag ttagatttga tctagaaaga      360
gttgttatgg ctggtggtgc cactggggct aatgagacaa ttatattttg tttggctgat      420
cctggcgatg catttttagt accttcacca tactacccag catttaacag agatttaaga      480
tggagaactg gagtacaact tattccaatt cactgtgaga gctccaataa tttcaaaatt      540
acttcaaaag cagtaaaaga agcatatgaa aatgcacaaa aatcaaacat caaagtaaaa      600
ggtttgattt tgaccaatcc atcaaatcca ttgggcacca ctttggacaa agacacactg      660
aaaagtgtct tgagtttcac caaccaacac aacatccacc ttgtttgtga cgaaatctac      720
gcagccactg tctttgacac gcctcaattc gtcagtatag ctgaaatcct cgatgaacag      780
gaaatgactt actgcaacaa agatttagtt cacatcgtct acagtctttc aaaagacatg      840
gggttaccag gatttagagt cggaatcata tattctttta cgacgatgt cgttaattgt      900 gctagaaaaa tgtcgagttt cggtttagta tctacacaaa cgcaatattt tttagcggca      960
atgctatcgg acgaaaaatt cgtcgataat tttctaagag aaagcgcgat gaggttaggt     1020
aaaaggcaca acatttttac taatggactt gaagtagtgg gaattaaatg cttgaaaaat     1080 aatgcgggc tttttttgttg gatggatttg cgtccacttt taagggaatc gactttcgat     1140
agcgaaatgt cgttatggag agttattata acgatgtta agcttaacgt ctcgcctgga     1200
tcttcgtttg aatgtcaaga gccagggtgg ttccgagttt gttttgcaaa tatggatgat     1260
ggaacggttg atattgcgct cgcgaggatt cggaggttcg taggtgttga aaaagtggaa     1320
gataaatcga gttcgatgga acagaagcaa caatggaaga agaataattt gagacttagt     1380 tttttcgaaaa gaatgtatga tgaaagtgtt ttgtcaccac tttcgtcacc tattcctccc     1440
tcaccattag ttcgttaag                                                 1459

<210> SEQ ID NO 13
<211> LENGTH: 1459
<212> TYPE: DNA
<213> ORGANISM: Lycopersicon esculentum

<400> SEQUENCE: 13
atgggatttg agattgcaaa gaccaactca atcttatcaa aattggctac taatgaagag       60
catggcgaaa actcgccata ttttgatggg tggaaagcat acgatagtga tccttttccac      120 cctctaaaaa accccaacgg agttatccaa atgggtcttg ctgaaaatca gctttgttta      180
gacttgatag aagattggat taagagaaac ccaaaaggtt caatttgttc tgaaggaatc      240
aaatcattca aggccattgc caactttcaa gattatcatg cttgcctga attcagaaaa      300 gtgattgcga aatttatgga gaaaacaaga ggaggaagag ttagatttga tccagaaaga      360
gttgttatgg ctggtggtgc cactggggct aatgagacaa ttatattttg tttggctgat      420
cctggcgatg catttttagt accttcacca tactacccag catttaacag agatttaaga      480
tggagaactg gagtacaact tattccaatt cactgtgaga gctccaataa tttcaaaatt      540
acttcaaaag cagtaaaaga agcatatgaa aatgcacaaa aatcaaacat caaagtaaaa      600
ggtttgattt tgaccaatcc atcaaatcca ttgggcacca ctttggacaa agacacactg      660
aaaagtgtct tgagtttcac caaccaacac aacatccacc ttgtttgtga cgaaatctac      720
gcagccactg tctttgacac gcctcaattc gtcagtatag ctgaaatcct cgatgaacag      780
gaaatgactt actgcaacaa agatttagtt cacatcgtct acagtctttc aaaagacatg      840
```

```
gggttaccag gatttagagt cggaatcata tattcttta acgacgatgt cgttaattgt      900
gctagaaaaa tgtcgagttt cggtttagta tctacacaaa cgcaatattt tttagcggca      960
atgctatcgg acgaaaaatt cgtcgataat tttctaagag aaagcgcgat gaggttaggt     1020
aaaaggcaca acattttac taatggactt gaagtagtgg gaattaaatg cttgaaaaat      1080
aatgcgggc ttttttgttg gatggatttg cgtccacttt taagggaatc gactttcgat      1140
agcgaaatgt cgttatggag agttattata acgatgtta agcttaacgt ctcgcctgga      1200
tcttcgtttg aatgtcaaga gccagggtgg ttccgagttt gttttgcaaa tatggatgat     1260
ggaacggttg atattgcgct cgcgaggatt cggaggttcg taggtgttga gaaaagtgga     1320
gataaatcga gttcgatgga acagaagcaa caatggaaga agaataattt gagacttagt     1380
ttttcgaaaa gaatgtatga tgaaagtgtt ttgtcaccac tttcgtcacc tattcctccc     1440
tcaccattag ttcgttaag                                                  1459

<210> SEQ ID NO 14
<211> LENGTH: 1459
<212> TYPE: DNA
<213> ORGANISM: Lycopersicon esculentum

<400> SEQUENCE: 14
atgggatttg agattgcaaa gaccaactca atcttatcaa aattggctac taatgaagag       60
catggcgaaa actcgccata ttttgatggg tggaaagcat acgatagtga tccttccac       120
cctctaaaaa accccaacgg agttatccaa atgggtcttg ctgaaaatca gctttgttta      180
gacttgatag aagattggat taagagaaac ccaaaaggtt caatttgttc tgaaggaatc      240
aaatcattca aggccattgc caactttcaa gattatcatg gcttgcctga attcagaaaa      300
acgattgcga aatttatgga gaaaacaaga ggaggaagag ttagatttga tccgaaagga      360
gttgttatgg ctggtggtgc cactggggct aatgagacaa ttatattttg tttggctgat      420
cctggcgatg catttttagt accttcacca tactacccag catttaacag agatttaaga      480
tggagaactg gagtacaact tattccaatt cactgtgaga gctccaataa tttcaaaatt      540
acttcaaaag cagtaaaaga agcatatgaa atgcacaaa atcaaacat caaagtaaaa      600
ggtttgattt tgaccaatcc atcaaatcca ttgggcacca ctttggacaa agacacactg      660
aaaagtgtct tgagtttcac caaccaacac aacatccacc ttgtttgtga cgaaatctac      720
gcagccactg tctttgacac gcctcaattc gtcagtatag ctgaaatcct cgatgaacag      780
gaaatgactt actgcaacaa agatttagtt cacatcgtct acagtctttc aaaagacatg      840
gggttaccag gatttagagt cggaatcata tattctttta acgacgatgt cgttaattgt      900
gctagaaaaa tgtcgagttt cggtttagta tctacacaaa cgcaatattt tttagcggca      960
atgctatcgg acgaaaaatt cgtcgataat tttctaagag aaagcgcgat gaggttaggt     1020
aaaaggcaca acattttac taatggactt gaagtagtgg gaattaaatg cttgaaaaat      1080
aatgcgggc ttttttgttg gatggatttg cgtccacttt taagggaatc gactttcgat      1140
agcgaaatgt cgttatggag agttattata acgatgtta agcttaacgt ctcgcctgga      1200
tcttcgtttg aatgtcaaga gccagggtgg ttccgagttt gttttgcaaa tatggatgat     1260
ggaacggttg atattgcgct cgcgaggatt cggaggttcg taggtgttga gaaaagtgga     1320
gataaatcga gttcgatgga acagaagcaa caatggaaga agaataattt gagacttagt     1380
ttttcgaaaa gaatgtatga tgaaagtgtt ttgtcaccac tttcgtcacc tattcctccc     1440
tcaccattag ttcgttaag                                                  1459
```

<210> SEQ ID NO 15
<211> LENGTH: 1459
<212> TYPE: DNA
<213> ORGANISM: Lycopersicon esculentum

<400> SEQUENCE: 15

```
atgggatttg agattgcaaa gaccaactca atcttatcaa aattggctac taatgaagag      60
catggcgaaa actcgccata ttttgatggg tggaaagcat acgatagtga tcctttccac     120
cctctaaaaa accccaacgg agttatccaa atgggtcttg ctgaaaatca gctttgttta     180
gacttgatag aagattggat taagagaaac ccaaaaggtt caatttgttc tgaaggaatc     240
aaatcattca aggccattgc caactttcaa gattatcatg gcttgcctga attcagaaaa     300
gcgattgcga aatttatgga gaaaacaaga ggaggaagag ttagatttga tccagaaaga     360
gttgttatgg ctggtggtgc cactggggct aatgagacaa ttatattttg tttggctgat     420
cctggcgatg catttttagt accttcacca tactacccag catttaacag agatttaaga     480
tggagaactg gagtacaact tattccaatt cactgtgaga gctccaataa tttcaaaatt     540
acttcaaaag cagtaaaaga agcatatgaa atgcacaaa atcaaacat caaagtaaaa      600
ggtttgattt tgaccaatcc atcaaatcca ttgggcacca ctttggacaa agacacactg     660
aaaagtgtct tgagtttcac caaccaacac aacatccacc ttgttgtga cgaaatctac      720
gcagccactg tctttgacac gcctcaattc gtcagtatag ctgaaatcct cgatgaacag     780
gaaatgactt actacaacaa agatttagtt cacatcgtct acagtctttc aaaagacatg     840
gggttaccag gatttagagt cggaatcata tattctttta cgacgatgt cgttaattgt      900
gctagaaaaa tgtcgagttt cggtttagta tctacacaaa cgcaatattt tttagcggca     960
atgctatcgg acgaaaaatt cgtcgataat tttctaagag aaagcgcgat gaggttaggt    1020
aaaaggcaca acattttac taatggactt gaagtagtgg gaattaaatg cttgaaaaat     1080
aatgcggggc ttttttgttg gatggatttg cgtccacttt aagggaatc gactttcgat     1140
agcgaaatgt cgttatggag agttattata acgatgtta agcttaacgt ctcgcctgga    1200
tcttcgtttg aatgtcaaga gccagggtgg ttccgagttt gttttgcaaa tatggatgat    1260
ggaacggttg atattgcgct cgcgaggatt cggaggttcg taggtgttga gaaaagtgga    1320
gataaatcga gttcgatgga acagaagcaa caatggaaga agaataattt gagacttagt    1380
ttttcgaaaa gaatgtatga tgaaagtgtt ttgtcaccac tttcgtcacc tattcctccc    1440
tcaccattag ttcgttaag                                                1459
```

<210> SEQ ID NO 16
<211> LENGTH: 1459
<212> TYPE: DNA
<213> ORGANISM: Lycopersicon esculentum

<400> SEQUENCE: 16

```
atgggatttg agattgcaaa gaccaactca atcttatcaa aattggctac taatgaagag      60
catggcgaaa actcgccata ttttgatggg tggaaagcat acgatagtga tcctttccac     120
cctctaaaaa accccaacgg agttatccaa atgggtcttg ctgaaaatca gctttgttta     180
gacttgatag aagattggat taagagaaac ccaaaaggtt caatttgttc tgaaggaatc     240
aaatcattca aggccattgc caactttcaa gattatcatg gcttgcctga attcagaaaa     300
gcgattgcga aatttatgga gaaaacaaga ggaggaagag ttagatttga tccagaaaga     360
```

```
gttgttatgg ctggtggtgc cactggggct aatgagacaa ttatattttg tttggctgat      420
cctggcgatg catttttaga accttcacca tactacccag catttaacag agatttaaga      480
tggagaactg gagtacaact tattccaatt cactgtgaga gctccaataa tttcaaaatt      540
acttcaaaag cagtaaaaga agcatatgaa aatgcacaaa aatcaaacat caaagtaaaa      600
ggtttgattt tgaccaatcc atcaaatcca ttgggcacca ctttggacaa agacacactg      660
aaaagtgtct tgagtttcac caaccaacac aacatccacc ttgtttgtga cgaaatctac      720
gcagccactg tctttgacac gcctcaattc gtcagtatag ctgaaatcct cgatgaacag      780
gaaatgactt actgcaacaa agatttagtt cacatcgtct acagtctttc aaaagacatg      840
gggttaccag gatttagagt cggaatcata tattctttta acgacgatgt cgttaattgt      900
gctagaaaaa tgtcgagttt cggtttagta tctacacaaa cgcaatattt tttagcggca      960
atgctatcgg acgaaaaatt cgtcgataat tttctaagag aaagcgcgat gaggttaggt     1020
aaaaggcaca acatttttac taatggactt gaagtagtgg gaattaaatg cttgaaaaat     1080
aatgcggggc ttttttgttg gatggatttg cgtccacttt taagggaatc gactttcgat     1140
agcgaaatgt cgttatggag agttattata acgatgttaa agcttaacgt ctcgcctgga     1200
tcttcgtttg aatgtcaaga gccagggtgg ttccgagttt gttttgcaaa tatggatgat     1260
ggaacggttg atattgcgct cgcgaggatt cggaggttcg taggtgttga aaaagtgga      1320 gataaatcga gttcgatgga acagaagcaa caatggaaga agaataattt gagacttagt     1380
ttttcgaaaa gaatgtatga tgaaagtgtt ttgtcaccac tttcgtcacc tattcctccc     1440
tcaccattag ttcgttaag                                                  1459
```

<210> SEQ ID NO 17
<211> LENGTH: 2523
<212> TYPE: DNA
<213> ORGANISM: Lycopersicon esculentum
<220> FEATURE:
<221> NAME/KEY: exon
<222> LOCATION: (1)..(171)
<223> OTHER INFORMATION: Exon 1
<220> FEATURE:
<221> NAME/KEY: exon
<222> LOCATION: (270)..(399)
<223> OTHER INFORMATION: Exon 2
<220> FEATURE:
<221> NAME/KEY: exon
<222> LOCATION: (485)..(644)
<223> OTHER INFORMATION: Exon 3
<220> FEATURE:
<221> NAME/KEY: exon
<222> LOCATION: (1526)..(2523)
<223> OTHER INFORMATION: Exon 4

<400> SEQUENCE: 17

```
atg gga ttt gag att gca aag acc aac tca atc tta tca aaa ttg gct        48
Met Gly Phe Glu Ile Ala Lys Thr Asn Ser Ile Leu Ser Lys Leu Ala
1               5                   10                  15 act aat gaa gag cat ggc gaa aac tcg cca tat ttt gat ggg tgg aaa        96
Thr Asn Glu Glu His Gly Glu Asn Ser Pro Tyr Phe Asp Gly Trp Lys
            20                  25                  30 gca tac gat agt gat cct ttc cac cct cta aaa aac ccc aac gga gtt       144
Ala Tyr Asp Ser Asp Pro Phe His Pro Leu Lys Asn Pro Asn Gly Val
        35                  40                  45 atc caa atg ggt ctt gct gaa aat cag gtaattaatt atcctttatt             191
Ile Gln Met Gly Leu Ala Glu Asn Gln
    50                  55 tatatatttt gcagtttgac caaacagact attataattt ttttctgaaa cctcgatggt     251
```

```
gttaaatttc ttttgtag ctt tgt tta gac ttg ata gaa gat tgg att aag       302
              Leu Cys Leu Asp Leu Ile Glu Asp Trp Ile Lys
                      60                  65 aga aac cca aaa ggt tca att tgt tct gaa gga atc aaa tca ttc aag       350
Arg Asn Pro Lys Gly Ser Ile Cys Ser Glu Gly Ile Lys Ser Phe Lys
 70              75                  80 gcc att gcc aac ttt caa gat tat cat ggc ttg cct gaa ttc aga aaa g     399
Ala Ile Ala Asn Phe Gln Asp Tyr His Gly Leu Pro Glu Phe Arg Lys
 85              90                  95                 100 tacatatcgt actatagtca gttaaattat attgatagta taaaaattcg ttaatatatt     459
taactaacga gtttatttaa tcagg cg  att gcg aaa ttt atg gag aaa aca       510
                               Ala Ile Ala Lys Phe Met Glu Lys Thr
                                                    105 aga gga gga aga gtt aga ttt gat cca gaa aga gtt gtt atg gct ggt       558
Arg Gly Gly Arg Val Arg Phe Asp Pro Glu Arg Val Val Met Ala Gly
110             115                 120                 125 ggt gcc act gga gct aat gag aca att ata ttt tgt ttg gct gat cct       606
Gly Ala Thr Gly Ala Asn Glu Thr Ile Ile Phe Cys Leu Ala Asp Pro
            130                 135                 140 ggc gat gca ttt tta gta cct tca cca tac tac cca gc  gtaagtatat       654
Gly Asp Ala Phe Leu Val Pro Ser Pro Tyr Tyr Pro Ala
        145                 150 ttaattatat atgtgtaaaa aaaattaaaa tcatcaaatc atttttttta tttgtattac     714
caaataaatt gtctaatttt caagattgta acacattcat caaagtacct aataatataa    774
acgattcagt atattaacga tgtatataat ttaattcctt tggcggattt gtcttttat     834 gttgggccat cagaagaaca ttctggtgta ttaattaatt aattaattaa taatagatgt    894
gttgtcattc ttttttaaga cagcgagagt ttaattagtc ttaattactg gattatcacg    954
caagctcttt cttgaatttt attattctta tattaaacac atgatagcat aatatctttc   1014
ttttgtggaa tccagcttgt tcgtgaagct ttgtattcac acttataaaa caacaaaaaa   1074
taaaatctgg tggtaattga ttaaagagag aaatataaaa aataatagt caaatagact    1134 aataaggaaa gaaataaaaa atacacaaaa tactaaaaaa aaagaattaa ggtatagtgg   1194
tctattattg agaacttttt tgaagaattg aaccccactt taatttcttg cttgacccgt   1254
gaccattgct tatcgaggta aaataaaatt tcaaacattg actatgactt gttagagagt   1314
aattaccaca agtcaaaatt ttgttactct gtctcgttat ttcattagga tcgataagat   1374
aacatctaac atatatatct ttttttattag tacttgttta tttttagtaa aagcacgtta   1434
tacattttac aatagtcaat tgttgcatat attagtatat atattttgct aagtcctaac   1494
taacaatatt tttggcaatt gactaatgca g a ttt aac aga gat tta aga tgg    1547
                                    Phe Asn Arg Asp Leu Arg Trp
                                            155                 160 aga act gga gta caa ctt att cca att cac tgt gag agc tcc aat aat      1595
Arg Thr Gly Val Gln Leu Ile Pro Ile His Cys Glu Ser Ser Asn Asn
            165                 170                 175 ttc aaa att act tca aaa gca gta aaa gaa gca tat gaa aat gca caa      1643
Phe Lys Ile Thr Ser Lys Ala Val Lys Glu Ala Tyr Glu Asn Ala Gln
        180                 185                 190 aaa tca aac atc aaa gta aaa ggt ttg att ttg acc aat cca tca aat      1691
Lys Ser Asn Ile Lys Val Lys Gly Leu Ile Leu Thr Asn Pro Ser Asn
    195                 200                 205 cca ttg ggc acc act ttg gac aaa gac aca ctg aaa agt gtc ttg agt      1739
Pro Leu Gly Thr Thr Leu Asp Lys Asp Thr Leu Lys Ser Val Leu Ser
210                 215                 220                 225
```

| | | | | | | | | | | | | | | | | |
|---|---|---|---|---|---|---|---|---|---|---|---|---|---|---|---|---|
| ttc | acc | aac | caa | cac | aac | atc | cac | ctt | gtt | tgt | gac | gaa | atc | tac | gca | 1787 |
| Phe | Thr | Asn | Gln | His | Asn | Ile | His | Leu | Val | Cys | Asp | Glu | Ile | Tyr | Ala | |
| | | | 230 | | | | 235 | | | | | 240 | | | | |
| gcc | act | gtc | ttt | gac | acg | cct | caa | ttc | gtc | agt | ata | gct | gaa | atc | ctc | 1835 |
| Ala | Thr | Val | Phe | Asp | Thr | Pro | Gln | Phe | Val | Ser | Ile | Ala | Glu | Ile | Leu | |
| | | 245 | | | | | 250 | | | | | 255 | | | | |
| gat | gaa | cag | gaa | atg | act | tac | tgc | aac | aaa | gat | tta | gtt | cac | atc | gtc | 1883 |
| Asp | Glu | Gln | Glu | Met | Thr | Tyr | Cys | Asn | Lys | Asp | Leu | Val | His | Ile | Val | |
| | | | 260 | | | | 265 | | | | | 270 | | | | |
| tac | agt | ctt | tca | aaa | gac | atg | ggg | tta | cca | gga | ttt | aga | gtc | gga | atc | 1931 |
| Tyr | Ser | Leu | Ser | Lys | Asp | Met | Gly | Leu | Pro | Gly | Phe | Arg | Val | Gly | Ile | |
| | | 275 | | | | | 280 | | | | | 285 | | | | |
| ata | tat | tct | ttt | aac | gac | gat | gtc | gtt | aat | tgt | gct | aga | aaa | atg | tcg | 1979 |
| Ile | Tyr | Ser | Phe | Asn | Asp | Asp | Val | Val | Asn | Cys | Ala | Arg | Lys | Met | Ser | |
| 290 | | | | | 295 | | | | | 300 | | | | | 305 | |
| agt | ttc | ggt | tta | gta | tct | aca | caa | acg | caa | tat | ttt | tta | gcg | gca | atg | 2027 |
| Ser | Phe | Gly | Leu | Val | Ser | Thr | Gln | Thr | Gln | Tyr | Phe | Leu | Ala | Ala | Met | |
| | | | | 310 | | | | | 315 | | | | | 320 | | |
| cta | tcg | gac | gaa | aaa | ttc | gtc | gat | aat | ttt | cta | aga | gaa | agc | gcg | atg | 2075 |
| Leu | Ser | Asp | Glu | Lys | Phe | Val | Asp | Asn | Phe | Leu | Arg | Glu | Ser | Ala | Met | |
| | | | 325 | | | | | 330 | | | | | 335 | | | |
| agg | tta | ggt | aaa | agg | cac | aaa | cat | ttt | act | aat | gga | ctt | gaa | gta | gtg | 2123 |
| Arg | Leu | Gly | Lys | Arg | His | Lys | His | Phe | Thr | Asn | Gly | Leu | Glu | Val | Val | |
| | | 340 | | | | | 345 | | | | | 350 | | | | |
| gga | att | aaa | tgc | ttg | aaa | aat | aat | gcg | ggg | ctt | ttt | tgt | tgg | atg | gat | 2171 |
| Gly | Ile | Lys | Cys | Leu | Lys | Asn | Asn | Ala | Gly | Leu | Phe | Cys | Trp | Met | Asp | |
| 355 | | | | | 360 | | | | | 365 | | | | | | |
| ttg | cgt | cca | ctt | tta | agg | gaa | tcg | act | ttc | gat | agc | gaa | atg | tcg | tta | 2219 |
| Leu | Arg | Pro | Leu | Leu | Arg | Glu | Ser | Thr | Phe | Asp | Ser | Glu | Met | Ser | Leu | |
| 370 | | | | | 375 | | | | | 380 | | | | | 385 | |
| tgg | aga | gtt | att | ata | aac | gat | gtt | aag | ctt | aac | gtc | tcg | cct | gga | tct | 2267 |
| Trp | Arg | Val | Ile | Ile | Asn | Asp | Val | Lys | Leu | Asn | Val | Ser | Pro | Gly | Ser | |
| | | | | 390 | | | | | 395 | | | | | 400 | | |
| tcg | ttt | gaa | tgt | caa | gag | cca | ggg | tgg | ttc | cga | gtt | tgt | ttt | gca | aat | 2315 |
| Ser | Phe | Glu | Cys | Gln | Glu | Pro | Gly | Trp | Phe | Arg | Val | Cys | Phe | Ala | Asn | |
| | | | 405 | | | | | 410 | | | | | 415 | | | |
| atg | gat | gat | gga | acg | gtt | gat | att | gcg | ctc | gcg | agg | att | cgg | agg | ttc | 2363 |
| Met | Asp | Asp | Gly | Thr | Val | Asp | Ile | Ala | Leu | Ala | Arg | Ile | Arg | Arg | Phe | |
| | | | 420 | | | | | 425 | | | | | 430 | | | |
| gta | ggt | gtt | gag | aaa | agt | gga | gat | aaa | tcg | agt | tcg | atg | gaa | aag | aag | 2411 |
| Val | Gly | Val | Glu | Lys | Ser | Gly | Asp | Lys | Ser | Ser | Ser | Met | Glu | Lys | Lys | |
| | | 435 | | | | | 440 | | | | | 445 | | | | |
| caa | caa | tgg | aag | aag | aat | aat | ttg | aga | ctt | agt | ttt | tcg | aaa | aga | atg | 2459 |
| Gln | Gln | Trp | Lys | Lys | Asn | Asn | Leu | Arg | Leu | Ser | Phe | Ser | Lys | Arg | Met | |
| 450 | | | | | 455 | | | | | 460 | | | | | 465 | |
| tat | gat | gaa | agt | gtt | ttg | tca | cca | ctt | tcg | tca | cct | att | cct | ccc | tca | 2507 |
| Tyr | Asp | Glu | Ser | Val | Leu | Ser | Pro | Leu | Ser | Ser | Pro | Ile | Pro | Pro | Ser | |
| | | | | 470 | | | | | 475 | | | | | 480 | | |
| cca | tta | gtt | cgt | taa | g | | | | | | | | | | | 2523 |
| Pro | Leu | Val | Arg | | | | | | | | | | | | | |
| | | | 485 | | | | | | | | | | | | | |

<210> SEQ ID NO 18
<211> LENGTH: 97
<212> TYPE: PRT
<213> ORGANISM: Lycopersicon esculentum

<400> SEQUENCE: 18

Leu Cys Leu Asp Leu Ile Glu Asp Trp Ile Lys Arg Asn Pro Lys Gly
1               5                   10                  15

Ser Ile Cys Ser Glu Gly Ile Lys Ser Phe Lys Ala Ile Ala Asn Phe
            20                  25                  30

Gln Asp Tyr His Gly Leu Pro Glu Phe Arg Lys Ala Ile Thr Lys Phe
        35                  40                  45

Met Glu Lys Thr Arg Gly Gly Arg Val Arg Phe Asp Pro Glu Arg Val
    50                  55                  60

Val Met Ala Gly Gly Ala Thr Gly Ala Asn Glu Thr Ile Ile Phe Cys
65                  70                  75                  80

Leu Ala Asp Pro Gly Asp Ala Phe Leu Val Pro Ser Pro Tyr Tyr Pro
                85                  90                  95

Ala

<210> SEQ ID NO 19
<211> LENGTH: 97
<212> TYPE: PRT
<213> ORGANISM: Lycopersicon esculentum

<400> SEQUENCE: 19

Leu Cys Leu Asp Leu Ile Glu Asp Trp Ile Lys Arg Asn Pro Lys Gly
1               5                   10                  15

Ser Ile Cys Ser Glu Gly Ile Lys Ser Phe Lys Ala Ile Ala Asn Phe
            20                  25                  30

Gln Asp Tyr His Gly Leu Pro Glu Phe Arg Lys Ala Ile Ala Lys Phe
        35                  40                  45

Met Glu Lys Thr Arg Gly Arg Arg Val Arg Phe Asp Pro Glu Arg Val
    50                  55                  60

Val Met Ala Gly Gly Ala Thr Gly Ala Asn Glu Thr Ile Ile Phe Cys
65                  70                  75                  80

Leu Ala Asp Pro Gly Asp Ala Phe Leu Val Pro Ser Pro Tyr Tyr Pro
                85                  90                  95

Ala

<210> SEQ ID NO 20
<211> LENGTH: 97
<212> TYPE: PRT
<213> ORGANISM: Lycopersicon esculentum

<400> SEQUENCE: 20

Leu Cys Leu Asp Leu Ile Glu Asp Trp Ile Lys Arg Asn Pro Lys Gly
1               5                   10                  15

Ser Ile Cys Ser Glu Gly Ile Lys Ser Phe Lys Ala Ile Ala Asn Phe
            20                  25                  30

Gln Asp Tyr His Gly Leu Pro Glu Phe Arg Lys Ala Ile Ala Lys Phe
        35                  40                  45

Met Glu Lys Thr Arg Gly Gly Arg Val Arg Phe Asp Leu Glu Arg Val
    50                  55                  60

Val Met Ala Gly Gly Ala Thr Gly Ala Asn Glu Thr Ile Ile Phe Cys
65                  70                  75                  80

Leu Ala Asp Pro Gly Asp Ala Phe Leu Val Pro Ser Pro Tyr Tyr Pro
                85                  90                  95

Ala

<210> SEQ ID NO 21
<211> LENGTH: 97
<212> TYPE: PRT
<213> ORGANISM: Lycopersicon esculentum

```
<400> SEQUENCE: 21

Leu Cys Leu Asp Leu Ile Glu Asp Trp Ile Lys Arg Asn Pro Lys Gly
1               5                   10                  15

Ser Ile Cys Ser Glu Gly Ile Lys Ser Phe Lys Ala Ile Ala Asn Phe
            20                  25                  30

Gln Asp Tyr His Gly Leu Pro Glu Phe Arg Lys Val Ile Ala Lys Phe
        35                  40                  45

Met Glu Lys Thr Arg Gly Gly Arg Val Arg Phe Asp Pro Glu Arg Val
    50                  55                  60

Val Met Ala Gly Gly Ala Thr Gly Ala Asn Glu Thr Ile Ile Phe Cys
65                  70                  75                  80

Leu Ala Asp Pro Gly Asp Ala Phe Leu Val Pro Ser Pro Tyr Tyr Pro
                85                  90                  95

Ala

<210> SEQ ID NO 22
<211> LENGTH: 97
<212> TYPE: PRT
<213> ORGANISM: Lycopersicon esculentum

<400> SEQUENCE: 22

Leu Cys Leu Asp Leu Ile Glu Asp Trp Ile Lys Arg Asn Pro Lys Gly
1               5                   10                  15

Ser Ile Cys Ser Glu Gly Ile Lys Ser Phe Lys Ala Ile Ala Asn Phe
            20                  25                  30

Gln Asp Tyr His Gly Leu Pro Glu Phe Arg Lys Thr Ile Ala Lys Phe
        35                  40                  45

Met Glu Lys Thr Arg Gly Gly Arg Val Arg Phe Asp Pro Glu Arg Val
    50                  55                  60

Val Met Ala Gly Gly Ala Thr Gly Ala Asn Glu Thr Ile Ile Phe Cys
65                  70                  75                  80

Leu Ala Asp Pro Gly Asp Ala Phe Leu Val Pro Ser Pro Tyr Tyr Pro
                85                  90                  95

Ala

<210> SEQ ID NO 23
<211> LENGTH: 115
<212> TYPE: PRT
<213> ORGANISM: Lycopersicon esculentum
<220> FEATURE:
<221> NAME/KEY: misc_feature
<222> LOCATION: (115)..(115)
<223> OTHER INFORMATION: Xaa can be any naturally occurring amino acid

<400> SEQUENCE: 23

Ala Val Lys Glu Ala Tyr Glu Asn Ala Gln Lys Ser Asn Ile Lys Val
1               5                   10                  15

Lys Gly Leu Ile Leu Thr Asn Pro Ser Asn Pro Leu Gly Thr Thr Leu
            20                  25                  30

Asp Lys Asp Thr Leu Lys Ser Val Leu Ser Phe Thr Asn Gln His Asn
        35                  40                  45

Ile His Leu Val Cys Asp Glu Ile Tyr Ala Ala Thr Val Phe Asp Thr
    50                  55                  60

Pro Gln Phe Val Ser Ile Ala Glu Ile Leu Asp Glu Gln Glu Met Thr
65                  70                  75                  80

Tyr Tyr Asn Lys Asp Leu Val His Ile Val Tyr Ser Leu Ser Lys Asp
                85                  90                  95
```

```
Met Gly Leu Pro Gly Phe Arg Val Gly Ile Ile Tyr Ser Phe Asn Asp
            100                 105                 110

Asp Val Xaa
        115

<210> SEQ ID NO 24
<211> LENGTH: 97
<212> TYPE: PRT
<213> ORGANISM: Lycopersicon esculentum

<400> SEQUENCE: 24

Leu Cys Leu Asp Leu Ile Glu Asp Trp Ile Lys Arg Asn Pro Lys Gly
1               5                   10                  15

Ser Ile Cys Ser Glu Gly Ile Lys Ser Phe Lys Ala Ile Ala Asn Phe
            20                  25                  30

Gln Asp Tyr His Gly Leu Pro Glu Phe Arg Lys Ala Ile Ala Lys Phe
        35                  40                  45

Met Glu Lys Thr Arg Gly Gly Arg Val Arg Phe Asp Pro Glu Arg Val
    50                  55                  60

Val Met Ala Gly Gly Ala Thr Gly Ala Asn Glu Thr Ile Ile Phe Cys
65                  70                  75                  80

Leu Ala Asp Pro Gly Asp Ala Phe Leu Glu Pro Ser Pro Tyr Tyr Pro
                85                  90                  95

Ala

<210> SEQ ID NO 25
<211> LENGTH: 476
<212> TYPE: PRT
<213> ORGANISM: Lycopersicon esculentum

<400> SEQUENCE: 25

Met Asp Leu Glu Thr Ser Glu Ile Ser Asn Tyr Lys Ser Ser Val Val
1               5                   10                  15

Leu Ser Lys Leu Ala Ser Asn Glu Gln His Gly Glu Asn Ser Pro Tyr
            20                  25                  30

Phe Asp Gly Trp Lys Ala Tyr Asp Asn Asp Pro Phe His Leu Val Asn
        35                  40                  45

Asn Leu Asn Gly Val Ile Gln Met Gly Leu Ala Glu Asn Gln Leu Ser
    50                  55                  60

Val Asp Leu Ile Glu Glu Trp Ile Lys Arg Asn Pro Lys Ala Ser Ile
65                  70                  75                  80

Cys Thr Asn Asp Gly Ile Glu Ser Phe Arg Arg Ile Ala Asn Phe Gln
                85                  90                  95

Asp Tyr His Gly Leu Pro Glu Phe Thr Asn Ala Ile Ala Lys Phe Met
            100                 105                 110

Glu Lys Thr Arg Gly Gly Lys Val Lys Phe Asp Ala Lys Arg Val Val
        115                 120                 125

Met Ala Gly Gly Ala Thr Gly Ala Asn Glu Thr Leu Ile Leu Cys Leu
    130                 135                 140

Ala Asp Pro Gly Asp Ala Phe Leu Val Pro Thr Pro Tyr Tyr Pro Gly
145                 150                 155                 160

Phe Asn Arg Asp Leu Arg Trp Arg Ser Gly Val Gln Leu Leu Pro Ile
                165                 170                 175

Ser Cys Lys Ser Cys Asn Asn Phe Lys Ile Thr Ile Glu Ala Ile Glu
            180                 185                 190
```

```
Glu Ala Tyr Glu Lys Gly Gln Gln Ala Asn Val Lys Ile Lys Gly Leu
            195                 200                 205

Ile Leu Thr Asn Pro Cys Asn Pro Leu Gly Thr Ile Leu Asp Arg Asp
    210                 215                 220

Thr Leu Lys Lys Ile Ser Thr Phe Thr Asn Glu His Asn Ile His Leu
225                 230                 235                 240

Val Cys Asp Glu Ile Tyr Ala Ala Thr Val Phe Asn Ser Pro Lys Phe
                245                 250                 255

Val Ser Ile Ala Glu Ile Ile Asn Glu Asp Asn Cys Ile Asn Lys Asp
                260                 265                 270

Leu Val His Ile Val Ser Ser Leu Ser Lys Asp Leu Gly Phe Pro Gly
            275                 280                 285

Phe Arg Val Gly Ile Val Tyr Ser Phe Asn Asp Asp Val Val Asn Cys
290                 295                 300

Ala Arg Lys Met Ser Ser Phe Gly Leu Val Ser Thr Gln Thr Gln His
305                 310                 315                 320

Leu Leu Ala Phe Met Leu Ser Asp Asp Glu Phe Val Glu Glu Phe Leu
                325                 330                 335

Ile Glu Ser Ala Lys Arg Leu Arg Glu Arg Tyr Glu Lys Phe Thr Arg
            340                 345                 350

Gly Leu Glu Glu Ile Gly Ile Lys Cys Leu Glu Ser Asn Ala Gly Val
        355                 360                 365

Tyr Cys Trp Met Asp Leu Arg Ser Leu Leu Lys Glu Ala Thr Leu Asp
    370                 375                 380

Ala Glu Met Ser Leu Trp Lys Leu Ile Ile Asn Glu Val Lys Leu Asn
385                 390                 395                 400

Val Ser Pro Gly Ser Ser Phe Asn Cys Ser Glu Val Gly Trp Phe Arg
                405                 410                 415

Val Cys Phe Ala Asn Ile Asp Asp Gln Thr Met Glu Ile Ala Leu Ala
                420                 425                 430

Arg Ile Arg Met Phe Met Asp Ala Tyr Asn Asn Val Asn Lys Asn Gly
            435                 440                 445

Val Met Lys Asn Lys His Asn Gly Arg Gly Thr Thr Tyr Asp Leu Thr
450                 455                 460

Pro Gln Met Gly Ser Thr Met Lys Met Leu Leu Ala
465                 470                 475

<210> SEQ ID NO 26
<211> LENGTH: 476
<212> TYPE: PRT
<213> ORGANISM: Lycopersicon esculentum

<400> SEQUENCE: 26

Met Asp Leu Glu Thr Ser Glu Ile Ser Asn Tyr Lys Ser Ser Val Val
1               5                   10                  15

Leu Ser Lys Leu Ala Ser Asn Glu Gln His Gly Glu Asn Ser Pro Tyr
            20                  25                  30

Phe Asp Gly Trp Lys Ala Tyr Asp Asn Asp Pro Phe His Leu Val Asn
        35                  40                  45

Asn Leu Asn Gly Val Ile Gln Met Gly Leu Ala Glu Asn Gln Leu Ser
    50                  55                  60

Val Asp Leu Ile Glu Glu Trp Ile Lys Arg Asn Pro Lys Ala Ser Ile
65                  70                  75                  80

Cys Thr Asn Asp Gly Ile Glu Ser Phe Arg Arg Ile Ala Asn Phe Gln
                85                  90                  95
```

Asp Tyr His Gly Leu Pro Glu Phe Thr Asn Ala Ile Ala Lys Phe Met
            100                 105                 110

Glu Lys Thr Arg Gly Gly Lys Val Lys Phe Asp Ala Lys Arg Val Val
        115                 120                 125

Met Ala Gly Gly Ala Thr Gly Ala Asn Glu Thr Leu Ile Leu Cys Leu
130                 135                 140

Ala Asp Pro Gly Asp Ala Phe Leu Val Pro Thr Pro Tyr Tyr Pro Gly
145                 150                 155                 160

Phe Asn Arg Asp Leu Arg Trp Arg Ser Gly Val Gln Leu Leu Pro Ile
                165                 170                 175

Ser Cys Lys Ser Cys Asn Asn Phe Lys Ile Thr Ile Glu Ala Ile Glu
                180                 185                 190

Glu Ala Tyr Glu Lys Gly Gln Gln Ala Asn Val Lys Ile Lys Gly Leu
            195                 200                 205

Ile Leu Thr Asn Pro Cys Asn Pro Leu Gly Thr Ile Leu Asp Arg Asp
        210                 215                 220

Thr Leu Lys Lys Ile Ser Thr Phe Thr Asn Glu His Asn Ile His Leu
225                 230                 235                 240

Val Cys Asp Glu Ile Tyr Ala Ala Thr Val Phe Asn Ser Pro Lys Phe
                245                 250                 255

Val Ser Ile Ala Glu Ile Ile Asn Glu Asp Asn Cys Ile Asn Lys Asp
                260                 265                 270

Leu Val His Ile Val Ser Asn Leu Ser Lys Asp Leu Gly Phe Pro Gly
            275                 280                 285

Phe Arg Val Gly Ile Val Tyr Ser Phe Asn Asp Asp Val Val Asn Cys
        290                 295                 300

Ala Arg Lys Met Ser Ser Phe Gly Leu Val Ser Thr Gln Thr Gln His
305                 310                 315                 320

Leu Leu Ala Phe Met Leu Ser Asp Asp Glu Phe Val Glu Glu Phe Leu
                325                 330                 335

Ile Glu Ser Ala Lys Arg Leu Arg Glu Arg Tyr Glu Lys Phe Thr Arg
                340                 345                 350

Gly Leu Glu Glu Ile Gly Ile Lys Cys Leu Glu Ser Asn Ala Gly Val
            355                 360                 365

Tyr Cys Trp Met Asp Leu Arg Ser Leu Leu Lys Glu Ala Thr Leu Asp
370                 375                 380

Ala Glu Met Ser Leu Trp Lys Leu Ile Ile Asn Glu Val Lys Leu Asn
385                 390                 395                 400

Val Ser Pro Gly Ser Ser Phe Asn Cys Ser Glu Val Gly Trp Phe Arg
                405                 410                 415

Val Cys Phe Ala Asn Ile Asp Asp Gln Thr Met Glu Ile Ala Leu Ala
                420                 425                 430

Arg Ile Arg Met Phe Met Asp Ala Tyr Asn Val Asn Lys Asn Gly
            435                 440                 445

Val Met Lys Asn Lys His Asn Gly Arg Gly Thr Thr Tyr Asp Leu Thr
            450                 455                 460

Pro Gln Met Gly Ser Thr Met Lys Met Leu Leu Ala
465                 470                 475

<210> SEQ ID NO 27
<211> LENGTH: 476
<212> TYPE: PRT
<213> ORGANISM: Lycopersicon esculentum

```
<400> SEQUENCE: 27

Met Asp Leu Glu Thr Ser Glu Ile Ser Asn Tyr Lys Ser Ser Val Val
1               5                   10                  15

Leu Ser Lys Leu Ala Ser Asn Glu Gln His Gly Glu Asn Ser Pro Tyr
            20                  25                  30

Phe Asp Gly Trp Lys Ala Tyr Asp Asn Asp Pro Phe His Leu Val Asn
        35                  40                  45

Asn Leu Asn Gly Val Ile Gln Met Gly Leu Ala Glu Asn Gln Leu Ser
    50                  55                  60

Val Asp Leu Ile Glu Glu Trp Ile Lys Arg Asn Pro Lys Ala Ser Ile
65                  70                  75                  80

Cys Thr Asn Asp Gly Ile Glu Ser Phe Arg Arg Ile Ala Asn Phe Gln
                85                  90                  95

Asp Tyr His Gly Leu Pro Glu Phe Thr Asn Ala Ile Ala Lys Phe Met
            100                 105                 110

Glu Lys Thr Arg Gly Gly Lys Val Lys Phe Asp Ala Lys Arg Val Val
        115                 120                 125

Met Ala Gly Gly Ala Thr Gly Ala Asn Glu Thr Leu Ile Leu Cys Leu
130                 135                 140

Ala Asp Pro Gly Asp Ala Phe Leu Val Pro Thr Pro Tyr Tyr Pro Gly
145                 150                 155                 160

Phe Asn Arg Asp Leu Arg Trp Arg Ser Gly Val Gln Leu Leu Pro Ile
                165                 170                 175

Ser Cys Lys Ser Cys Asn Asn Phe Lys Ile Thr Ile Glu Ala Ile Glu
            180                 185                 190

Glu Ala Tyr Glu Lys Gly Gln Gln Ala Asn Val Lys Ile Lys Gly Leu
        195                 200                 205

Ile Leu Thr Asn Pro Cys Asn Pro Leu Gly Thr Ile Leu Asp Arg Asp
    210                 215                 220

Thr Leu Lys Lys Ile Ser Thr Phe Thr Asn Glu His Asn Ile His Leu
225                 230                 235                 240

Val Cys Asp Glu Ile Tyr Ala Val Thr Val Phe Asn Ser Pro Lys Phe
                245                 250                 255

Val Ser Ile Ala Glu Ile Ile Asn Glu Asp Asn Cys Ile Asn Lys Asp
            260                 265                 270

Leu Val His Ile Val Ser Ser Leu Ser Lys Asp Leu Gly Phe Pro Gly
        275                 280                 285

Phe Arg Val Gly Ile Val Tyr Ser Phe Asn Asp Val Val Asn Cys
    290                 295                 300

Ala Arg Lys Met Ser Ser Phe Gly Leu Val Ser Thr Gln Thr Gln His
305                 310                 315                 320

Leu Leu Ala Phe Met Leu Ser Asp Asp Glu Phe Val Glu Glu Phe Leu
                325                 330                 335

Ile Glu Ser Ala Lys Arg Leu Arg Glu Arg Tyr Glu Lys Phe Thr Arg
            340                 345                 350

Gly Leu Glu Glu Ile Gly Ile Lys Cys Leu Glu Ser Asn Ala Gly Val
        355                 360                 365

Tyr Cys Trp Met Asp Leu Arg Ser Leu Leu Lys Glu Ala Thr Leu Asp
    370                 375                 380

Ala Glu Met Ser Leu Trp Lys Leu Ile Ile Asn Glu Val Lys Leu Asn
385                 390                 395                 400

Val Ser Pro Gly Ser Ser Phe Asn Cys Ser Glu Val Gly Trp Phe Arg
                405                 410                 415
```

```
Val Cys Phe Ala Asn Ile Asp Asp Gln Thr Met Glu Ile Ala Leu Ala
            420                 425                 430

Arg Ile Arg Met Phe Met Asp Ala Tyr Asn Asn Val Asn Lys Asn Gly
            435                 440                 445

Val Met Lys Asn Lys His Asn Gly Arg Gly Thr Thr Tyr Asp Leu Thr
450                 455                 460

Pro Gln Met Gly Ser Thr Met Lys Met Leu Leu Ala
465                 470                 475

<210> SEQ ID NO 28
<211> LENGTH: 203
<212> TYPE: PRT
<213> ORGANISM: Lycopersicon esculentum

<400> SEQUENCE: 28

Met Asp Leu Glu Thr Ser Glu Ile Ser Asn Tyr Lys Ser Ser Val Val
1               5                   10                  15

Leu Ser Lys Leu Ala Ser Asn Glu Gln His Gly Glu Asn Ser Pro Tyr
            20                  25                  30

Phe Asp Gly Trp Lys Ala Tyr Asp Asn Asp Pro Phe His Leu Val Asn
        35                  40                  45

Asn Leu Asn Gly Val Ile Gln Met Gly Leu Ala Glu Asn Gln Leu Ser
    50                  55                  60

Val Asp Leu Ile Glu Glu Trp Ile Lys Arg Asn Pro Lys Ala Ser Ile
65                  70                  75                  80

Cys Thr Asn Asp Gly Ile Glu Ser Phe Arg Arg Ile Ala Asn Phe Gln
                85                  90                  95

Asp Tyr His Gly Leu Pro Glu Phe Thr Asn Ala Ile Ala Lys Phe Met
            100                 105                 110

Glu Lys Thr Arg Gly Gly Lys Val Lys Phe Asp Ala Lys Arg Val Val
        115                 120                 125

Met Ala Gly Gly Ala Thr Gly Ala Asn Glu Thr Leu Ile Leu Cys Leu
    130                 135                 140

Ala Asp Pro Gly Asp Ala Phe Leu Val Pro Thr Pro Tyr Tyr Pro Gly
145                 150                 155                 160

Phe Asn Arg Asp Leu Arg Trp Arg Ser Gly Val Gln Leu Leu Pro Ile
                165                 170                 175

Ser Cys Lys Ser Cys Asn Asn Phe Lys Ile Thr Ile Glu Ala Ile Glu
            180                 185                 190

Glu Ala Tyr Glu Lys Gly Gln Gln Ala Asn Val
        195                 200

<210> SEQ ID NO 29
<211> LENGTH: 476
<212> TYPE: PRT
<213> ORGANISM: Lycopersicon esculentum

<400> SEQUENCE: 29

Met Asp Leu Glu Thr Ser Glu Ile Ser Asn Tyr Lys Ser Ser Val Val
1               5                   10                  15

Leu Ser Lys Leu Ala Ser Asn Glu Gln His Gly Glu Asn Ser Pro Tyr
            20                  25                  30

Phe Asp Gly Trp Lys Ala Tyr Asp Asn Asp Pro Phe His Leu Val Asn
        35                  40                  45

Asn Leu Asn Gly Val Ile Gln Met Gly Leu Ala Glu Asn Gln Leu Ser
    50                  55                  60
```

```
Val Asp Leu Ile Glu Glu Trp Ile Lys Arg Asn Pro Lys Ala Ser Ile
 65                  70                  75                  80

Cys Thr Asn Asp Gly Ile Glu Ser Phe Arg Arg Ile Ala Asn Phe Gln
                 85                  90                  95

Asp Tyr His Gly Leu Pro Glu Phe Thr Asn Ala Ile Ala Lys Phe Met
            100                 105                 110

Glu Lys Thr Arg Gly Gly Lys Val Lys Phe Asp Ala Lys Arg Val Val
            115                 120                 125

Met Ala Gly Gly Ala Thr Gly Ala Asn Glu Thr Leu Ile Leu Cys Leu
130                 135                 140

Ala Asp Pro Gly Asp Ala Phe Leu Val Pro Thr Pro Tyr Tyr Pro Gly
145                 150                 155                 160

Phe Asn Arg Asp Leu Arg Trp Arg Ser Gly Val Gln Leu Leu Pro Ile
                165                 170                 175

Ser Cys Lys Ser Cys Asn Asn Phe Lys Ile Thr Ile Glu Ala Ile Glu
            180                 185                 190

Glu Ala Tyr Glu Lys Gly Gln Gln Ala Asn Val Lys Ile Lys Gly Leu
            195                 200                 205

Ile Leu Thr Asn Pro Cys Asn Pro Leu Gly Thr Ile Leu Asp Arg Asp
210                 215                 220

Thr Leu Lys Lys Ile Ser Thr Phe Thr Asn Glu His Asn Ile His Leu
225                 230                 235                 240

Val Cys Asp Glu Ile Tyr Ala Ala Thr Val Phe Asn Ser Pro Lys Phe
                245                 250                 255

Val Ser Ile Ala Glu Ile Ile Asn Glu Asp Asn Cys Ile Asn Lys Asp
            260                 265                 270

Leu Val His Ile Val Ser Ser Leu Ser Lys Asp Leu Gly Phe Pro Gly
            275                 280                 285

Phe Arg Val Gly Ile Val Tyr Ser Phe Asn Asp Asp Val Val Asn Cys
290                 295                 300

Ala Arg Lys Met Ser Ser Phe Gly Leu Val Ser Thr Gln Thr Gln His
305                 310                 315                 320

Phe Leu Ala Phe Met Leu Ser Asp Asp Glu Phe Val Glu Glu Phe Leu
                325                 330                 335

Ile Glu Ser Ala Lys Arg Leu Arg Glu Arg Tyr Glu Lys Phe Thr Arg
            340                 345                 350

Gly Leu Glu Glu Ile Gly Ile Lys Cys Leu Glu Ser Asn Ala Gly Val
            355                 360                 365

Tyr Cys Trp Met Asp Leu Arg Ser Leu Leu Lys Glu Ala Thr Leu Asp
370                 375                 380

Ala Glu Met Ser Leu Trp Lys Leu Ile Ile Asn Glu Val Lys Leu Asn
385                 390                 395                 400

Val Ser Pro Gly Ser Ser Phe Asn Cys Ser Glu Val Gly Trp Phe Arg
                405                 410                 415

Val Cys Phe Ala Asn Ile Asp Asp Gln Thr Met Glu Ile Ala Leu Ala
            420                 425                 430

Arg Ile Arg Met Phe Met Asp Ala Tyr Asn Asn Val Asn Lys Asn Gly
            435                 440                 445

Val Met Lys Asn Lys His Asn Gly Arg Gly Thr Thr Tyr Asp Leu Thr
            450                 455                 460

Pro Gln Met Gly Ser Thr Met Lys Met Leu Leu Ala
465                 470                 475
```

```
<210> SEQ ID NO 30
<211> LENGTH: 476
<212> TYPE: PRT
<213> ORGANISM: Lycopersicon esculentum

<400> SEQUENCE: 30

Met Asp Leu Glu Thr Ser Glu Ile Ser Asn Tyr Lys Ser Ser Val Val
1               5                   10                  15

Leu Ser Lys Leu Ala Ser Asn Glu Gln His Gly Glu Asn Ser Pro Tyr
            20                  25                  30

Phe Asp Gly Trp Lys Ala Tyr Asp Asn Asp Pro Phe His Leu Val Asn
        35                  40                  45

Asn Leu Asn Gly Val Ile Gln Met Gly Leu Ala Glu Asn Gln Leu Ser
    50                  55                  60

Val Asp Leu Ile Glu Glu Trp Ile Lys Arg Asn Pro Lys Ala Ser Ile
65                  70                  75                  80

Cys Thr Asn Asp Gly Ile Glu Ser Phe Arg Arg Ile Ala Asn Phe Gln
                85                  90                  95

Asp Tyr His Gly Leu Pro Glu Phe Thr Asn Ala Ile Ala Lys Phe Met
            100                 105                 110

Glu Lys Thr Arg Gly Gly Lys Val Lys Phe Asp Ala Lys Arg Val Val
        115                 120                 125

Met Ala Gly Gly Ala Thr Gly Ala Asn Glu Thr Leu Ile Leu Cys Leu
130                 135                 140

Ala Asp Pro Gly Asp Ala Phe Leu Val Pro Thr Pro Tyr Tyr Pro Gly
145                 150                 155                 160

Phe Asn Arg Asp Leu Arg Trp Arg Ser Gly Val Gln Leu Leu Pro Ile
                165                 170                 175

Ser Cys Lys Ser Cys Asn Asn Phe Lys Ile Thr Ile Glu Ala Ile Glu
            180                 185                 190

Glu Ala Tyr Glu Lys Gly Gln Gln Ala Asn Val Lys Ile Lys Gly Leu
        195                 200                 205

Ile Leu Thr Asn Pro Cys Asn Pro Leu Gly Thr Ile Leu Asp Arg Asp
210                 215                 220

Thr Leu Lys Lys Ile Ser Thr Phe Thr Asn Glu His Asn Ile His Leu
225                 230                 235                 240

Val Cys Asp Glu Ile Tyr Ala Ala Thr Glu Phe Asn Ser Pro Lys Phe
                245                 250                 255

Val Ser Ile Ala Glu Ile Ile Asn Glu Asp Asn Cys Ile Asn Lys Asp
            260                 265                 270

Leu Val His Ile Val Ser Ser Leu Ser Lys Asp Leu Gly Phe Pro Gly
        275                 280                 285

Phe Arg Val Gly Ile Val Tyr Ser Phe Asn Asp Asp Val Val Asn Cys
290                 295                 300

Ala Arg Lys Met Ser Ser Phe Gly Leu Val Ser Thr Gln Thr Gln His
305                 310                 315                 320

Leu Leu Ala Phe Met Leu Ser Asp Asp Glu Phe Val Glu Glu Phe Leu
                325                 330                 335

Ile Glu Ser Ala Lys Arg Leu Arg Glu Arg Tyr Glu Lys Phe Thr Arg
            340                 345                 350

Gly Leu Glu Glu Ile Gly Ile Lys Cys Leu Glu Ser Asn Ala Gly Val
        355                 360                 365

Tyr Cys Trp Met Asp Leu Arg Ser Leu Leu Lys Glu Ala Thr Leu Asp
370                 375                 380
```

```
Ala Glu Met Ser Leu Trp Lys Leu Ile Ile Asn Val Lys Leu Asn
385                 390                 395                 400

Val Ser Pro Gly Ser Ser Phe Asn Cys Ser Glu Val Gly Trp Phe Arg
            405                 410                 415

Val Cys Phe Ala Asn Ile Asp Asp Gln Thr Met Glu Ile Ala Leu Ala
                420                 425                 430

Arg Ile Arg Met Phe Met Asp Ala Tyr Asn Asn Val Asn Lys Asn Gly
            435                 440                 445

Val Met Lys Asn Lys His Asn Gly Arg Gly Thr Thr Tyr Asp Leu Thr
        450                 455                 460

Pro Gln Met Gly Ser Thr Met Lys Met Leu Leu Ala
465                 470                 475
```

<210> SEQ ID NO 31
<211> LENGTH: 476
<212> TYPE: PRT
<213> ORGANISM: Lycopersicon esculentum

<400> SEQUENCE: 31

```
Met Asp Leu Glu Thr Ser Glu Ile Ser Asn Tyr Lys Ser Ser Val Val
1               5                   10                  15

Leu Ser Lys Leu Ala Ser Asn Glu Gln His Gly Glu Asn Ser Pro Tyr
                20                  25                  30

Phe Asp Gly Trp Lys Ala Tyr Asp Asn Asp Pro Phe His Leu Val Asn
            35                  40                  45

Asn Leu Asn Gly Val Ile Gln Met Gly Leu Ala Glu Asn Gln Leu Ser
        50                  55                  60

Val Asp Leu Ile Glu Glu Trp Ile Lys Arg Asn Pro Lys Ala Ser Ile
65                  70                  75                  80

Cys Thr Asn Asp Gly Ile Glu Ser Phe Arg Arg Ile Ala Asn Phe Gln
                85                  90                  95

Asp Tyr His Gly Leu Pro Glu Phe Thr Asn Ala Ile Ala Lys Phe Met
            100                 105                 110

Glu Lys Thr Arg Gly Gly Lys Val Lys Phe Asp Ala Lys Arg Val Val
        115                 120                 125

Met Ala Gly Gly Ala Thr Gly Ala Asn Glu Thr Leu Ile Leu Cys Leu
130                 135                 140

Ala Asp Pro Gly Asp Ala Phe Leu Val Pro Thr Pro Tyr Tyr Pro Gly
145                 150                 155                 160

Phe Asn Arg Asp Leu Arg Trp Arg Ser Gly Val Gln Leu Leu Pro Ile
                165                 170                 175

Ser Cys Lys Ser Cys Asn Asn Phe Lys Ile Thr Ile Glu Ala Ile Glu
            180                 185                 190

Glu Ala Tyr Glu Lys Gly Gln Gln Ala Asn Val Lys Ile Lys Gly Leu
        195                 200                 205

Ile Leu Thr Asn Pro Cys Asn Pro Leu Gly Thr Ile Leu Asp Arg Asp
210                 215                 220

Thr Leu Lys Lys Ile Ser Thr Phe Thr Asn Glu His Asn Ile His Leu
225                 230                 235                 240

Val Cys Asp Glu Ile Tyr Ala Ala Thr Val Phe Asn Ser Pro Lys Phe
                245                 250                 255

Val Ser Ile Ala Glu Ile Ile Asn Glu Asp Asn Cys Ile Asn Lys Asp
            260                 265                 270

Leu Val His Ile Val Ser Ser Leu Ser Lys Asp Leu Gly Phe Pro Gly
```

```
                275                 280                 285
Phe Arg Val Gly Ile Val Tyr Ser Phe Asn Asp Val Val Asn Cys
    290                 295                 300

Ala Arg Lys Met Ser Ser Phe Gly Leu Val Ser Ile Gln Thr Gln His
305                 310                 315                 320

Leu Leu Ala Phe Met Leu Ser Asp Asp Glu Phe Val Glu Glu Phe Leu
                325                 330                 335

Ile Glu Ser Ala Lys Arg Leu Arg Glu Arg Tyr Glu Lys Phe Thr Arg
                340                 345                 350

Gly Leu Glu Glu Ile Gly Ile Lys Cys Leu Glu Ser Asn Ala Gly Val
            355                 360                 365

Tyr Cys Trp Met Asp Leu Arg Ser Leu Leu Lys Glu Ala Thr Leu Asp
    370                 375                 380

Ala Glu Met Ser Leu Trp Lys Leu Ile Ile Asn Glu Val Lys Leu Asn
385                 390                 395                 400

Val Ser Pro Gly Ser Ser Phe Asn Cys Ser Glu Val Gly Trp Phe Arg
                405                 410                 415

Val Cys Phe Ala Asn Ile Asp Asp Gln Thr Met Glu Ile Ala Leu Ala
                420                 425                 430

Arg Ile Arg Met Phe Met Asp Ala Tyr Asn Asn Val Asn Lys Asn Gly
            435                 440                 445

Val Met Lys Asn Lys His Asn Gly Arg Gly Thr Thr Tyr Asp Leu Thr
    450                 455                 460

Pro Gln Met Gly Ser Thr Met Lys Met Leu Leu Ala
465                 470                 475
```